(12) United States Patent
Chakraborty et al.

(10) Patent No.: US 11,161,882 B2
(45) Date of Patent: Nov. 2, 2021

(54) MONOCINS AND METHODS OF USE

(71) Applicant: AvidBiotics Corp., South San Francisco, CA (US)

(72) Inventors: Urmi Chakraborty, San Francisco, CA (US); Grace Lee, Pacifica, CA (US); Dean Scholl, Burlingame, CA (US)

(73) Assignee: PYLUM BIOSCIENCES, INC., Lewes, DE (US)

( * ) Notice: Subject to any disclaimer, the term of this patent is extended or adjusted under 35 U.S.C. 154(b) by 724 days.

(21) Appl. No.: 14/934,762

(22) Filed: Nov. 6, 2015

(65) Prior Publication Data

US 2016/0130309 A1 May 12, 2016

Related U.S. Application Data

(60) Provisional application No. 62/076,691, filed on Nov. 7, 2014, provisional application No. 62/245,493, filed on Oct. 23, 2015.

(51) Int. Cl.
| | | |
|---|---|---|
| *C07K 14/195* | (2006.01) | |
| *A01N 37/46* | (2006.01) | |
| *A61K 38/00* | (2006.01) | |

(52) U.S. Cl.
CPC ............ *C07K 14/195* (2013.01); *A01N 37/46* (2013.01); *A61K 38/00* (2013.01)

(58) Field of Classification Search
CPC .... C07K 14/195; A61K 38/00; A61K 38/162; A61K 38/164; A01N 37/46
See application file for complete search history.

(56) References Cited

U.S. PATENT DOCUMENTS

2006/0078901 A1 * 4/2006 Buchrieser ........... C07K 14/195
435/6.11

FOREIGN PATENT DOCUMENTS

WO WO-0177335 A2 * 10/2001 ........... C07K 14/195

OTHER PUBLICATIONS

Zink et al. Supplementary Listeria-typing with defective Listeria phage particles (monocins). Letters in Applied Microbiology, vol. 19, pp. 99-101, 1994. (Year: 1994).*

Zink et al. Characterization of cryptic prophages (monocins) in Listeria and sequence analysis of holin/endolysin gene. Microbiology, vol. 141, pp. 2577-2584, 1995. (Year: 1995).*

Williams et al. Retargeting R-type pyocins to generate novel bactericidal protein complexes. Applied and Environmental Microbiology, vol. 74, No. 12, pp. 3868-3876, Jun. 2008, including pp. 1/4-4/4 of Supplemental Material. (Year: 2008).*

Ghequire et al. The tailocin tail: Peeling off phage tails. Trends in Microbiology, vol. 23, No. 10, pp. 587-590, Oct. 2015. (Year: 2015).*

Merrikin et al. Use of pyocin 78-C2 in the treatment of A Pseudomonas aeruginosa infection in mice. Applied Microbiology, vol. 23, No. 1, pp. 164-165, Jan. 1972. (Year: 1972).*

Haas et al. Protective effect of pyocin against lethal Pseudomonas aeruginosa infections in mice. The Journal of Infectious Diseases, vol. 129, No. 4, pp. 470-472, Apr. 1974. (Year: 1974).*

Williams. Treatment of Pseudomonas aeruginosa infections with pyocines. Journal of Medical Microbiology, vol. 9, pp. 153-161, 1976. (Year: 1976).*

Payne et al. Phage therapy: The peculiar kinetics of self-replicating pharmaceuticals. Clinical Pharmacology & Therapeutics, vol. 68, No. 3, pp. 225-230, Sep. 2000. (Year: 2000).*

Skurnik et al. Phage therapy: Facts and fiction. International Journal of Medical Microbiology, vol. 296, pp. 5-14, Feb. 2006. (Year: 2006).*

Tsonos et al. A cocktail of in vitro efficient phages is not a guarantee for in vivo therapeutic results against avian colibacillosis. Veterinary Microbiology, vol. 171, pp. 470-479, Jul. 2014, Epub Nov. 4, 2013. (Year: 2013).*

Scholl et al. An engineered R-type pyocin is a highly specific and sensitive bactericidal agent for the good-borne pathogen *Escherichia coli* O154:57. Antimicrobial Agents and Chemotherapy, vol. 53, No. 7, pp. 3074-3080, Jul. 2009, including p. 1/4-4/4 of Supplemental Tables. (Year: 2009).*

GenBank Accession No. EAL07464.1, publicly available May 2004, printed as p. 1/1. (Year: 2004).*

* cited by examiner

*Primary Examiner* — Jennifer Dunston

(74) *Attorney, Agent, or Firm* — Sughrue Mion, PLLC

(57) ABSTRACT

The disclosure relates to the identification, cloning, and expression of a genetic locus within a *Listeria monocytogenes* genome that encodes a phage tail-like bacteriocin (PTLB), termed a monocin. Also provided are non-natural monocins, which have been engineered to have altered bactericidal specificity. Nucleic acid molecules encoding natural or non-natural monocins, vector constructs containing such nucleic acids operably linked to a heterologous promoter, producer cells containing such vectors, the encoded monocins, as well as methods of making and using such monocins are described.

27 Claims, 7 Drawing Sheets
(4 of 7 Drawing Sheet(s) Filed in Color)

Specification includes a Sequence Listing.

MONOCINS AND METHODS OF USE

CROSS REFERENCE TO RELATED APPLICATIONS

This application claims the benefit of United States Provisional Application Nos. 62/076,691, filed Nov. 7, 2014, and 62/245,493, filed Oct. 23, 2015, the contents of all of which are incorporated herein by reference in their entirety.

BACKGROUND OF THE INVENTION

Field of the Invention

This application relates generally to the identification, isolation, modification and expression of a cluster of genes sufficient to produce a bacteriocin, and more specifically, a Phage tail-like bacteriocin (PTLB) that specifically kills *Listeria* species, and methods to alter its bactericidal specificity, produce, and use the same.

Background Information

*Listeria* is a genus of bacteria, which includes at least fifteen species. *Listeria* species are gram-positive bacilli that are facultative anaerobes (i.e., capable of surviving in the presence or absence of oxygen). The major human pathogen in the *Listeria* genus is *L. monocytogenes*, which can grow and reproduce inside the infected host's cells and is one of the most virulent food-borne pathogens. *L. monocytogenes* is usually the causative agent of the relatively rare bacterial disease, listeriosis. Listeriosis is a serious disease for humans caused by eating food contaminated with the bacteria. The disease affects primarily pregnant women, newborns, adults with weakened immune systems, and the elderly. The overt form of the disease has a mortality rate of about 20 percent. The two main clinical manifestations are sepsis and meningitis. *Listeria ivanovii* is a pathogen of mammals, specifically ruminants, and has rarely caused listeriosis in humans.

Several strains of *Listeria* sps (*monocytogenes, innocua, ivanovii*) have been shown upon induction of the SOS response to produce high molecular weight (HMW) bacteriocins or Phage tail-like bacteriocins (PTLBs) termed "monocins" (Zink et al., 1994). These particles are released into the medium upon lysis of the monocin producer cells and have been shown by spot plate assay to have bactericidal activity on other *Listeria* strains. Particle production was confirmed by electron microscopy. Monocins produced by different strains displayed different bactericidal spectra. The genetic locus encoding a monocin has not been identified. The sequence of a putative monocin lytic enzyme was erroneously described many years ago (Zink et al., 1995; see below).

SUMMARY OF THE INVENTION

The present invention relates to the identification, cloning, and expression of a genetic locus within a *Listeria* genome that as a cluster of genes encodes a Phage tail-like bacteriocin (PTLB), termed a monocin or listeriocin, interchangeably. The present invention also relates to modified monocins. Monocins contain a receptor binding protein (RBP) that directs the binding of the monocin to the bacterium that it kills.

Accordingly, in one aspect, there are provided isolated nucleic acid molecules encoding a non-natural monocin, wherein the nucleic acid molecule contains a first polynucleotide that encodes a monocin structural scaffold, and a second polynucleotide encoding a heterologous RBP, wherein the scaffold contains all structural proteins of a functional monocin except its corresponding natural RBP, and wherein the monocin has bactericidal specificity as determined by the heterologous RBP. In some embodiments, the scaffold encoded by the first polynucleotide is at least 80% identical to SEQ ID NOs: 7-16, amino acid sequences ORFs 130-139.

In another aspect, there are provided producer cell integration vectors containing the disclosed nucleic acid molecule encoding a monocin, wherein the nucleic acid molecule is operably linked to a heterologous inducible promoter. In some embodiments, the producer cell is *Bacillus subtilis*. *B. subtilis* does not naturally produce a monocin.

In still another aspect, there are provided nucleic acid molecules encoding a monocin, wherein the nucleic acid molecule contains a polynucleotide that encodes amino acid sequences that are at least 80% identical to SEQ ID NOs: 5-17 and a heterologous promoter inducible by a small molecule, wherein the monocin has bactericidal activity, and wherein the polynucleotide is operably linked to the heterologous promoter. In particular embodiments, the promoter is placed at approximately 11, 14, 17, 20, or 23 nucleotides upstream of the portion of the polynucleotide encoding SEQ ID NO: 5. In a further aspect, there are provided monocin producer cells containing the disclosed nucleic acid molecules encoding a monocin. In some embodiments, the monocin producer cell contains a first foreign polynucleotide that encodes amino acid sequences that are at least 80% identical to SEQ ID NOs: 7-16 and a second foreign polynucleotide encoding an RBP, wherein the first and second polynucleotides encode a monocin having bactericidal specificity as determined by the RBP. In yet another aspect, there are provided methods of producing a monocin, by exposing a monocin producer cell containing a nucleic acid molecule encoding a monocin, wherein the nucleic acid molecule is operably linked to a heterologous inducible promoter, to an inducing agent in a concentration effective to induce expression of the monocin via the inducible promoter, thereby producing the monocin. In some embodiments, the nucleic acid molecule encoding a monocin is integrated within the genome of the producer cell in order to generate a stable monocin producer cell. In another aspect, there are provided methods of killing a *Listeria* species, comprising contacting the *Listeria* species with an effective amount of a monocin of the disclosure, whereby the monocin binds and kills the *Listeria* species. In some embodiments, the contacting is with a surface contaminated with *Listeria* species. In one example, the contacting is at 2-10° C. In another aspect, there are provided methods of treating an infection of *Listeria* species in an animal comprising, administering to an animal in need thereof an amount of a monocin of the disclosure, or a monocin producer cell of the disclosure in an amount sufficient to produce a bactericidal amount of the monocin, thereby treating the *Listeria* infection or colonization.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
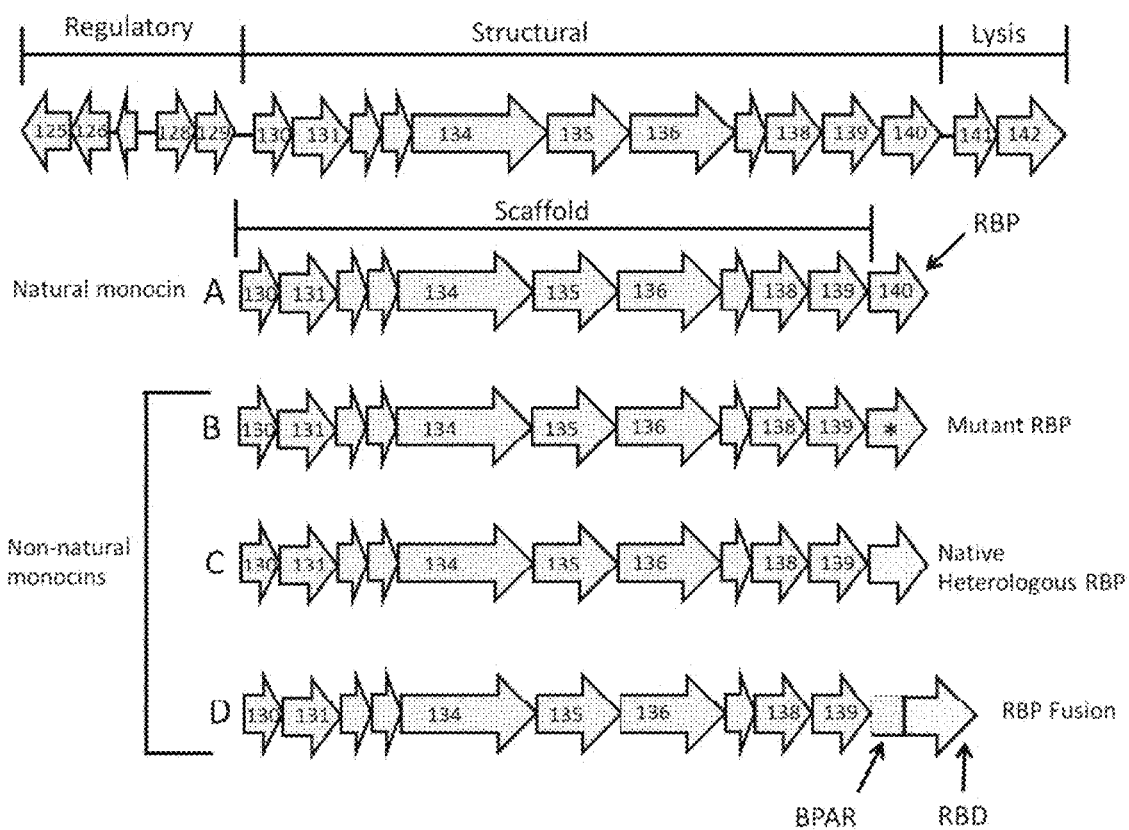
FIG. 1. Map of the genetic locus of monocins. The top is the entire wild type locus including regulatory, structural, and lysis genes as indicated. A. The structural genes of the natural monocin which encode the scaffold and the natural RBP are shown. B-D show examples of non-natural monocins with 3 representative types of heterologous RBPs. B. A non-natural monocin with a mutant or modified native RBP. C. A non-natural monocin with an unmodified native but heterologous RBP (an example is monocin 35152-33090 of this invention). D. A non-natural monocin with an RBP fusion in which an amino-terminal portion of the monocin BPAR is fused to a heterologous RBD, which can be derived from a bacteriophage, prophage, or prophage remnant (an example is monocin 35152-A118 of this invention).

The present invention is based on the identification, cloning, and expression of a genetic locus within a Listeria genome that encodes a Phage tail-like bacteriocin (PTLB), termed a monocin or listeriocin. Also provided are modified or non-natural monocins, such as those that have been engineered to have altered bactericidal specificity. Accordingly, provided herein are nucleic acid molecules encoding natural or non-natural monocins, integration vector constructs containing such nucleic acids operably linked to a heterologous promoter, producer cells that do not naturally produce monocins but containing such nucleic acid molecules or vectors, the encoded monocins, as well as methods of making and using such monocins.

As used interchangeably herein, the terms "Phage tail-like bacteriocin" (PTLB) and high molecular weight (HMW) bacteriocin may include, F-type bacteriocins (FTBs) and R-type bacteriocins (RTBs). For example, a monocin is a PTLB. The present inventors previously posited that monocins as contemplated herein have the structures of (RTBs), see U.S. Provisional Application No. 62/076,691, but as described herein, more closely resemble FTBs. A PTLB may be natural or non-natural, that is it exists in nature or does not exist in nature, respectively.

The terms "monocin" and "listeriocin" are used interchangeably herein, and refer to a PTLB isolated from or derived from a Listeria species. Monocins disclosed herein are complex molecules comprising multiple protein, or polypeptide, subunits and distantly resemble the tail structures of bacteriophages. In naturally occurring monocins the subunit structures are encoded by a genetic locus present within the bacterial genome such as that of L. monocytogenes, L. ivanovii, or L. innocua, and form monocins to serve as natural defenses against other bacteria. Monocins may be natural or non-natural.

A functional monocin contains a structural scaffold and an RBP (see FIG. 1A). Thus, the "structural scaffold" (used interchangeably with "monocin structural scaffold" or "scaffold") contains all of the structural proteins of a functional monocin except the RBP. In some embodiments, the scaffold includes the open reading frames (ORFs) corresponding to ORFs 130-139 of Listeria strain 35152. In particular embodiments, the structural scaffold includes SEQ ID NOs: 7-16. In other embodiments, the structural scaffold is at least 80% identical to SEQ ID NOs: 7-16. In other embodiments, the structural scaffold has an amino acid sequence that is at least 85%, 88%, 89%, 90%, 95%, 96%, 97%, 98%, or even 99% identical to a polypeptide containing ORFs 130-139 or SEQ ID NOs: 7-16.

The RBP consists of an amino terminal portion that provides attachment (termed the "baseplate attachment region" or BPAR) to the rest of the monocin structural scaffold and a carboxy terminal portion that provides a receptor binding domain (RBD) that is the targeting motif of the RBP. In some embodiments, the BPAR is natural to the structural scaffold. In other embodiments the BPAR is highly homologous to the BPAR native to the structural scaffold. In particular embodiments, the BPAR is at least 80% identical to the BPAR native to the structural scaffold. In particular embodiments, the BPAR includes only the amino terminal 20 to 60 amino acids of ORF 140 (see FIG. 1D).

"Natural monocins" as used herein refer to those monocins that exist in nature, and include native particles obtained from Listeria, as well as particles obtained through expression of a natural monocin gene cluster in a monocin producer cell that does not in nature produce a monocin (see FIG. 1A).

"Non-natural monocins" as used herein refer to those monocins that do not exist in nature (see FIG. 1B-1D). In other embodiments, the non-natural monocin contains a heterologous RBP. A "heterologous RBP" may be a native RBP obtained from a different source than was the structural scaffold to which it is attached (see FIG. 1B); or a heterologous RBP may be a modified RBP that was a natural RBP prior to being modified or mutated to change its physical and/or biologic properties (see FIG. 1C). In some embodiments, a modified RBP is one that contains an amino acid sequence that is different (e.g., engineered to differ) from a native or natural RBP and confers to the resulting non-natural monocin different receptor binding properties (see FIG. 1C). In other embodiments, a modified RBP may be comprised of a fusion between an amino terminal portion of a natural RBP (the BPAR) and a heterologous Receptor Binding Domain (RBD) (see FIG. 1D). An RBD is that portion of an RBP that directs the RBP, which, in turn, directs the PTLB to its specific target bacteria. In one example, a non-natural monocin may be an engineered PTLB particle comprised of polypeptides encoded by genes derived from one or more strains of *Listeria* species and 80% or more identical to the structural proteins encoded by SEQ ID NOs: 7-16 that, when incorporating a heterologous RBP, makes up a complete, active monocin.

Accordingly, there are provided nucleic acid molecules encoding a non-natural monocin, wherein the nucleic acid molecule includes a first polynucleotide that encodes all structural proteins of a functional monocin except a corresponding natural RBP, wherein the nucleic acid molecule further includes a heterologous second polynucleotide sequence encoding the heterologous RBP, and wherein the non-natural monocin has bactericidal specificity as determined by the heterologous RBP. In particular embodiments, the structural proteins encoded by the first polynucleotide correspond to ORFs 130-139 of a monocin genetic locus. In one example, the structural proteins are SEQ ID NOs: 7-16.

In particular embodiments, a non-natural monocin may include an RBP fusion. In one such example, the non-natural monocin contains a structural scaffold and an RBP fusion consisting of the BPAR from the corresponding natural RBP and a heterologous RBD. In some examples, the BPAR includes amino acid positions 1-40 of the natural RBP. To make a complete non-natural monocin molecule, the RBP fusion is attached to the structural scaffold, whereby the heterologous RBD determines the bactericidal spectrum of the resulting non-natural monocin. In examples where the non-natural monocin contains a heterologous RBP which is an RBP fusion, the nucleic acid molecule encoding the scaffold and the heterologous RBP is engineered so that the resulting monocin will contain a heterologous RBP consisting of amino acids at positions approximately 1-40 of the natural BPAR fused to the carboxy terminal portion of a heterologous RBD (see FIG. 1D).

As used herein, a "nucleic acid" or a "nucleic acid molecule" typically refers to deoxyribonucleotide or ribonucleotide polymers (pure or mixed) in single- or double-stranded form. The term may encompass nucleic acids containing nucleotide analogs or modified backbone residues or linkages, which are synthetic, naturally occurring, and non-naturally occurring, which have similar binding, structural, or functional properties as the reference nucleic acid, and which are processed in a manner similar to the reference nucleotides. Examples of such analogs include, without limitation, phosphorothioates, phosphoramidates, methyl phosphonates, chiral-methyl phosphonates, 2-0-methyl ribonucleotides, and peptide-nucleic acids (PNAs). The term nucleic acid may, in some contexts, be used interchangeably with gene, cDNA, mRNA, oligonucleotide, and polynucleotide.

A particular nucleic acid sequence also encompasses conservatively modified variants thereof (such as degenerate codon substitutions) and complementary sequences, as well as the sequence explicitly indicated. Specifically, degenerate codon substitutions may be achieved by generating sequences in which the third ("wobble") position of one or more selected (or all) codons is substituted with mixed-base and/or deoxyinosine residues. Thus, a nucleic acid sequence encoding a protein sequence disclosed herein also encompasses modified variants thereof as described herein. The terms "polypeptide", "peptide", and "protein" are typically used interchangeably herein to refer to a polymer of amino acid residues. Amino acids may be referred to herein by either their commonly known three letter symbols or by the one-letter symbols recommended by the IUPAC-IUB Biochemical Nomenclature Commission.

The term "segment" as used herein in reference to an amino acid sequence refers to a contiguous sequence of amino acids that may be 10, 12, 15, 20, 25, 50, or 100 amino acid residues in length. As used herein, the term "heterologous," when used with reference to portions of a protein or nucleic acid sequence, indicates that the sequence comprises two or more subsequences that are not usually found in nature in the same relationship to each other. In one example, the heterologous sequences are from different species of bacteria. In another example, heterologous sequences are from different strains of the same species of bacteria. In one aspect, the heterologous sequences are from different strains of *L. monocytogenes*. In another aspect the heterologous sequences are from a bacterium and a bacteriophage or prophage, or from a bacterium and a synthetic, non-natural sequence of DNA.

The heterologous RBP may be comprised of an RBD obtained from another strain of *L. monocytogenes*, another species of *Listeria*, or a genus of bacteria other than the species and strain of the bacteria from which the scaffold was derived. In some embodiments, the species of *Listeria* include *L. fleischmannii, L. grayi, L. innocua, L. ivanovii, L. marthii, L. rocourtiae, L. seeligeri, L. weihenstephanensis* and *L. welshimeri*. In other embodiments, the genus of bacteria is selected from *Clostridium, Staphylococcus, Streptococcus, Bacillus, Enterococcus, Propionibacterium*. In some embodiments, the heterologous RBD is from a *L. monocytogenes* genome, a bacteriophage, a prophage insertion or a prophage remnant that is contained within a *Listeria* genome. A "prophage remnant" or prophage element or portion, refers to a sequence that encodes only a portion of a phage or discrete phage protein(s), rather than a full phage structure. Thus, in some embodiments, a prophage remnant may include, for example, sequence encoding an RBD and other structural proteins. In certain embodiments, the RBD is of a prophage or prophage remnant from the genome of a gram positive bacterium or an RBD of a bacteriophage that infects a gram positive bacterium. In one example, the gram positive bacterium is a species of *Clostridium, Staphylococcus, Streptococcus, Bacillus, Enterococcus*, or *Propionibacterium*. In some embodiments, the natural RBP of a natural monocin may be replaced with a modified form of a native RBP. A "native RBP" refers to a RBP having an amino acid sequence that is identical to a RBP isolated or cloned from another strain of *L. monocytogenes* or from a bacteriophage that infects *L. monocytogenes* or from another genus or species of bacteria or from a bacteriophage. Exemplary native RBP from *L. monocytogenes* include SEQ ID NOs: 17 and 26, from strains 35152 and F6854, respectively, and an exemplary native RBP from *L. innocua* includes SEQ ID NO: 27 from strain 33090. In some embodiments, a modified RBP includes a change in the amino acid sequence of the RBP relative to a native RBP. Non-limiting examples of a change in amino acid sequence include substitution, insertion (or addition), or deletion of one or more amino acids that modifies the binding or stability properties of the RBP.

In particular embodiments, the modified form of a native RBP also results in a monocin having a heterologous RBP and bactericidal spectrum that is different from a monocin containing the corresponding unmodified or native RBP. In particular embodiments, the modified form is at least 80% identical to the native RBP. In other embodiments, the RBP has an amino acid sequence that is at least 85%, 88%, 89%, 90%, 95%, 96%, 97%, 98%, or even 99% identical to a polypeptide selected from the group consisting of SEQ ID NOs: 17, 26, 27 and the modified RBP results in a monocin having a bactericidal spectrum that is different from a monocin having the corresponding unmodified or native RBP.

Also provided are variant monocins. Variant monocins include those monocins having an amino acid sequence that is at least 80% identical to a polypeptide containing ORFs 130-139 (SEQ ID NOs: 7-16), or ORFs 130-140 (SEQ ID NOs: 7-17). In other embodiments, the variant monocin has an amino acid sequence that is at least 85%, 88%, 89%, 90%, 95%, 96%, 97%, 98%, or even 99% identical to a polypeptide containing ORFs 130-139, or ORFs 130-140.

Also provided are vectors or expression constructs containing a nucleic acid molecule encoding a monocin. In some embodiments, the nucleic acid molecule is operably linked to a heterologous inducible promoter in the vector or expression construct. In particular embodiments, the heterologous promoter is a small molecule induced promoter. Examples of such small molecule induced promoters include $P_{LAC}$ (lactose, IPTG), $P_{TAC}$ (IPTG), $P_{BAD}$ (arabinose), and $P_{XYL}$ (Xylose). In particular embodiments, the promoter is placed at approximately 17 nucleotides upstream of a polynucleotide encoding ORF 128 (SEQ ID NO: 5) of the monocin.

In other embodiments, the vector or expression construct may include one or more regulatory proteins encoded by a monocin genetic locus or gene cluster. In particular embodiments, the one or more regulatory proteins are encoded by an ORF selected from the group consisting of ORFs 125, 126, 127, 128, and 129 (SEQ ID NOs: 2-6, respectively). In one example, the one or more regulatory proteins are encoded by an ORF selected from the group consisting of SEQ ID NOs: 2-6.

A monocin of the invention may be cold active, that is, it has bactericidal activity in cold temperatures, such as 2-10° C.

An additional property common to the monocins disclosed herein is that they do not contain nucleic acid and thus, are replication deficient such that they cannot reproduce themselves after or during the killing of a target bacterium, as can many bacteriophages. They are purely proteins, not organisms or viruses.

A "target bacterium" or "target bacteria" refers to a bacterium or bacteria that are bound by a monocin of the disclosure and/or whose growth, survival, or replication is inhibited thereby. In some embodiments, the target bacterium is from the genus *Listeria*. In some embodiments, the target bacterium is from a species of *Listeria* selected from the group consisting of *L. monocytogenes*, *L. innocua*, and *L. ivanovii*. In particular embodiments, the bacterium is *Listeria monocytogenes*. In one aspect, more than one strain of *L. monocytogenes* is targeted. Exemplary strains of *Listeria monocytogenes* include, but are not limited to, strain 15313 (serovar 1/2a), strain 19111 (serovar 1/2a), strain 35152 (serovar 1/2a), strain DD1144 (serovar 1/2a), strain DD1145 (serovar 1/2a), strain DD1152 (serovar 1/2a), strain DD1299 (serovar 1/2a), strain DD1313 (serovar 4b), strain DD1294 (serovar 4b), strain DP-L4056 (serovar (1/2a), strain DP-L3633 (serovar 1/2a), strain DP-L3293 (serovar 1/2c), strain DP-L3817 (serovar 1/2a), strain DP-L1171 (serovar 1/2b), strain DP-L185 (serovar 4b), strain DP-L186 (serovar 4b), strain DP-L188 (serovar 3), strain DP-L1173 (serovar 4b), strain DP-L1174 (serovar 4b), strain DP-L1168 (serovar 4b), strain DP-L1169 (serovar 4b), strain 23074 (serovar 4b), and *Listeria ivanovii* strain 19119 (serovar 5). In some embodiments, the target bacterium is from the genus *Clostridum, Staphylococcus, Streptococcus, Bacillus, Enterococcus,* or *Propionibacterium*. The term "growth inhibition" or variations thereof refers to the slowing or stopping of the rate of a bacterial cell's division or cessation of bacterial cell division, or to the death of the bacterium or bacteria.

Virulence factors are those molecules that contribute to the pathogenicity of an organism but not necessarily its general viability. Upon the loss of a virulence factor the organism is less pathogenic to a host but not necessarily less viable in culture. Virulence factors may have any one of numerous functions, for example, regulating gene expression, providing adhesion or mobility, providing a toxin, injecting a toxin, pumping out antibiotic agents, or forming protective coatings including biofilms.

Fitness factors are those molecules that contribute to the organism's general viability, growth rate or competitiveness in its environment. Upon the loss of a fitness factor, the organism is less viable or competitive and because of this compromise, indirectly less pathogenic. Fitness factors may also possess any one of numerous functions, for example, acquiring nutrients, ions or water, forming components or protectants of cell membranes or cell walls, replicating, repairing or mutagenizing nucleic acids, providing defense from or offense towards environmental or competitive insults.

Monocins targeting surface accessible virulence or fitness factors (e.g., Internalins on the surfaces of *Listeria* species and S-layer proteins, prevalent on many bacteria, the *Clostridium* species, for example) offer an attractive means of forcing such pathogens to compromise their virulence or fitness if they emerge as resistant to the monocin.

In additional embodiments, a monocin as provided herein is used to treat food or food storage areas contaminated with target bacteria. In particular embodiments, the monocin is cold stable, cold active, and is used to treat bacterial contamination of refrigerated food or refrigerated storage areas. Accordingly, there are provided methods of killing *Listeria monocytogenes* by contacting the *L. monocytogenes* with an effective amount of a monocin, whereby the monocin binds and kills the *L. monocytogenes*. In some embodiments, the contacting is in an animal and a bactericidal amount of the monocin is administered to the animal. In other embodiments, the contacting is with a surface contaminated with *L. monocytogenes*. In certain embodiments, the contacting is in the cold, for example at 2-10° C.

Also provided, are methods of treating an infection of *L. monocytogenes* in an animal by administering to an animal in need thereof an amount of a monocin, or a monocin producer cell to produce a bactericidal amount of the bacteriocin, thereby treating the infection.

As described herein, an anti-bacterial monocin may be used to inhibit growth, survival, or replication of a particular bacterium. The bacterium may be a pathogenic or environmentally deleterious strain, or may be treated in a prophylactic manner. A pathogenic microorganism generally causes disease, sometimes only in particular circumstances.

An engineered monocin of the disclosure may be administered to any subject afflicted with, diagnosed as afflicted with, or suspected of being afflicted with, an infection, colonized by, or contamination by bacteria susceptible to the monocin. Non-limiting examples of such a subject include animal (mammalian, reptilian, amphibian, avian, and fish) species as well as insects, plants and fungi. Representative, and non-limiting, examples of mammalian species include humans; non-human primates; agriculturally relevant species such as cattle, pigs, goats, and sheep; rodents, such as mice and rats; mammals for companionship, display, or show, such as dogs, cats, guinea pigs, rabbits, and horses; and mammals for work, such as dogs and horses. Representative, and non-limiting, examples of avian species include chickens, ducks, geese, and birds for companionship or show, such as parrots and parakeets. An animal subject treated with an engineered monocin of the disclosure may also be a quadruped, a biped, an aquatic animal, a vertebrate, or an invertebrate, including insects.

In some embodiments, the subject in need to be treated is a human child or fetus or other young animal which has yet to reach maturity. Thus the disclosure includes the treatment of pediatric or obstetric conditions comprising infection with bacteria or other microorganism susceptible to a monocin of the disclosure.

In some embodiments, there are provided compositions of more than one non-natural monocin, wherein the non-natural monocins have differing bactericidal spectra. In other embodiments, there are provided compositions of one or more non-natural monocins and one or more natural monocins, wherein the monocins have differing bactericidal spectra.

In some embodiments, monocins, combinations of monocins, or monocin producer cells capable of producing monocins are formulated with a "pharmaceutically acceptable" excipient, enteric coating or carrier. Such a component is one that is suitable for use with humans, animals, and/or plants without undue adverse side effects. Non-limiting examples of adverse side effects include toxicity, irritation, and/or allergic response. The excipient or carrier is typically one that is commensurate with a reasonable benefit/risk ratio. Non-limiting pharmaceutically suitable carriers include sterile aqueous or non-aqueous solutions, suspensions, and emulsions. Examples include, but are not limited to, standard pharmaceutical excipients such as a phosphate buffered saline solution, bicarbonate solution, water, emulsions such as oil/water emulsion, and various types of wetting agents. Examples of non-aqueous solvents are propylene glycol, polyethylene glycol, vegetable oils such as olive oil, and injectable organic esters such as ethyloleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's or fixed oils. Intravenous vehicles include fluid and nutrient replenishers, electrolyte replenishers (such as those based on Ringer's dextrose), and the like.

Additional formulations and pharmaceutical compositions disclosed herein comprise an isolated monocin specific for a bacterial pathogen; a mixture of two, three, five, ten, or twenty or more different monocins or producer cells capable of producing monocins that target the same bacterial pathogen; and a mixture of two, three, five, ten, or twenty or more that target different bacterial pathogens or different strains of the same bacterial pathogen.

Optionally, a composition comprising a monocin or producer cell of the disclosure may also be spray dried or lyophilized using means well known in the art. Subsequent reconstitution and use may be practiced as known in the field.

A monocin is typically used in an amount or concentration that is "safe and effective", which refers to a quantity that is sufficient to produce a desired therapeutic or prophylactic response without undue adverse side effects like those described above. A monocin may also be used in an amount or concentration that is "therapeutically effective", which refers to an amount effective to yield a desired therapeutic response, such as, but not limited to, an amount effective to slow the rate of bacterial cell division, or to cause cessation of bacterial cell division, or to cause death or decrease rate of population growth of the target bacteria. The safe and effective amount or therapeutically or prophylactically effective amount will vary with various factors but may be readily determined by the skilled practitioner without undue experimentation. Non-limiting examples of factors include the particular condition being treated, the physical condition of the subject, the type of subject being treated, the duration of the treatment, the nature of concurrent therapy (if any), and the specific formulations employed.

The terms "producer cell" and "monocin producer cell" are used interchangeably herein and refer to a cell that is capable of producing or expressing a monocin-encoding nucleic acid molecule, and which does not naturally contain such a nucleic acid molecule. The producer cell may be capable of surviving and growing in the presence of oxygen and is transformed with a vector containing a nucleic acid molecule encoding the monocin, which may be integrated into the chromosome of the producer cell or may be episomal. The producer cell may be a gram positive bacterium. In certain embodiments, the producer cell may be a bacterium from the genus *Bacillus, Lactobacillus, Listeria,* or *Lactococcus.*

In some embodiments, the bacterium is a species from the genus *Bacillus* selected from the group consisting of *subtilis, amyloliquefaciens,* and *megaterium*. In one aspect, the bacterium is *Bacillus subtilis*. In a particular aspect, the producer cell is a *B. subtilis* strain that lacks the PBSX gene cluster SpoA, Flag, etc. In other embodiments, the bacterium is a species from the genus *Lactobacillus* selected from the group consisting of *acidophilus, casei,* and *bulgaricus*. In another particular embodiment the producer cell is a species of *Listeria* other than *monocytogenes* capable of producing or expressing a monocin-encoding nucleic acid molecule and which does not naturally contain such a nucleic acid molecule. In some embodiments, a producer cell contains a first foreign polynucleotide that encodes an amino acid sequence that is at least 80% identical to SEQ ID NOs: 7-16 and a second foreign polynucleotide encoding a heterologous RBP, wherein the first and second polynucleotides encode a monocin having bactericidal specificity as determined by the heterologous RBP. In particular embodiments, the second foreign polynucleotide is heterologous to the first foreign polynucleotide. In some embodiments, the first and second polynucleotides are separate nucleic acid molecules. In other embodiments, the first and second polynucleotides are contained in one nucleic acid molecule. The following examples are intended to illustrate but not limit the invention.

The term "comprising", which is used interchangeably with "including," "containing," or "characterized by," is inclusive or open-ended language and does not exclude additional, unrecited elements or method steps. The phrase "consisting of" excludes any element, step, or ingredient not specified in the claim. The phrase "consisting essentially of" limits the scope of a claim to the specified materials or steps and those that do not materially affect the basic and novel characteristics of the claimed invention. The present disclosure contemplates embodiments of the invention compositions and methods corresponding to the scope of each of these phrases. Thus, a composition or method comprising recited elements or steps contemplates particular embodiments in which the composition or method consists essentially of or consists of those elements or steps.

Example 1

Identification of the Monocin Genetic Locus

This example illustrates the identification of the genetic loci that encode a monocin within a strain of *Listeria monocytogenes* and a strain of *Listeria innocua*. *Listeria monocytogenes* strain ATCC 35152 and *Listeria innocua* strain ATCC 33090 were both reported to produce monocins. (Zink et al., 1994). These two strains were induced with mitomycin C, and the monocins were collected from the lysate by high speed centrifugation at 90,000×g. Bactericidal activity was tested by the spot method on a panel of *Listeria* species. The monocins from the two strains were found to have differing bactericidal spectra. Neither showed bactericidal activity against the same strain from which it was isolated. The entire purified monocin preparations were analyzed by mass spectrometry (MS) to identify in the sample proteins that had similarity to components of phage tail-like structures. Although strains 35152 and 33090 are not among those in which the genome sequences are known, numerous other *Listeria* genomes had been sequenced and were searchable. The most abundant protein in the preparation of monocin from strain 35152 corresponded to gene ImaA or antigen A encoded in numerous *Listeria* strains. Antigen A is a protein originally found to elicit an immune response in humans with *Listeria* infections (Gohmann et al., 1990; Schaferkordt et al., 1997). Prior to the instant invention it was not known that Antigen A was actually part of a monocin. The antigen A from strain 35152 showed identical peptide sequences to several homologues in known *Listeria monocytogenes* genomes; the sequenced genome of *L. monocytogenes* strain 1/2a F6854 was chosen as a reference, and the gene (ORF) numbering system of that strain was used for this work. The Antigen A corresponds to ORF 131 of strain 1/2a F6854. Several other peptide matches were noted from the MS analyses that corresponded to ORFs that are encoded in nearby regions of the genome including ORFs 130, 132, 135, 136, 138, and 140 (SEQ ID NOs: 7, 9, 12, 13, 15, 17, respectively). Several of these had sequence similarities to phage tail proteins (Table 1).

TABLE 1

Open reading frames, predicted amino acid lengths, and annotations of the proteins encoded by the ORFs of the monocin gene cluster. GenBank ® annotations correlate with *L. monocytogenes* strain F6854. AvidBiotics annotations are based on additional bioinformatics searches, mass spectrometry, and experimental data.

| ORF | Length (a.a.) | GenBank ® Annotation | AvidBiotics Annotation |
|---|---|---|---|
| 125 | 231 | Hypothetical | Transcriptional regulator |
| 126 | 150 | Hypothetical | Tox/Antitox, GP35 of phage A118 |
| 127 | 117 | Putative Repressor | Tox/Antitox, lambda C1, HTH |
| 128 | 142 | Antigen D | Antigen D (unknown function) |
| 129 | 138 | Antigen C | Transcriptional regulator |
| 130 | 129 | Antigen B | Antigen B (unknown function) |
| 131 | 170 | Antigen A | Major monocin structural protein |
| 132 | 100 | Hypothetical | Monocin structural protein |
| 133 | 111 | Hypothetical | Monocin structural protein |
| 134 | 622 | Putative membrane protein | Tape measure protein |
| 135 | 272 | Hypothetical | Monocin structural protein |
| 136 | 378 | Phage structural | Monocin structural protein |
| 137 | 99 | Hypothetical | Monocin structural protein |
| 138 | 191 | Hypothetical | Monocin structural protein |
| 139 | 159 | Hypothetical | Monocin structural protein |
| 140 | 178 | Hypothetical | Monocin RBP |
| 141 | 140 | Holin | Holin |
| 142 | 242 | N-acetylmuramoyl-L-alanine amidase | Lysin |

A close inspection of this genomic region revealed that ORFs 130-140 (SEQ ID NOs: 7-17, respectively) encoded the components of a contractile tail structure module (FIG. 1 top). In particular, ORF 134 encoded a putative tape measure protein, and ORFs 137 and 139 encoded putative proteins that shared at least some sequence similarity to known phage tail proteins. These ORFs are all transcribed on one strand with little intergenic space. Just downstream, ORFs 141 and 142 (SEQ ID NOs: 18-19) encoded putative holin and lysin, the proteins that are responsible for timed cell lysis for monocin release from the bacteria. Upstream of ORF 130 there were annotated 5 putative regulatory genes. ORF 125 (SEQ ID NO: 2) had sequence similarity to transcriptional regulators; ORF 126 (SEQ ID NO: 3) and 127 (SEQ ID NO: 4) had sequence similarity to phage regulatory proteins, and ORF 128 (SEQ ID NO: 5) and ORF 129 (SEQ ID NO: 6) had sequence similarities to antigen D and antigen C, respectively, with ORF 129 also having some similarity to transcriptional regulators (Table 1). ORFs 125-127 were found to be transcribed in the opposite direction from the structural genes while ORFs128 and 129 were transcribed in the same direction as the structural genes with a gap of 286 nucleotides between the end of ORF129 and the start of ORF130. A map of the entire monocin gene cluster is shown in FIG. 1 (top). No genes encoding phage capsid, capsid assembly, or portal proteins were found in this region or nearby in the genome. Also not present were any genes encoding DNA replication or packaging machinery, integration/excision proteins, or any other ORFs often associated with lysogenic prophages. Thus, this region was consistent with its encoding a predicted PTLB, including contractile phage tail components and the regulatory/lysis genes required to regulate production and release of the PTLB particles.

Mass spectrometry data of the *Listeria innocua* 33090 lysate preparation gave similar results, with several peptides corresponding to a nearly identical gene cluster. *L. monocytogenes* strain 35152, which makes natural monocin 35152, was chosen as a source for nucleic acid encoding a scaffold for engineering novel monocins and novel expression cassettes for monocins.

Example 2

Cloning and Expression of the Monocin 35152 in *Bacillus Subtilis*

This example illustrates the cloning of the genes for and expression of a monocin in a non-pathogenic producer cell.

The monocin gene cluster, from ORF 125 to ORF 142 (SEQ ID NOs: 2-19, respectively), was PCR-amplified from genomic DNA isolated from *Listeria monocytogenes* strain 35152 using primers oGL-054 and oGL-057 (Table 2). The PCR product and the vector DG630 (Gebhart et al., 2012) were both digested with restriction enzymes AscI and NotI and ligated together using T4 DNA ligase. This placed the monocin cluster between two flanking amyE sequences which allowed homologous recombination of the cluster into the amyE gene of *B. subtilis*. This plasmid construct was named pGL-031 (Table 3).

TABLE 2

Primers and oligonucleotides used in this invention.

| Primer Name | Primer sequence (5'→3') | Primer Description |
|---|---|---|
| oGL-054 | GAggcgcgccTTATCTGGTTAATAAGCCGTTTCCGG (SEQ ID NO: 39) | Forward primer to amplify monocin 35152 (ORF 125), introduces AscI restriction site. |
| oGL-057 | GAgcggccgcTTATCTTTTTCCTGTATTAACTTCTG (SEQ ID NO: 40) | Reverse primer to amplify monocin 35152 (ORF 142), introduces NotI restriction site. |
| oUC-001 | GAGCGGCCGCTTACATAATTGTTACTTGGCGAAGAG (SEQ ID NO: 41) | Reverse primer to amplify monocin 35152 (ORF 140), introduces NotI restriction site. |
| oGL-084 | GAggcgcgccGAATTcGACTCTCTAGCTTGAGGC (SEQ ID NO: 42) | Forward primer to amplify Phyper-spank promoter and lac!, introduces 5' AscI site. |
| oGL-085 | GAgcggccgcTCACTGCCCGCTTTCCAGTCG (SEQ ID NO: 43) | Reverse primer to amplify Phyper-spank promoter and lac!, introduces 5' NotI site. |
| oGL-083 | GAgcggccgcTTACATTACAGTTAGCTGGCGTAATGC (SEQ ID NO: 44) | Reverse primer to amplify 33090 ORF 174, introduces 3' NotI site. |
| oGL-075 | CTCTGACATTTTTACAATTTTAGTCATTCTATAACCTCCTTAATAGTTTCC (SEQ ID NO: 45) | Reverse overlap primer for stitching 35152 ORF 139 with 33090 ORF 174. |
| oGL-076 | GGAAACTATTAAGGAGGTTATAGAATGACTAAAATTGTAAAAATGTCAGAG (SEQ ID NO: 46) | Forward overlap primer for stitching 35152 ORF 139 with 33090 ORF 174. |
| oGL-086 | gtgagcggataacaattaGGAAGTGGGAATGGATGG (SEQ ID NO: 47) | Forward primer to amplify 35152 monocin (ORF 128) for Gibson cloning into HindIII site of pGL-034. |
| oGL-087 | ggctagctgtcgactaTTACATAATTGTTACTTGGCG (SEQ ID NO: 48) | Reverse primer to amplify 35152 monocin (ORF 140) for Gibson cloning into HindIII site of pGL-034. |
| oGL-089 | ggctagctgtcgactTTACATTACAGTTAGCTGGCGTAATGC (SEQ ID NO: 49) | Reverse primer to amplify 33090 ORF 174 for Gibson cloning into HindIII site of pGL-034. |
| oGL-112 | cgcagtatttctttttgtattccaatttGTtTTcTCTTCcTCTGaAACcg (SEQ ID NO: 50) | Reverse overlap primer for stitching 35152 ORF 140 with A118 phage tail fiber. |
| oGL-120 | GTTtCAGAgGAAGAgAAaACaaattggaatacaaaagaaaatactgcggg (SEQ ID NO: 51) | Forward overlap primer for stitching 35152 ORF 140 with A118 phage tail fiber. |
| oGL-103 | ggctagctgtcgactattatttatcatcctctccatattttttgc (SEQ ID NO: 52) | Reverse primer to amplify A118 phage tail fiber gene for Gibson cloning into HindIII site of pGL-034. |

TABLE 3

Plasmid constructs created in this invention.

| Plasmid Name | Plasmid Description | Plasmid Backbone |
| --- | --- | --- |
| pGL-031 | monocin 35152 (ORFs 125-142) cloned into DG630 using AscI and NotI sites. | DG630 |
| pUC-001 | monocin 35152 (ORFs 125-140) cloned into DG630 using AscI and NotI sites. | DG630 |
| pGL-033 | monocin 35152 (ORFs 125-139), *L. innocua* 174 cloned into AscI and NotI sites of pDG630 (restriction sites restored) | DG630 |
| pGL-034 | *Bacillus* Phyper-spank promoter and lacI cloned into DG630 using AscI and NotI sites. | DG630 |
| pGL-036 | monocin 35152 (ORFs 128-140) cloned into pGL-034 using the HindIII site. | pGL-034 |
| pGL-038 | monocin 35152 (ORFs 128-139), *L. innocua* 174 cloned into HindIII site of pGL-034. | pGL-034 |
| pGL-045 | monocin 35152 (ORFs 130-140) fused with A118 phage tail fiber gene, cloned into pGL-034 using the HindIII site. | pGL-034 |

TABLE 4

Recombinant bacterial strains generated in this invention.

| Strain Name | Strain Description | Parent Strain |
| --- | --- | --- |
| sGL-064 | *B. subtilis*/monocin 35152 (ORF 125-142). | BDG9 |
| sUC-001 | *B. subtilis*/monocin 35152 (ORF 125-140). | BDG9 |
| sGL-068 | *B. subtilis*/monocin 35152 (ORF 125-139), 33090 (ORF 174). | BDG9 |
| sGL-071 | *B. subtilis*/Phyper-spank - monocin 35152 (ORF 128-140). | BDG9 |
| sGL-075 | *B. subtilis*/Phyper-spank - monocin 35152 (ORF 128-139), 33090 (ORF 174). | BDG9 |
| sGL-092 | *B. subtilis*/Phyper-spank - monocin 35152 (ORF 128-140), A118 phage tail fiber gene. 4 downstream 118 genes | BDG9 |
| sGL-153 | *B. subtilis*/Phyper-spank - monocin 35152 (ORF 128-140), A118 phage tail fiber gene. 3 downstream 118 genes. | BDG9 |
| sGL-154 | *B. subtilis*/Phyper-spank - monocin 35152 (ORF 128-140), A118 phage tail fiber gene. 2 downstream 118 genes. | BDG9 |
| sGL155 | *B. subtilis*/Phyper-spank - monocin 35152 (ORF 128-140), A118 phage tail fiber gene. 1 downstream 118 gene. | BDG9 | pGL-031 was linearized by digestion with restriction enzyme SacII and transformed into the *Bacillus subtilis* strain, BDG9 (Gebhart et al., 2012). The transformation protocol was as follows: strain BDG9 was grown in MC medium (Gebhart et al., 2012) supplemented with final 3 mM MgSO$_4$ for four hours at 37° C. The linearized pGL-031 DNA was mixed with 200 uL of the BDG9 cells culture and allowed to incubate for an additional 2 hours at 37° C. The transformation reactions were plated on LB plates supplemented with 5 μg/mL chloramphenicol and incubated overnight at 37° C. Chloramphenicol resistant colonies were selected and tested for monocin production. This monocin producer *B. subtilis* strain was termed sGL-064 (Table 4).

*B. subtilis* strain sGL-064 was cultured using the standard conditions and monocin production was induced with 5 mM hydrogen peroxide when the OD$_{600}$ reached 0.2-0.4. The protein was harvested as described, and monocin bactericidal activity was assessed by spot assay. A spot assay is performed by adding 100 μl of target strain culture to 5 ml of TSB soft agar (0.5% agar), pouring the mixture onto a TSB agar plate, and allowing the soft agar to set. Five-fold serial dilutions of the protein preparation are made in TN50 buffer (10 mM TrisCl pH 7.5, 50 mM NaCl) and 3 μl of each dilution, including a sample of the undiluted protein preparation, are spotted onto the plate and allowed to dry. The plates are incubated overnight at 30° C. Killing is noted as zones of clearing on the bacterial lawn. Spot assays showed that the monocins produced by and purified from *B. subtilis* strains sGL-064, expressing 35152 ORF 125-ORF 142 (SEQ ID NOs: 2-19) had killing activity on *L. monocytogenes* strain 4b 23074.

Example 3

Deletion of the Lysis Genes from the Monocin Gene Cluster

This example illustrates the generation and expression of a construct containing a monocin gene cluster but lacking the genes responsible for lysis.

To remove the putative holin and lysin genes (ORFs 141-142, SEQ ID NOs: 18-19) from the monocin gene cluster, ORF 125 to ORF 140, SEQ ID NOs: 2-17, were PCR-amplified from *L. monocytogenes* 35152 genomic DNA using primers oGL-054 and oUC-001. The PCR product and the vector DG630 were both digested with restriction enzymes AscI and NotI and ligated together using T4 DNA ligase. This construct was named pUC-001. After integration into BDG9 as above, the resulting integrant strain was termed sUC-001. Spot assays showed that the monocins produced by and purified from *B. subtilis* strain sUC-001, expressing 35152 ORF 125-ORF 140 (SEQ ID NOs: 2-17), after induction as in Example 2 had bactericidal activity, as evidenced by the presence of spots on a lawn of the target, *L. monocytogenes* strain 4b 23074. Thus, by removing ORFs 141 and 142 (SEQ ID NOs: 18-19), the holin and lysin genes, a larger proportion of monocin remained in the cell pellet fraction rather than in the supernatant of the culture as compared to monocin production from *B. subtilis* producer strain sGL-064 (Table 5).

TABLE 5

Spot assay of monocin produced in holin/lysin+ vs holin/lysin− recombinant strains.

| *B. subtilis* producer Strain | # serial diluted Spots: Cell Pellet | # serial diluted Spots: Supernatant |
| --- | --- | --- |
| sGL-064 | 1 | 3 |
| sUC-001 | 4 | 1 |

Example 4

Changing the RBP (Seq Id No: 17) of Monocin 35152 to that of Monocin 33090 (Seq Id No: 27)

This example illustrated that changing ("RBP switching") the natural RBP (ORF 0140, SEQ ID NO: 17) of monocin 35152 to that of monocin 33090 (SEQ ID NO: 27), an RBP heterologous to monocin 35152, changed the bactericidal spectrum of monocin 35152 to that of monocin 33090, now a non-natural monocin called monocin 35152-33090 (see FIG. 1C).

Based on both the position of ORF 140 (the last open reading frame of the structural genes and immediately preceding the lysis genes) and its sequence similarity to that of listeriophage tail fibers, it was speculated that this could be the RBP that determines the bactericidal spectrum of the monocin. To determine this, ORF 140 of 35152 (SEQ ID NO: 17) was replaced with that the equivalent ORF140 of *Listeria innocua* 33090 (SEQ ID NO: 27).

The *L. monocytogenes* 35152 gene cluster encoding from ORF 125 to ORF 139 (SEQ ID NOs: 2-16) was PCR-amplified using primers oGL-054 and oGL-075. The RBP gene from *L. innocua* strain 33090, ORF 174 (SEQ ID NO: 27), was PCR-amplified from genomic DNA using primers oGL-076 and oGL-083. These two PCR products were then used as template in an overlap PCR reaction to fuse ORF 125-ORF 139 (SEQ ID NOs: 2-16) from *L. monocytogenes* with ORF 174 (SEQ ID NO: 27) from *L. innocua*. For the overlap PCR, primers oGL-054 and oGL-077 were used. This PCR product was digested with AscI and NotI and ligated into vector DG630 which had also been digested with the same restriction enzymes. This construct was named pGL-033 (Table 3).

Figure 3:
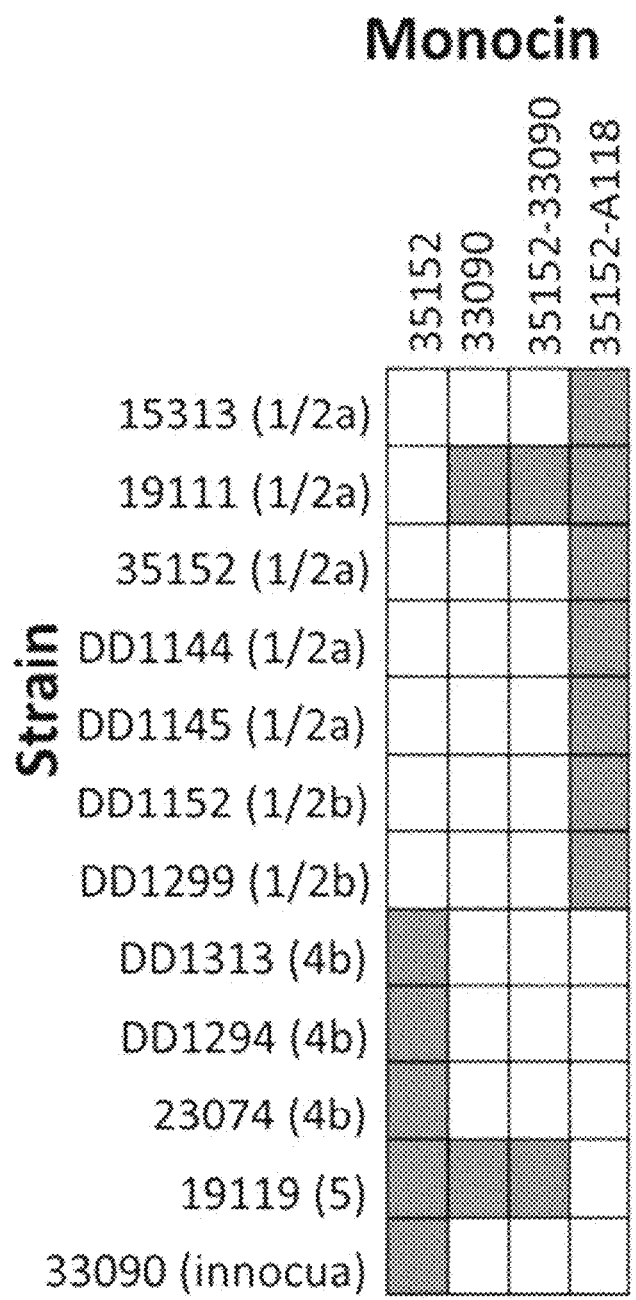
FIG. 3. Bactericidal spectrum chart of the activities of natural monocins 35152 and 33090 and non-natural monocins 35152-33090 and 35152-A118 against the indicated target strains. Shaded squares indicate bactericidal killing. Clear squares indicate insensitivity.

Integrants were made from BDG9 as above, resulting in strain sGL-068. A spot assay showed that monocin purified from the *B. subtilis* monocin producer strain sGL-068, expressing 35152 ORF 125-ORF 139 with 33090 ORF 174, has a different spectrum than the wild-type monocin 35152 produced by *B. subtilis* strain sGL-064, validating that changing the RBP gene altered the bactericidal spectrum of the monocin. The monocin with a heterologous RBP, a native ORF 174 from *L. innocua* 33090, instead of the natural RBP, ORF 140 from *L. monocytogenes* 35152, expressed with the 35152 monocin scaffold is termed monocin 35152-33090. Monocin 35152-33090 killed *L. monocytogenes* strain 19111, (FIG. 3) which is a target for natural monocin 33090 and not killed by the natural monocin 35152. Thus changing just one ORF (ORF 174, encoding a native RBP) was sufficient to change the bactericidal spectrum of monocin 35152.

Example 5

Expression of Monocins from an Inducible Promoter

This example illustrated the generation of a polynucleotide containing a monocin gene cluster and operably linked to a heterologous inducible promoter, that is a promoter not found naturally in association with a monocin gene cluster.

To generate a version of DG630 with an inducible promoter regulating the expression of the monocin genes, the *B. subtilis* Phyper-spank (IPTG-inducible derivative of spac system SEQ ID NO: 28) (openwetware.org/images/a/al/Phs.doc) along with the gene lacI was PCR-amplified from plasmid DG481 (Gebhart et al., 2012) using primers oGL-084 and oGL-085. The PCR product was digested with AscI and NotI and ligated into vector DG630 which had also been digested with the same restriction enzymes. This construct was named pGL-034. The monocin gene cluster, from ORF 128 to ORF 140 (SEQ ID NOs: 5-17), was PCR-amplified using primers oGL-086 and oGL-087. The PCR product was then cloned into a HindIII-digested pGL-034 using Gibson assembly (New England Biolabs). The manufacturer's standard protocol was used. This construct was named pGL-036. After integrating into BDG9 the resulting *B. subtilis* strain was termed sGL-071.

Monocin was produced from sGL-071 upon addition of isopropyl β-D-1-thiogalactopyranoside (IPTG) to the culture. Starter cultures of monocin producer cells were grown in 5 ml TSB media with 5 µg/ml chloramphenicol in a 15 ml culture tube at 28° C. with 250 RPM shaking and allowed to grow overnight (14-20 hours). This was then diluted 1/200 in 200 ml of TSB, 5 µg/ml chloramphenicol, at 28° C., with 250 RPM shaking for good aeration. When the $OD_{600}$ reached 0.2, IPTG was added to a final concentration of 50 µM to induce monocin production. Incubation continued for an additional 14-20 hours. Cells were recovered by centrifugation at 6000×g for 20 min. The culture supernatant and the cells were both saved and processed since there was some "leakage" of monocins into the supernatant.

The culture supernatant was processed by ultracentrifugation at 90,000×g for 3 hours. These ultracentrifuged pellets were resuspended in 1 ml of TN50 buffer. The cells were resuspended in 10 ml of TN50 with 1 mg/ml lysozyme and 250 units of benzonase and then sonicated using a BioLogics Inc. model 300 V/T homogenizer with a microtip. Three 30 s pulses at half power was sufficient to release PTLB particles. The homogenized material was then centrifuged at 23,000×g to remove debris. Monocins were recovered from the supernatant by ultracentrifugation as described above for the culture supernatants. In an experiment in which no IPTG was added to the culture, no monocin activity was observed.

Figure 2:
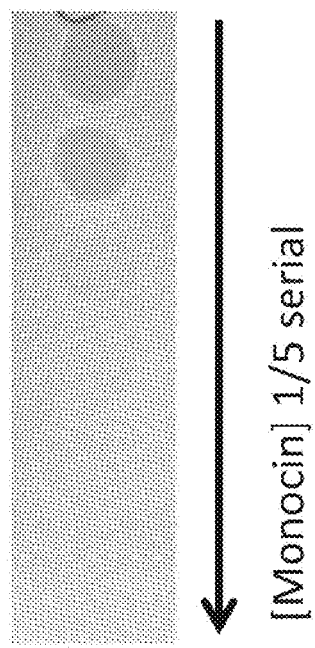
FIG. 2. Spot assay of the monocin 35152-33090 produced in B. subtilis strain sGL-075. This non-natural monocin gene cluster is under transcriptional control of the Phyper-spank promoter. The target bacterium is L. monocytogenes strain 19111.

A construct was also made to drive the recombinant monocin 35152-33090 from this same heterologous, inducible promoter. The entire *L. monocytogenes* 35152 ORF 128-ORF 139 (SEQ ID NOs: 5-16) with the heterologous RBP from *L. innocua* 33090 ORF 174 (SEQ ID NO: 28) was PCR-amplified from plasmid pGL-033 using primers oGL-086 and oGL-089. The PCR product was then cloned into a HindIII-digested pGL-034 using Gibson assembly (per the instructions of the kit manufacturer, New England Biolabs). This construct was named pGL-038. The resulting BDG9 integrant was termed sGL-075. FIG. 2 shows spot assay data of monocins produced sGL-075 upon induction with IPTG.

Example 6

Generation of a Non-Natural Monocin Using the RBD of a Tail Fiber of Listeriophage A118

This example illustrates the generation of a non-natural monocin having an altered bactericidal spectrum as the result of using an RBD from a phage to create a heterologous RBP.

As provided herein, it was found that it was possible to alter the bactericidal spectrum of a PTLB by making fusions with a portion of a natural RBP and a portion of an RBP of bacteriophage. The N-terminus of RBP protein was required for attachment of an RBP to the cognate baseplate of the monocin scaffold, while the C-terminal portion of the RBP, that is the RBD, interacted with a receptor on the target cell surface. Polynucleotide constructs were designed to fuse the portion of ORF 140 (SEQ ID NO: 17) encoding amino acid positions 1-40, for example, with the portion of the tail fiber ORF 2345 (SEQ ID NO: 21) of listeriophage A118 encoding amino acid positions 210-357. Four short ORFs (2344, 2343, 2342, and 2341, respectively SEQ ID NOs: 22-25) located immediately distal to the A118 tail fiber gene were also included.

The monocin 35152 gene cluster from ORF 128 through to the 5' portion of ORF 140 was PCR-amplified using primers oGL-086 and oGL-112. The A118 phage tail fiber gene (SEQ ID NO: 21) was PCR-amplified from phage genomic DNA using primers oGL-120 and oGL-103. These two PCR products were cloned in a three-piece assembly with HindIII-digested pGL-034 using Gibson assembly. This construct was named pGL-045 and was comprised of a polynucleotide encoding amino acids 1-40 (BPAR) of SEQ ID NO: 17 and amino acid positions 210-357 (RBD) of SEQ ID NO: 21 plus SEQ ID NOs: 22-25. The resulting *B. subtilis* integrant was termed sGL-092. The entire gene cluster was under transcriptional control of the Phyperspank promoter. The monocin with its heterologous RBP harvested from this monocin producer strain, sGL-092, had an altered bactericidal spectrum compared to that of the wild-type monocin 35152, demonstrating that an RBD of a phage tail fiber fused to an amino terminal portion, that is a BPAR, of a natural RBP, generated a monocin with a heterologous RBP and possessed an altered bactericidal spectrum determined by the heterologous RBD of the resulting heterologous RBP.

Monocins produced from sGL-092 had a bactericidal spectrum distinct from natural monocin 35152. (FIG. 3, monocin 35152-A118), and targeted several *L. monocytogenes* 1/2a strains not susceptible to either monocin 35152 or any other tested natural monocin.

Example 7

Increasing the Level of Expression of a Monocin by a Monocin Producer Cell

This example discloses a means to increase the level of expression of a monocin by a monocin producer cell.

To improve the yield of the monocin 35152-A118, new monocin *B. subtilis* producer strains were generated in which the four short ORFs 2344, 2343, 2342, 2341 (SEQ ID NOs: 22-25) that were located just downstream of the A118 tail fiber gene of monocin 35152-A118 were removed one-by-one from the monocin 35152-A118 construct. It was speculated that one or more of these ORFs could affect the production of monocins. *B. subtilis* strain sGL-153 included only three of the downstream ORFs, 2344, 2343, and 2342, respectively SEQ ID NOs: 22-24. *B. subtilis* strain sGL-154 included only two of the downstream ORFs (2344 and 2343, SEQ ID NOs: 22-23). *B. subtilis* strain sGL-155 included only the first downstream ORF, 2344, SEQ ID NO: 22. These monocins with heterologous RBPs harvested from these *B. subtilis* monocin producer strains were spotted on a lawn of target strain *L. monocytogenes* 19111. The data showed that removal of downstream ORFs 2341 and 2342 (SEQ ID NOs: 24-25), but inclusion of ORFs 2343 and 2344 (SEQ ID NOs: 22-23) in the monocin 35152-A118 gene cluster greatly improved the activity yield.

Example 8

The Demonstration that Monocins are Bactericidal at Cold Temperatures

This example demonstrates that monocins are bactericidal under cold temperatures.

Figure 4:
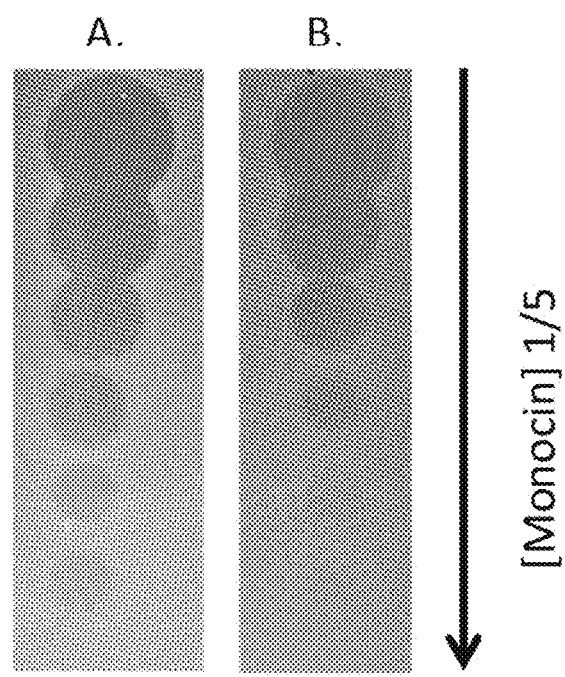
FIG. 4. The results of assays showing the bactericidal activities of monocins at 3-4° C. Lawns of target L. monocytogenes bacteria were chilled to 3-4° C. and spotted with chilled preparations of monocins and then incubated at 3-4° C. for 3 days before imaging. Lane A is L. monocytogenes strain 23074 spotted with monocin 35152 and Lane B is L. monocytogenes strain 15313 spotted with monocin 35152-A118. Clearing in the lawn indicated bactericidal activity.

To determine whether monocins can kill their target strains in the cold, a spot assay was conducted using monocin 35152 isolated from monocin producer *B. subtilis* strain sGL-071 and monocin 35152-A118 isolated from monocin producer *B. subtilis* strain sGL-154. Once a lawn of an appropriate target *L. monocytogenes* strain for each monocin was poured, the plates were chilled to 3-4° C. Monocin dilutions were made and also chilled to 3-4° C. prior to spotting. The chilled monocin dilutions were spotted onto the chilled agar plates. The plates were then incubated for 3 days at 3-4° C. The spot assays show that both monocin 35152 and monocin 35152-A118 can kill their respective target strains in the cold (FIG. 4).

Example 9

The Product of A118 Gene 2344 is a Tail Fiber Assembly Protein Required for Optimal Production of Monocin 35152-A118

Many bacteriophage or PTLB RBPs require an accessory protein or chaperone for proper assembly of the tail fiber in order to get optimal active bacteriocin. This example demonstrates that monocin 35152-A118 requires the phage A118 gene 2344 product for this purpose.

Just downstream of the gene encoding tail fiber RBP of bacteriophage A118 are three small open reading frames, ORFs 2344, 2343, and 2342, followed by the genes encoding holin (SEQ ID NO.:025) and lysin. To determine whether any of these ORFs encoded necessary tail fiber assembly proteins, four 35152-A118 monocin expression constructs were generated, using the same methodology as described in example 6, as set forth below.

Briefly, the 35152 monocin gene cluster, ORF 0128 through to the 5' portion of ORF 0140, was PCR-amplified using primers oGL-086 and oGL-112. The A118 phage tail fiber gene was PCR-amplified from phage genomic DNA using forward primer oGL-120 and reverse primer oGL-162, oGL-163, oGL-164 or oGL-165 to include three, two, one, or no downstream chaperone(s). The monocin PCR product and each of the A118 PCR products were cloned in a three piece Gibson assembly into HindIII-digested pGL-034. These constructs were named pGL-075, pGL-076, pGL-077, and pGL-078. The plasmids were integrated into strain A8. The resulting integrants were named sGL-364, sGL-158, sGL-365, and sGL-366, respectively.

Figure 5:
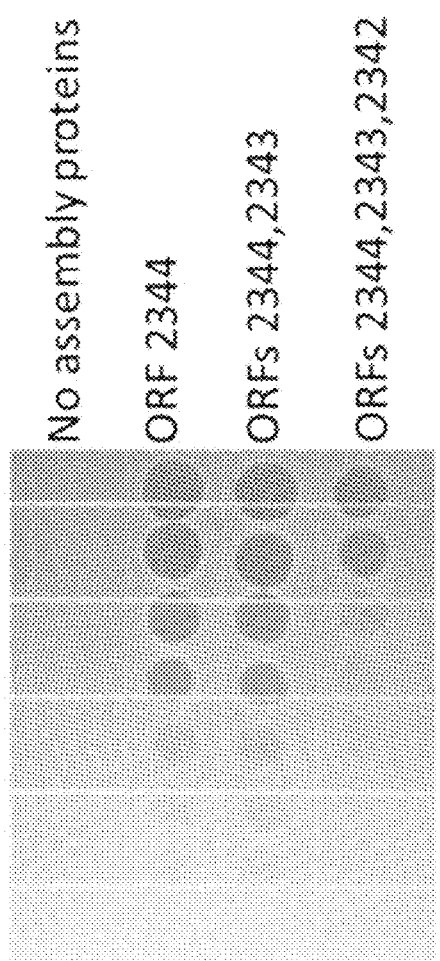
FIG. 5. Spot tests of monocin 35152-A118 produced in constructs including various combinations of putative tail fiber assembly or chaperone genes. If no putative tail fiber genes were present, no active monocin was produced. The inclusion of ORF21 resulted in robust activity which was equal to the activity of the monocins produced with both ORFs 21 and 22. Having all three putative tail fiber assembly proteins was actually detrimental.

One construct included all three putative assembly proteins encoded by ORFs 2344, 2343, and 2342; SEQ ID NOs: 024, 023, 022, respectively), another construct included just 2344 and 2343, another construct included just 2344, and a final construct had none. These were each separately expressed in *Bacillus subtilis* and the resulting monocins were assayed for activity on strain 19111. The construct that had no putative tail fiber assembly proteins gave no active monocin particles. The construct that included expression of ORF 2344 produced robust activity. The construct that included 2344 and 2343 gave monocin yields and activity nearly identical to the construct that had just 2344. The construct that included all three putative tail fiber assembly proteins actually yielded slightly less monocin activity. See FIG. 5. From this data, it was concluded that the gene product of ORF 2344 (SEQ ID NO.: 022) is a tail fiber chaperone required for production of monocins and was the only such tail fiber assembly or accessory protein needed.

Example 10

Improved *Bacillus Subtilis* Production Strain for Monocin Expression

Figure 6:
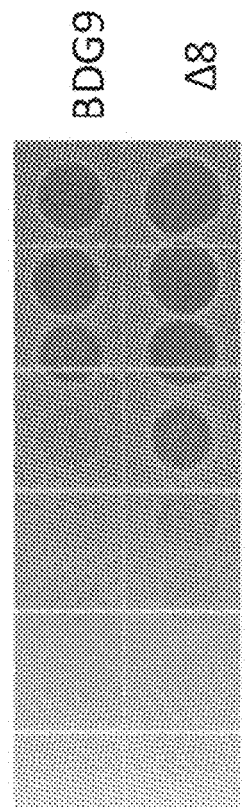
FIG. 6. Comparison on monocins produced in the Δ8 strain vs BDG9.

To further improve monocin yields, a modified *B. subtilis* production strain deleted of prophage genes, sporulation functions, and flagella synthesis, was constructed. *B. subtilis* strain Δ6 was used, which had a series of prophage element deletions including prophage 1, prophage 3, SPβ, PBSX, and Skin (Westers et al). Strain Δ6 was further modified by deleting flagella production (Δhag) and sporulation (Δspollga) to generate strain Δ8. The M35152 gene cluster, minus holin/lysin, was transformed/integrated into Δ8, regulated with P$_{hyper-spank}$ upstream of ORF 0128, as in sGL-071. The resulting strain sGL-157 (M35152) had improved monocin production (typically 5-10 fold) over BDG9-based counterpart. See FIG. 6.

The methods used to produce this strain are detailed as follows. *Bacillus subtilis* knockouts were made following the methods described in Tanaka et al. (Tanaka K, Henry C S, Zinner J F, Jolivet E, Cohoon M P, Xia F, Bidnenko V, Ehrlich S D, Stevens R L, Noirot P. 2013. Building the repertoire of dispensable chromosome regions in *Bacillus subtilis* entails major refinement of cognate large-scale metabolic model. Nucleic Acids Res. 41:687-699). Strain Δ6 was described by Westers et al. (Westers H, Dorenbos R, van Dijl J M, Kabel J, Flanagan T, Devine K M, Jude F, Seror S J, Beekman A C, Darmon E, Eschevins C, de Jong A, Bron S, Kuipers O P, Albertini A M, Antelmann H, Hecker M, Zamboni N, Sauer U, Bruand C, Ehrlich D S, Alonso J C, Salas M, Quax W J. 2003. Genome engineering reveals large dispensable regions in *Bacillus subtilis*. Mol Biol Evol 20:2076-2090) and is a prophage deletion strain. In order to manipulate strain Δ6 further, the cat gene, which was a remnant from the original pks operon knockout, was removed. First the upp::kan marker was amplified from *Bacillus subtilis* strain TF8A λPr-neo:Δupp with primers oDG1013 and oDG1014. The PCR product was cloned into pETcocol linearized with NotI. This plasmid was then linearized with SpeI and transformed into Δ6 and selected for kanr. This strain was termed BDG243. To delete the cat gene, the phleomycin cassette was amplified from pUC18 phleo cassette (Tanaka et al.) in a sewing PCR reaction with two flanking regions from Δ6 using the primers oDG1001 and oDG1002, (left flank) oDG999 and oDG1000 (phleomycin cassette), oDG1003 and oDG1004 (right flank) and the three pieces combined by amplification with the two outside primers oDG1001 and oDG1004. This PCR product was transformed into BDG243 and selected on phleomycin plates followed by screening for kanamycin sensitivity. This strain is designated BDG247. The phleomycin marker was deleted by growing BDG247 in LB without selection for 4 hours, plated on kanamycin, and colonies picked and screened for phleomycin sensitivity. This strain, BDG252, was a markerless knock-out strain, useful for making further modifications. To delete hag, the 5' flanking region of hag was amplified with primers oDG1019 and oDG 1020, the 3' flank amplified with oDG1021 and oDG1022, and the pleomycin cassette amplified with oDG999 and oDG1000. The three PCR products were combined and a sewing reaction performed with oDG1019 and oDG1022. This product was transformed into BDG252, selected on phleomycin, and then screened for kanamycin sensitivity to create BDG253. The phleomycin marker was again deleted by growing BDG253 in LB without selection for 4 hours, plating on kanamycin, and screening colonies for phleomycin sensitivity to create strain BDG255. To delete spoIIga, the 5' flank was amplified with primers oDG1023 and oDG1024, the 3' flank amplified with oDG1025 and oDG1026, and the phleomycin cassette amplified with oDG999 and oDG1000. The three products were combined in a sewing reaction using primers oDG1023 and oDG1026. After transformation, selection on phleomycin, and screening for phleomycin resistance, the resulting strain was named BDG256. The phleomycin marker was deleted, again by growing BDG256 in LB without selection for 4 hours, plating on kanamycin, and screening colonies for phleomycin sensitivity to create strain BDG257, also known as the Δ8 strain.

Example 11

The Spectrum of Monocin 35152 and 35152-Δ118 Encompass Important Foodborne Serotypes Most human illness caused by *Listeria* in North America is caused by two predominant serotypes, 1/2a and 4b (Nelson, K. E., D. E. Fouts, E. F. Mongodin, J. Ravel, R. T. DeBoy, J. F. Kolonay, D. A. Rasko, S. V. Angiuoli, S. R. Gill, I. T. Paulsen, J. Peterson, O. White, W. C. Nelson, W. Nierman, M. J. Beanan, L. M. Brinkac, S. C. Daugherty, R. J. Dodson, A. S. Durkin, R. Madupu, D. H. Haft, J. Selengut, S. Van Aken, H. Khouri, N. Fedorova, H. Forberger, B. Tran, S. Kathariou, L. D. Wonderling, G. A. Uhlich, D. O. Bayles, J. B. Luchansky, and C. M. Fraser. 2004. Whole genome comparisons of serotype 4b and 1/2a strains of the foodborne pathogen *Listeria monocytogenes* reveal new insights into the core genome components of this species. Nucleic Acids Res. 32:2386-2395. Accordingly, the bactericidal activity of monocins 35152 and 35152-Δ118 were tested against a panel of independent *Listeria* isolates. See Table 6. Monocin 35152 killed 4b strains, whereas monocin 35152-Δ118 killed 1/2a strains. Therefore, a biocontrol agent that includes monocins 35152 and 35152-Δ118 may be used to kill these foodborne pathogenic strains.

TABLE 6

Bactericidal activity of the monocins on a panel of *Listeria* strains.

| Strain | Other designation | Source | Serotype | Sensitive to M35152 (recombinant) | Sensitive to M35152-Δ118 |
|---|---|---|---|---|---|
| 15313 | | ATCC | 1/2a | No | Yes |
| 35152 | | ATCC | 1/2a | No | Yes |
| 19111 | | ATCC | 1/2a | No | Yes |
| DP-L4056 | 10403s phage cured | Dan Portnoy | 1/2a | No | Yes |
| DP-L3633 | EGDe | Dan Portnoy | 1/2a | No | Yes |
| DP-L3293 | LO28 | Dan Portnoy | 1/2c | No | Yes |
| DP-L3817 | 1993 Halifax | Dan Portnoy | 1/2a | No | Yes |
| DP-L1171 | | Dan Portnoy | 1/2b | No | Yes |
| 23074 | | ATCC | 4b | Yes | No |
| DP-L185 | F2397 | Dan Portnoy | 4b | Yes | No |
| DP-L186 | ScottA | Dan Portnoy | 4b | Yes | No |
| DP-L188 | ATCC 19113 | Dan Portnoy | 3 | No | No |
| DP-L1173 | | Dan Portnoy | 4b | Yes | No |
| DP-L1174 | | Dan Portnoy | 4b | Yes | No |
| DP-L1168 | | Dan Portnoy | 4b | Yes | No |
| DP-L1169 | | Dan Portnoy | 4b | Yes | No |
| 19119 | ATCC (*ivanovii*) | | | Yes | No |
| 33030 | ATCC (*innocua*) | | | Yes | No |

Example 12

Figure 7:
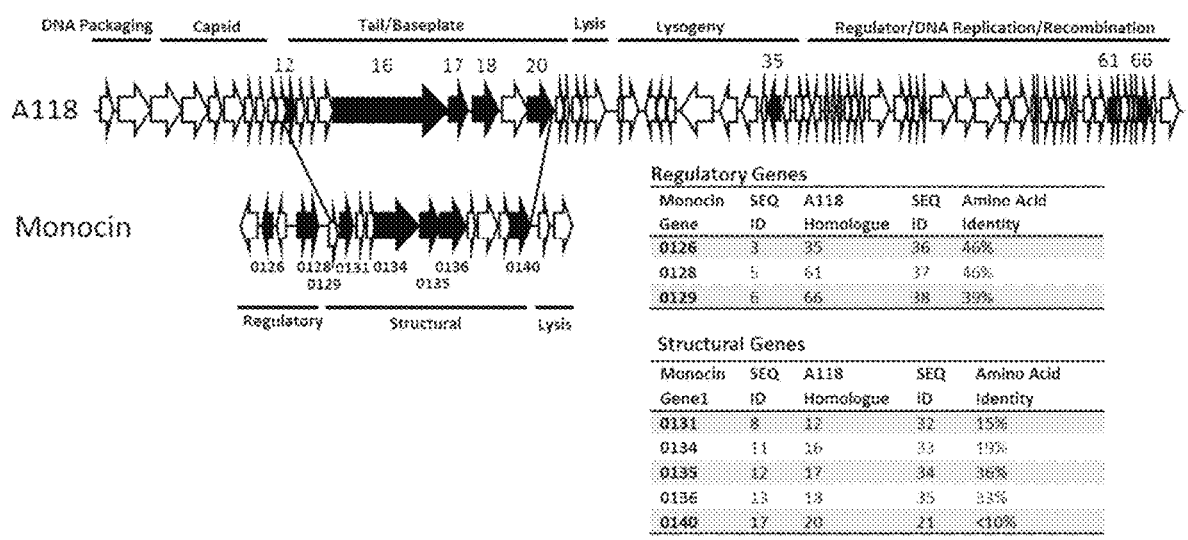
FIG. 7. Comparison of the monocin gene cluster to the genome of the TP901-1-like phage A118. The genes that are similar are colored black. Three regulatory genes of the monocin cluster (0126, 0128, and 0129) were homologues of regulatory genes of phage A118. Five of the monocin major structure genes (0131, 0134, 0135, 0136, and 0140) were also A118 homologues.

Monocins are High Molecular Weight Bacteriocins with Tp901-1-Like Tail Structures All high molecular weight bacteriocins described to date have been related to either contractile Myoviridae-like structures (R-type) or Lambda-like tail Siphoviridae structures (traditional F-type). Monocins were shown to be F-type bacteriocin based on a lack of a contractile sheath protein and electron microscopy. However, as shown herein, monocins were determined to be closely and specifically related to the tail structure of phage Δ118, a TP901-1-like phage (Cambillau, 2015). Comparison of a monocin major tail protein (SEQ ID NO.: 8) to those of TP901-1-like phages (SEQ ID NOS.: 30, 31) including Δ118 (SEQ ID NO.: 32), and comparison of monocin tape measure protein and baseplate proteins (respectively SEQ ID NOs.: 11, 12, 13) to those respective proteins of phage Δ118 (SEQ ID NOs.: 33, 34 and 35), indicated that monocins as described herein were structurally TP901-1-like. In addition, three monocin regulatory proteins (SEQ ID NOs.: 3, 5 and 6) were shown to have Δ118 homologues (SEQ ID NOs.: 36, 37, 38). A comparison of protein sequences encoded by the monocin gene cluster to those encoded by the Δ118 genome is shown in FIG. 7. Thus, monocins fell into a unique class of TP901-1-like high molecular weight bacteriocins.

TP901-1-like phages have a distinct baseplate structure wherein the receptor binding protein (RBP), a homotrimeric protein, is arranged in six groups with three "tripods" each (see Bebeacua C, Tremblay D, Farenc C, Chapot-Chartier M P, Sadovskaya I, van Heel M, Veesler D, Molineau S, Cambillau C. 2013. Structure, adsorption to host, and infection mechanism of virulent lactococcal phage p2. J Virol 87:12302-12312; Collins B, Bebeacua C, Mahony J, Blangy S, Douillard F P, Veesler D, Cambillau C, van Sinderen D. 2013, Structure and functional analysis of the host recognition device of lactococcal phage tuc2009. J Virol 87:8429-8440; and Cambillau C, 2015, Bacteriophage module reshuffling results in adaptive host range as exemplified by the baseplate model of listerial phage A118. Virology 484: 86-92).

This results in a total of 54 RBPs per phage particle (3×3×6). R- and F-type bacteriocins are known to possess just six copies of single homotrimers (18 total copies). This is the first example of a TP901-1-related structure capable of functioning as a high molecular weight bacteriocin.

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

Although the invention has been described with reference to the above example, it will be understood that modifications and variations are encompassed within the spirit and scope of the invention. Accordingly, the invention is limited only by the following claims.

```
Listeria monocytogenes strain 1/2a 35152
Motiocin gene cLUster (wild type)                                    SEQ ID NO: 001
TTATCTGGTTAATAAGCCGTTTCCGGTTTGAAAACTATCTACTTGATCGAGTAGATTC
TCGTGCGAGCTAATGGTGATGGGCTTTTTGGAAAGCAGTAGTCCGCTTTCCCGTAAT
TCTTCTAACACTTCAGTTACTCTAGCTCGACTCGAACGACAATAATCAGCTAAGAAC
GTTTGCGTGAcATAGACTGGAAGCTCAATTGAGCCTTCTGTTTGATGCAAATGAAGT
AGCTCAATAATTICCACCAAAATACGCGTTACTTTGACTATGGGTGCTTGATTAATA
TTCTTGTAATTTTTTGATGTAAATAAATATCTAACAATAACTTCATCAAGTATAAGAT
GGAAAAATTGTGGATTTGCATATAAATAATTGAGAAGAAACTCGCGGTCAATAAAT
AGAACGGTACCGTTTTCTAATGCGCGAACACGGTATTCAGTAAGTTCgGGCGCTGTT
TTTGTTTCGAGTAAACTTTCCATTCCAAAAAGCGCGTGTTGACCAATCAACGCATTT
ATCATCCAGCGGCCTTCATTTGTAGGACCTTCTAAAACAGCCtTTCCCTCTAAAATAG
CACCTATTTGCGGCGCCTTTTCTTCGTAATCTCTATATGAATGAATAATTTCTCCTTTT
TTAAAAGAAATTTTACTTGAATAATCACTAGAAAAAATATCTGAAAAATCTATCGTG
TGAAGCATTATCAAACTCCTATACTAAGGTAAAATTGGTATTTACCATATTACTGT
ACTGCTATTTGTGtCAAAAAGATACCGAATAAAAATCGTGTTCACAATTTAGACATG
AAAAAGTCACTTTTTAGCAACAATTTTAGTGATTTTATCAATAAAAACTTACTTTTTC
TTCCCTGGAGAGATATCCAACCAAAAAAAGACCCTCCgTAGATAGGAGAGTCTTTCA
AAACTTCTTGTAAACATCAATGGAATTGCCAAAATTAATGAAATATCCACCATAATC
ATACATTGGACCATATTTTTCCGCGTAATGAGAAACTGTATGGCGCAAAAATTCTTC
TGTTACCTCTAAAAACTCCGCTACTTCAAAATATTCTCGTAAGCCTAGATAAAAACA
AGCAATGATGTCATCAAGcGGTATTAGTTCCTCATAACCTTTGCGACGAGCGAAAAT
TTCTTGTTTTTATCCATGATTGTTTCCTGTTTGGTGATATTACCTACAGTGTATTTGT
AATGCATCAATTCTTCTACTAAAACACAGCCTTTTTCAATGGAAGATTGATCCTTACT
AATAAAAATCATCCCATTTAAATAAAGTCCCGGAAGTTTGTAAGGCATTTTCTCTTC
TCTGATTGTTACCTCATCTTGGTATTTATTTACCAATTTTTCGTACAATAAAATCACA
TCCCGCGATGGAGTTTTTTCTTCATCTCTATATAAGCTAAAATATCCCGCATTTCTTC
CTCGGTTACGTCATCATCAATATGGGCTGCAATTGTTACCAAGCGTTCATCAACAGG
GGGTAAATTCTTTCAGGAAAAAAGTCATCTAATCGTTTGTTGAAGATTTTTGCAAG
TTCAAATAAAACATCTTGATTTGCTTTTCGATCACCATTTTCATAACGGCTAATAGTT
TGGCGAGTTGTATGAAGCTTTTCTGCTAATGCTTCTTGATTTAAGCCTCGTTCCTCGC
GATATTGTTTTATTTTATTTCCTACAAATTTATTTAGCTCCATAATAATTGTCCTCCAT
ATGTTTATGGCTTCAGTATAGCACTTTTAGCACCAAAACGGAACTTTTTCGAACATA
TTTGTCGGATAAAGTTTACCAGTAACCAAAATGGTGCTATAATATTTGTAGAGCTAG
AAAATAAAtGCGGCTGATTTTGCACcGATAGCACCGAATcGGTGACAAaaCTAcTATAT
TAATTTATGAGATGGAAGTGGGAATGGATGGATAGAAAACTTTTAAAAGAAAAGCA
AATCCAACTAATTTTTCAACTAGAACAAGAAGAAAATCGATTTATTCGAAAGCGTTT
GATAGAAGAGTTGGAGTTTTTTGAAGCACTTGGGGATAGGGAAAAAGGACTTCTAA
CGGCGGAGCAAAAGTTGCTTATTTTAaCACCTAGTGAGTACCGAGAATACAAAAGAA
CCAAATCAGATGTGCAAATTAGTAGGATAATTGGAGTATCGAGATCGTCACTTGCAG
```

-continued

```
AATGGAAaCGAAAAAAAGGTTTAAATAGAAAAAAGTCGCAACCGGTTCAGCAGGAA
ATGATTGATGTATTAGCTTTTCATTTAGATAAAACAAAAGAAGAAATTGGCGCTTTA
CCTGCTTCGGCGATTGAATGTCAGTATGAGGCTTTTGTGATTAATGAAGCCAATAAT
TAAGGAGTGATAAAATGCAGGTTTTAGTTTTACCAGAAAATAAGGATATCAATTATA
TAAAAACGGTCCAtGAAGTAAAACGATTTTTTGCGGATTTCGAGAGATTTCGGATGA
TTACGGGGTTATCAAAAAAGCCACATTTACTTAGAAATGGTTTTCTGGAAGAGCCGC
AGTTTGAGCCGGTAGCATTTTCTGCTAGACATAATAAAGAgGTCATTTTGGAAGCGC
GATGGTTGGTAGAGAAATATACTGAAATGTTGAATCAGATGGATGATTTATATCGAA
GATGGTTGGTAGAGAAATATACTGAAATGTTGAATCAGATGGATGATTTATATCGAA
CTATTTTGATGGAATGTTACGTGGAACGAAAACAAGATGTGGCGGTAATGATGGATT
TACCGTATGAAATTGCCCAGTTTAAACGGATAAAAAAACGgGCAGTGCTAGAACTTG
CAACGCTAATGGGAATTTTAGTAAGGAAATGATGATACTTTCGTGATATTTTGAAAC
ATCATTTTCCTATTAATATAGAAGTAAGCTAATTGTCCAGTAAGCGGATGACAATAA
AAGCTGCATCAGAATGAAGGTGCACCGATTTTCTGATAATACATGATGTTTTACAAG
AAATTTGTTTTTATGATTGGATTTAAATCCGTTGAGATAAACAAATATTCTATTTTGG
AAAGTAAAGTTCGGAGGAATAAATTATTAAATGTGGTCTTGACCGAACTTTGCTTTC
TGTTTTAAAGGAGTGAACGCTTGGTGAAGAGTTTGAGCTTCATGAGAGTTTTGGAAG
CAGTGAGAAcAATGCTCCAGGAAAAAGGCGGACTAGATGTTTCTATTGTAATGCGTa
ACCAAGTGGAAATGCCTACAACGATGATCGAGATGATTGATCAAGAGGAAGAAGAA
AGCCAAACTGCCTGGAAAGAAAAATACCGTTTTGCtATaCATCATTATACAAATGAAc
aGGACtTAGCGGGgGTCGAgAAGATtGATACGCTTATCCAAAtgGGtTTCATtTTTGCCcGA
gGGATACAAATTAgTCGCaGTTCGACATTgtGGAAAACAAAATTTAGTCAAAGAAAAT
ACGTTAATTCACGCAAAAACCAGTTTTGAAGTAAGTATTTGTCGTGAgTTAAAAGTA
AAAATTTAGGGGGAAATATTAATGGCATTTGAAGAGAATTTATATTGTGATTATACA
CCGGGAGCTGCTAAAGCGGTCGCGGGGAAAGATGTAATTTTAGCAGTTTTTAACGC
AGCGGGGGAtAAACTATTgGCtGTTGCGGGCCAACAAGGTCTgACTGTAAACCGTTCT
AAAGATAGtATTGAAATTACATCcAAAGATACAGTgGGCGGATGGAAATCCAAAATT
GGCGGTATGAAAGAATGGTCAATTGAAAATGACGGgTTATATGTCGCTGATGCAGA
GTCTCACAAAGAATTGGCGAAATATTTCGAAAGTGATAGCCCAGTTTGcGTGAAAAT
CATTAATCAAGCATCTAAAAAAGGTCTTTTCGGTGGTTTGGCAATTGTAGCTGACTA
TAGTTTTGAAGCgCCTTTTGATGAAGCGATGACTTACTCTGTAAAACTAGACGGAAT
GGGCGCGCTTGTTGATTTAACGATTACTGAGGGCGGCGACCAAATGCCCGGCAAA
CACCTGTAGCACCAGCAGAATAAAATAGAAAGCCACTGAAATAAGTGGCTTTCtCTT
AGGAGGAAAATAAATGTTTGAAGTGAATGATACAACTTATATTTTACGATTTAATAA
ACAAAAAGTTAAAACGGTGGAATTAACATCAGGGATTAGTTTAGTTGCAGCTTTGAC
TGCGAATAAAGGGATTTTGAGCTATCAAGTGATTGAAACgCTATTTGTTTCAGGACT
TGTGGAAGAAAAAGGCTTAGTACCTGTAAAACAAAAAGAAGCcTTGGAGATTTTCG
ATAAATTAGTAGAAGAACAAGGCTTAATTTCcCTTAATGTAGCTGTTATTGAGAAAT
TGCAAGAGGATATGGGTTTTTTTGTTCCGTTAAAACAGATTGAaTTTGAGTATTTTGGT
GCTGAGGACGAAGAAGTGGATAGTGAAATGAACCATGATTTtGATTTGGAAAAACAg
TTcGCTTTTTTTGTAGTcAATTTTCAaATGTCCAAGCATGATTTTGAAGAACTTACTGA
AGTGGAGAAAAATTTCATCATGAAAGAATGGGAAAACAAGGTGATTTTTGAATCTA
CTATGCTTCGAAATGCAGTTTTAAATGCGGAACAAAATCTCAATCGAAAACGAAATT
CaCGTTTTATCGACTTGCATAAAAAACGTCAGAAGAAAGCCGATGTTAATTATACAG
TAAATGCACTTCAAGCAATTTCCGATAATGAAGCGAAGGAAGGTAAAGCGTGGATT
GATCGGATTTATGGTGCAAATGGGTTGCGAAGACCTAAAAaTAAAGAAGAAAGGGG
GAAAATGAATGGCGGAgTCTAAAAGTaTTACATTTGAACTgAACGAGAGCGTTTTAA
CAGCGCAAGTTGGCAGGCTAGATGAgATGGCGATGGTTGTAGAGCggCGgTTTTCAG
AGCTCAAAATGACTATTGAAGATGTTGGAAATGCTGATCCAGGTTCGAAAATTTCCG
AaTCTTTAGGTGGGCTGCAGTCTGGGCTTGGCACGATTAGTTCGGCGTTTGGACAGCT
GGGTTCTAGTAGTGAGGCGATTACATCcGGATTCGGTACTGCGGTTGGTTCTGTTGGT
GGAATCACGGATGCGTTTAAAAATCTAGGTTCAAGTGTGCAAAATGGTACGTTATTT
TCAAGCTTGGCgACtGGAATTGGTGGCATGAGTACgATGCTTGGTGGAGTATCTGGCG
GcGTTCAAGGAATTACAAATCTAGCTAGTGGATTTATGGAATTGAAGAATCATTTAG
GCGGTTTGATGTCTTCTATTGGCGGCGTTGGTGGAATTATGGGTAAACTGACTTCTCC
AATGGGGTTAGTAATTATCGGGATTGTTGCGCTAGTTGCTGCTTTTACGTACTTGATG
ACGACGAATGAATCGTTCCGAAATACCGTGATGTCAGTCGTAACGCAGGTTGCGCA
GTTGTTCGGGCAACTTGTCGCTAGTTTAATGCCGATTATTATGCAAATTGTTACTGCG
GTTATGCAAATTGGTGCCGCGTTAATGCCGATgGTTATGCAGTTTATTAGCTTTTTTG
CCCAGTTGTTAGCTCAATTAATGCCATTTATTAATATGCTGATTTCTATGCTTATGCC
TGTTATTATGCAGATTGTTCAAGTTGTTATGTCGCTTGTTTCAGCGTTATTACCAAGC
ATTATGACAGTGATCCAAGGCATTATGAGTGTTATTCAATTTTTAATTCCGATAATTA
TGCAAATCGCGACGGTGGTTGTACAAATTGTTGTAACGATTATTTCTTATATAAGTA
AAATTATGCCGATTGTtATGACGATTATTGGCGTTATTGTTTCGATTATCACaACGATT
ATTAGtTAcGTcGTTATTATTGCgACGACgATTGCtAGtGTTATTGGGAAAATTATTAGC
TTTATTGCgAGTGTTATTACgGCGGTTATCGGGATTGTGCAACCAATTATTGCCTTTAT
TACCAATATCTTTACGACTATCGTGACAATTATTGGTGCAGCTTTCCAAATGGTATTT
ACTGTTGCATCCAAAATTTGGAATTCCATTATGTCGACTATTTCCGGAATTATTGAcG
GAATCAAAGCAGTCATCACAGGTATTTCTACTACAGTTTCATCAGTGTTTAAcGGAG
TGAAGCGCATTATTACAGGTGTTTTTGACGGAATCAAAAGTGCTTGGGGTGGTTTAA
CTGATTTTGTgGGGAAATATTTTCGATGGTGTTTCAAgTGCAATTCAAACAGTGGTAGA
CAATGTCAAAGGTTTTGTAAACGTgGTAATTCGAGGgATTAATGGAGCCATTGGTTTA
ATTAATAAGATTCCAGGAGTTGAAATCGGCAAAATACCGCAATTAATTTCCGGAAC
AACAAATTTCCAAGGTGGCTTTGCTCGAATGAATGAAGGCGGCCGAGGTGAAATGG
TTGTTTTACCGTCTGGTTCTCAAGTAATTCCGCACGATGCAACGATGAAATACGCAA
GAGAAAGTGCGCGCGGAAATAAATCAATGCTITACACGAGTCAAGGCGCTGATTTG
GCTAGAGTTGAAAATCTTCTCGAGCGCTTACTACAAAAAAATCCTGTAATCAAAATG
GATGACAAAGTGGTAGCTGAGGTAGTTAGCCGTAATCAAGCTAACTCATTTGATCAG
TACAACTATACAATGGGAGGTGCAGCTTATTCATGAGtGACTTGTTTTTAGAATTAAA
TGGAAAAGTGCATTCGCTTAGTGAGACATTTCCAGGTCTTTCTGTACAAGAAGTTTC
GAGACAAAGTCCCCAGTTAAGCATGGAAACTGCTGAAATAGCTGGGACTGATGGGG
```

-continued

```
TTATCCCgGGAATGACCCAATTTAAACCGTTTATCTTTTCAGCAAAATGTAATTTGCA
AGCACTTGATATTCCaGATTAtCATTTGGCAGTCAGAGAAATTTATGAATTTTTATTTC
AACGGGATAGTTATTATATTTGGAGCGATCAAATGCCAGGAATTCGGTATGAGGTGC
ATCCTAAACCAGTTGATTTTAGTCGAGAATCGGATCGTGTTGGtTTACTCACTATAGA
ATTTGATGTAITTAAAGGCTATGCGGAGTCACGTGGCACGAGCCTTGACCCaATGAC
TTTTGAAGTGGATTTATGGCAgATGGGAATGAATTTATCGAACCGTGATGATTTATTT
TATGTTTTTAGAGAAAATACATTTCGGGTCTATAATGCGGGGAGCGACCGTGTTAAT
CCACTGATGCGACATGAATTgGATATTGCTATGACGGCGAATGGGACACCAACGATT
CATAATCTTACAACGGGAGAATCCTTCGAGTATCGGAAAGAGCTACAAAAAACAGA
TGTTTTACTGTTaAACAATATTTATCCACTTGTTAATAACCGcCGTGTTGGAAAAGAT
ACCAATCATGGGATTATCACCCTTGAAAAAGGCTGGAACGATTTTGAAATCAAAGG
TGTAACGGATGAACGATTGCTTTTAATTTTCCGTTCATTTATCGGTAGGTGATAGAT
ATGGATTATGTGATTATTCAAAGTATGGACAAAGAAGTGGAAGAGATTCTaACAGAC
AtTGATTACGGCTCCTTTTCCTACGATTATGAAAAAATACAAGTCGTGCTATtTCGTT
TACTGTGAAcAAAACGAAACAGAATGCAGCAATTTTTGACTTGGTAGGAAATGAAG
CAATTTTAACATATCAAGGGCAGCAATTTGTTATTAAAAAATGTACGCCAAATCTA
TTGGAGGAACAaTTTCAAAGCAGATTACGGCCCAGCATATTTGTTATACAGTGCAAG
ATCATGTGCAGTATAACGTGAAATCTGGACGAAAAAAATATTCGATTCAAACGGTA
TTGGAATTTGCGTTACAAGATAATGTACTAGGATTTTCTTATGAAATTCAAGGGAGT
TTTCCTTTAGTTGAATTAGAGGACTTAGGAAATAAAAATCTGCTTAGAGCTAGTGAAT
TTATGTTTGGAAGAATTCGGAGCAATTTTATTTGCAGATAATAAAAAGCTTTATTTTT
ACGATGAAAAAAGtTGGTATGTAAgGACAGAGAAGCAATTTCGTTATTTATATAATA
CAGAAGAAGTTTCGGTGGATACGAACACAGACAATTTGAAGACGGAGATAAAATGT
TACGGCAAGCAAAAGAGAATGCCGATAAGCTGACTGGAGATAATAAGTACATGGC
GGTTGTCACGTATACTTCGCCaAATGAGGCTATTTACGGGAAACGAATGGCAAATGCt
AAAAGTGATGACAAATCACGAACAATGATGACTTATTAATTTTTGCAAAGAAGCA
AATTCTAGATGTTCCgGAgACgGCGCTTACTATCGCTTACAAAGGAAAAGAACCTGTT
TCAGAGCGGGATGTTTGGTATTTCATTCATGAACCGATGGGGTTTGAAACAGAAGTA
AAAGTAACGAAAATTAAATCGAGTCATCCTTGGAGTAAGAAGTTTCAAGAAATTGG
CTTCAGTAATTCGCGACGgGATATGGTCCGAATTCAAACGCAAATTGCTAATCAAGT
GAAAAAAGCGAGCGTAGATACAAATAAAAtAATTCGTTTTCGAGCATCGCAATGAA
TGCTTATGATTCACGAATTTTAACGGAAGTAGTAGGTGGTAGATGGCGACTGAAA
TTAGAGTGTTAAAAAATGTAGATGATACAGTTTTCTATCCGAAGACACATGTAACGG
CCGTGGAAGGTTTAGACTCGGCTACAACTACTACATCTGGATTAATGCCCGCCAGCG
ACAAAACGAAATTAAATGGAATCGAAGCTAATGCAGAAAAAAACAATGTGACTGCA
ATCGATATTGCCAATTGGAATAAAAAACAGGACGCAATTTTGATTTCTGAAAATGGT
TCTAATTTCAAAATAACTGTCACAAATGCTGGTGAACTAAAGGCAACAAAAGTGGA
ATAGGAAGGAGGTTGCGTATGAAGTTGGATTTATGGAAATGGGAAATGCTTCTTCA
AGGTCGAGAATTTAGAAATAAAACAAATGACAACTCTGCAAAAATTGATGGATTGGT
CCGATTTTATTTCAACAGGTTTAAGCGCGATTTATGTCTATGTAAATAAAGCGGATG
CTACCTTAAATAACAAAATTGATACCGTGGATAAAGCAGTAAATGCAAGGGTTAAT
GAGCTGATTAGCGGGACAGAGCAGCTAAGTGAAGTGGTTGATGCGAGATCAGATGC
GTTTGGTGCACGATATCCTGTGCTAAGAGAACGTTTAAACCAAGAACAGCTTAACTT
TAGCAAAAAGAGCACGATTCAATTTGATGCGAGTACTATCATAAGTATGGAAAAAC
AAGATATTGGGCTGCTAACAAGTAAAAAAATCTCAGAAGCGCAAACCGTATGTTTTT
TAAATATATCAAGCCTCGATGAAGAAGCaGATATTGTtCTTGAAAAAACAGGtGAGAC
AAGCTTCTCaGAcAATTTAACgAGcCTAGTCTTTGCgAAAATTGGAACGAATGAACGC
TACCAAATGGAGCCAGTTGGTGCATAAAGGAGGAGTGAGCgATGACTGAAATAAAG
CGAATGCTaCAGACAAAAGAAGATAATTCAAAAGAACAATTTTATCCAGAGACGCA
TGTTGCgGGGATTGTCGGGTTGACaGAATATGTGTCAGGTCAGCTTCCGACgGGtGTG
GTCAGTGTgAATGGTAAGGCaGGtCGCGTGTTaCTgGATGCtGAAGACGTtCACGCTGCa
AAAAAaAGCCACAcCCAtGAAGTCGCAACATACACtACGGAtGGCTTTATGAGTTCTTT
TGATAAACAAAAGATTGATCAATTAGTTTCACCgGAAGCTGGCGTGACAAGCATAAA
TGGTAAAACAGGGATTGTTGATTTATTCGCATCGGACTTAGATGCAGCAGAGATAAA
CCACACgCATGCAGAAGCaACtACTACAGAAAGCGGTTTTTTatCAAtcGAcGACAAAG
AAAAAtTAGAtGCGATaCAAgTAATCGCGCTGGAAACTATTAAGGAGGTTATAGAATG
ACTAAAATTGTAAAAATGTCAGAGAAgAATGAACATGGAACTcTaGAaCAATTCTATC
CAGAAACACAtGCaGAGGCTGTTAAAGGaCTTGTGtcgGTTtCAGAgGAAGAgAAaAACaAt
TTGGGATCAAAAGGANAGTACGGCGGGTGCAGAGCAAAAAGCAAACACAGCCTTA
AATAGTCTCTAAACTATTATGTGGATACGATAGGIGAAGGAACGGTGATTTTTAAAGG
CGCTAACCTTATGGGAGCTGGCCAATCATTTAAATGGGACGCTTCTAAACTGAAATT
TGGGATGACTTTGTTATTTAGTCGCTATGATGCGGCAAATAATACACCGCAAGATTA
TTATTATCATTCTGTATTCTTATcTAAGGCACAATTAGTTGAGCTTGCAGGGAAAAGGT
ATTTTAGTTCAAATGCCATCAACGACTTATGGAGATCGAAAATATCTGTATGTTlCA
ACAACTGGGTTATCTGGACATTTTGATAATTCGAATTATGCGGCTTGGGCTCTGCGC
CAAGTAACAATTATGTAACTAAAAAGGAGGTTTTCCATGGAAGTCATACTAAAATTC
GGGATTTTAGGTTIGGCGCGATATTTGGATACTTGTTTGGGGAAGTGGATTTATTG
GTAAAAGTGCTGGTGTGCTTTATTGTAGCTGACTATATTTCTGGGCTACTCGCTTCAG
GGTATCTTGGGGAACTTAGCAGCAAAATGGGTTTCAAAGGAATCGCGAAAAAAATC
GCTATCTTAATTTTAGTGGCTATTGCGCATCAAATAGATTTGATTCTGGGAACGCAT
AATACAACCTCGGGATGCGGTTATCTTTTTCTATTTACTCGAATCTAGCTGATTTCTATCT
TGGAANATTTCGTTCGAATGGGAATGAAGGTCCCGGAAGTATTGAAAAATTTAATTT
TGATTTTCGATGCAAAGTCAGGAGAGGATGAGGAAAAACATGAAAAGATATGGAT
TGACGCTGGACAcGGTGGTAAGGATTCAGGtGCGAGTGGTAATGGACTTGTTGAAAA
AAATTGGGTACTAACTGTAGCAAAACAACTTCAAACAGAGTTAGTTAAAGCCGGTTT
TGAAGTGGAATGACAAGAACAAATGATACATTCTATGAATTAAGTGATCGTGCGA
AGAAGGCGAATAGTTTTAAAGCTGATTTATTTATTTCGCTTCATTTTAATGCTGGTGG
CGGTAAAGGATATGAAGATTATATTTACACATCCGTCCCGGCTGCAACGGTAGAAAT
ACAGAAAATAATTCATAAAAATATTATTACTAAAGTTACTAAACACGGAATGAATG
ATCGTGGAATGAAGAAAGCTAATTTCGCTGTATTAAGAGAAACAGCAATGGATGCT
ATCTTACTTGAAGCTGGATTTTGCGATAGCACTGATGCATTAATTCTTGAGAAGAAA
```

```
                                    -continued
GCTTATCAAACTGATTATTGTTTAGGAATTGTATCAGCAGTACAAGAGaTTTTTGGGG
CTATGGTAACAAAATATAGGGCAGGCAAATATTTGACAAGTGACGATGCTATATCA
GGCACAAATATTAAAGGATATTTAGAAGCAGGAACAAAGGTTTTTGTTTATAAAGA
AACAGAAAAAACGCTTAATTTAACTACTACAAAGGGTGTTCCAGGAAGCTGGGTTTT
AAAAACAGAAGTTAATACAGGAAAAAGATAA Listeria monocytogenes strain 1/2a 35152
Monocin ORF 125
>transcriptional regulator                                                               SEQ ID NO: 002
MLHTIDFSDIFSSDYSSKISFKKGEIIHSYRDYEEKAPQIGAILEGKAVLEGPNEGRWMIN
ALIGQHALFGMESLLETKTAPELTEYRVRALENGTVRALENGTVLFIDREFLLNYLYANPQFFHLILDE
VIVRYLFTSKNYKNINQAPIVKVTRILVEIIELLHLHQTEGSIELPVYVTQTFLADYCRSSR
ARVTEVLEELRESGLLLSKKPITISSHENLLDQVDSFQTGNGLLTR Listeria monocytogenes strain 1/2a 35152
Monocin ORE 126
>hypothetical protein                                                                     SEQ ID NO: 003
LYEKLVNKYQDEVTIREEKMPYKLPGLYLNGMIFISKDQSSIEKGCVLVEELMHYKYTV
GNITKQETIMDKKQEIFARRKGYEELIPLDDIIACFYLGLREYFEVAEFLEVTEEFLRHTVS
HYAEKYGPMYDYGGYFINFGNSIDVYKKF Listeria monoeytogenes strain 1/2a 35152
Monocin ORF 127
>putative repressor protein                                                               SEQ ID NO: 004
MELNKFVGNKIKQYREERGLNQEALAEKLHTTRQTISRYENGDRKANQDVLFELAKIFN
KRLDDFFPERNLPPVDERLVTIAAHIDDDVTEEEMRDILAYIEMKKKLHRGM Listeria monocytogenes strain 1/2a 35152
Monocinn ORF 128
>antigen D                                                                                SEQ ID NO: 005
MDRKLLKEKQIQLIFQLEQEENRFIRKRLIEELEFFEALGDREKGLLTAEQKLLILTPSEYR
EYKRTKSDVQISRIIGVSRSSLAEWKRKKGLNRKKSQPVQQEMIDVLAFHLDKTKEEIGA
LPASAIECQYEAFVINEANN Listeria monocytogenes strain 1/2a 35152
Monocin ORF 129
>antigen C, transcriptional regulator                                                     SEQ ID NO: 006
MQVLVLPENKDINYIKTVHEVKRFFADFERFRMITGLSKKPHLLRNGFLEEPQFEPVAFS
ARHNKEVILEARWLVEKYTEMLNQMDDLYRTILMECYVERKQDVAVMMDLPYHAQF
KRIKKRAVLELATLMGILVRK Listeria monocytogenes strain 1/2a 35152
Monocin ORF 130
>antigen B                                                                                SEQ ID NO: 007
LSFMRVLEAVRTMLQEKGGLDVSIVMRNQVEMPTTMIEMIDQEEEESQTAWKEKYRFA
IFEEIYTNEQDLAGVEKIDTLIQMGFILPEGYKLVAVRHCGKQNLVKENTLIFIAKTSFEVSI
CRELKVKI Listeria monocytogenes strain 1/2a 35152
Monocin ORF 131
>antigen A, phage tail-like protein                                                       SEQ ID NO: 008
MAFEENLYCDYTPGAAKAVAGKDVILAVFNAAGDKLLAVAGQQGLTVNRSKDSIEITS
KDTVGGWKSKIGGMKEWSIENDGLYVADAESIAKELAKYFESDSPVCVKIINQASKKGL
FGGLAIVADYSFEAPFDEAMTYSVKLDGMGALVDLTITEGGDQMPGETPVAPAE Listeria monocytogenes strain 1/2a 35152
Monocin ORF 132
>hypothetical protein                                                                     SEQ ID NO: 009
MFEVNDTTYILRFNKQKVKTVELTSGISLVAALTANKGILSYQVIETLFVSGLVEEKGLV
PVKQKEALEIFDKLVEEQGLISLNVAVIEKLQEDMGFLFR Listeria monocytogenes strain 1/2a 35152
Monocin ORF 133
>hypothetical protein, phage-like                                                         SEQ ID NO: 010
MNHDFDLEKQFAFFVVNFQMSKGDFEELTEVEKNFIMKEWENKVIFESTMLRNAVLNA
EQNLNRKRNSRFIDLEIKKRQKKADVNYTVNALQAISDNEAKEGKAWIDRIYGANGLRR
PKNKEERGKMNGGV Listeria monocyingenes strain 1/2a 35152
Monocin ORF 134
>tape measure protein                                                                     SEQ ID NO: 011
MAESKSITFELNESVLTAQVGRLDEMAMVVERRFSELKMTIEDVGNADPGSKISESLGG
LQSGLGTISSAFGQLGSSSEAITSGFGTAVGSVGGITDAFKNLGSSVQNGTLFSSLATGIG
GMSTMLGGVSGGVQGITNLASGFMELKNHLGGLMSSIGGVGGIMGKLTSPMGLVIIGIV
ALVAAFTYLMTTNESFRNTVMSVVTQVAQLFGQLVASLMPIIIVIQIVTAVMQIGAALMP
MVMQFISFFAQLLAQLMPFINMLISMLMPVIIVIQIVQVVMSLVSALLPSIIVITVIQGIIVISVI
QFLIPIIIVIQIATVVVQIVVTIISYISKIMPIVMTIIGVIVSITTTIISYVVIIATTIASVIGKIISFIAS
VITAVIGIVQPIIAFITNIFTTIVTIIGAAFQMVFTVASKIWNSIIVISTISGIIDGIKAVITGISTT
VSSVFNGVKRIITGVFDGIKSAWGGLTDFVGNIFDGVSSAIQTVVDNVKGFVNVVIRGIN
```

-continued

```
GAIGLINKIPGVEIGKIPQLISGTTNFQGGFARMNEGGRGEMVVLPSGSQVIPHDATMKY
ARESARGNKSMLYTSQGADLARVENLLERLLQKNPVIKMDDKVVAEVVSRNQANSFD
QYNYTMGGAAYS
```

```
Listeria monocyingenes strain 1/2a 35152
Monocin ORF 135
>phage tail component                                                     SEQ ID NO: 012
MSDLFLELNGKVHSLSETFPGLSVQEVSRQSPQLSMETAEIAGTDGVIPGMTQFKPFIFSA
KCNLQALDIPDYHLAVREIYEFLFQRDSYYIWSDQMPGIRYEVEEPKPVDFSRESDRVGLL
TIEFDVFKGYAESRGTSLDPMTFEVDLWQMGMNLSNRDDLFYVFRENTFRVYNAGSDR
VNPLIVIRRELDIAMTANGTPTIFINLTTGESFEYRKELQKTDVLLLNNIYPLVNNRRVGKD
TNHGIITLEKGWNDFE1KGVTDVTIAFNFPPFIYR
```

```
Listeria monocytogenes strain 1/2a 35152
Monocin ORF 136
>phage tail protein                                                       SEQ ID NO: 013
MDYVIIQSMDKEVEEILTDIDYGSFSYDYEKNTSRAISFTVNKTKQNAAIFDLVGNEAILT
YQGGQPFVIKKCTPKSIGGTISKQITAQHICYTVQDHVQYNVKSGRKKYSIQTVLEFALQD
NVLGFSYEIQGSFPLVELEDLGNKNGLELVNLCLEEFGARYADNKKLYFYDEKSWYVR
TEKQFRYLYNTEEVSVDTNTDNLKTEIKCYGKQKENADKLTGDNKYMAVVTYTSPNEA
IYGKRMANAKSDDKITNNDDLLIFAKKQILDVPETALTIAYKGKEPVSERDWYFMEP
MGFETEVKVTKIKSSUMSKKFQEIGFSNSRRDMVRIQTQIANQVKKASVDTNKINSFSS
IAMNAYDSRILTEVVGVVDGD
```

```
Listeria nionocytogenes strain 1/2a 35152
Monocin ORF 137
>hypothetical protein, phage-like                                         SEQ ID NO: 014
MATEIRVLKNVDDTVFYPKTHVTAVEGLDSATTTTSGLMPASDKTKLNGIEANAEKNN
VTAIDIANWNKKQDAILVSENGSNFKITVTNAGELKATKVE
```

```
Listeria monocytogenes strain 1/2a 35152
Monocin ORF 138
>hypothetical protein                                                     SEQ ID NO: 015
MKLDLWKWEMLLQGREFRNKTNDNWQKLMDWSDFISTGLSAIYVYVNKADATLNNK
IDTVDKAVNARVNELISGTEQLSEVVDARSDAFGARYPVLRERLNQEQLNFSKKSTIQFD
ASTIISMEKQDIGLLTSKKISEAQTVCFLNISSLDEEADIVLEKTGETSFSDNLTSLVFAKIG
TNERYQMEPVGA
```

```
Listeria monocytogenes strain 1/2a 35152
Monocin ORE 139
>hypothetical protein                                                     SEQ ID NO: 016
MTHKRMLQTKEDNSKEQFYPETHVAGIVGLTEYVSGQLPTGVVSVNGKAGRVLLDAE
DVHAAKKSHTREVATYTTDGFMSSFDKQKIDQLVSPEAGVTSINGKTGIVDLFASDLDA
AEINHTHAEATTTESGFLSIDDKEKLDAIQVIALETIKEVIE
```

```
Listeria monocytogenes strain 1/2a 35152
Monocin ORF 140
>receptor binding protein                                                 SEQ ID NO: 017
MTKIVKMSEKNEHGTLEQFYPETHAEAVKGLVSVSEEEKTIWDQKESTAGAEQKANTA
LNSAKDYVDTIGEGTVIFKGANLMGAGQSFKWDASKLKFGMTLLFSRYDAANNTPQD
YYYHSVFLSKAQLVELAGKOLVQMPSTTYGDRKYLYVSTTGLSGEEFDNSNYAAWALR
QVTIIVI
```

```
Listeria monocytogenes strain 1/2a 351.52
Monocin ORE 141
>holin                                                                    SEQ ID NO: 018
MEVILKFGILGFGAIFGYLFGEVDLLVKVLVCFWADYISGLLASGYLGELSSKMGFKGIA
KKIAILILVAIAHQIDLILGTHNTTRDAVIFFYLANELISILENFVRMGMKVPEVLKNLILIF
DAKSGEDEEKHDKDMD
```

```
Listeria monorytogenes strain 1/2a 35152
Monocin ORF 142
>lysin                                                                    SEQ ID NO: 019
MRKNMTKIWIDAGHGGKDSGASGNGLVEKNWVLTVAKQLQTELVKAGFEVGMTRTN
DTFYELSDRAKKANSFKADLFISLHFNAGGGKGYEDYIYTSVPAATVEIQKIIHKNIITKV
TKHGMNDRGMKKANFAVLRETAMDAILLEAGFCDSTDALILEKKAYQTDYCLGIVSAV
QIFGAMVTKYRAGKYLTSDDAISGTNIKGYLEAGTKVFVYKETEKTLNLTTTKGVPGS
WVLKTEVNTGKR
```

```
Listeria monocytogenes strain 1/2a 1144 (DuPont)
A118 propliage tail fiber and downstream ORFs                             SEQ ID NO: 020
atgacaaatcaaatctcttagatcagctattcttgattttctgttagtgcacagaacgctaaagctaatgttcctcagataaaattagtacgcaaga
ctctggagggactgcgcgattaaagtttactgcaaaaaagatgataacaatttaccactttcaagcgcggcagaggtaacgcttgctatggt
attgtctgttggcaaaaaatacgaaagtagctacattgttaatccagaaataattaacagaacagaaggtgttttgaatactcattgactgatga
gcaaataagtcacgacggacaagctaatgcagaattgtacgttaaatatccaaatcaaacaatgcaaatcaatcgttttagttttgttattgaaaa
agcgatgattgatgataattttttgcccgttgctacctattatgttgaaaatgggatgattacgaaaaaatatttaacgaaaaagtggaaattctt
caaaatgaaattgatgatttgcaaggacaagctactgaattaaaaaacacattcgatagtcttaatccagaccaatttccecaaaaagcagattt
tgaaaatcatatataaaaacacaaacatttcatgtgacgatgactgataaaacaaattggaatacaaaagaaaatactgcgggatcacaagcaa
aagcggatagtgcattaaactctgctaaagcatatacagatagcaaagatggatagttacggagcttggatatatgtaccctcgcctctggtta
ctcaactggcgacagtaatacacctcaatatcgactggtagcaaaacaaacattaccggtttgaaaactttgctgaattccgcggatcagtt
gctggtacatttattagtacagcaaatagtactcttgcaacaatgcccgctggcacaagaccaattgtcacttattacggtgctgccacttcaaa
```

-continued

```
taacgggaacggtggtcgtattgctattccagttgacggaaagctattacaagtgtcatctacagataatgctaatccttcgtacgtaagcctttc
aacgatattatacgaagttggcaattaggaggagtaaacatgaactataaacagattacgcatatgatgaaaatggcaattatctcgaaacaa
tacttgtgtttgaagatgaaaaaggtttaatcaatcaccgaaaaattctacaaatattgaaccttccataatcgaaaacggcatagcaagagc
aatgtattatccgcgtatgaatggggaagattgggacgaagaaaagaaaatatgggaattagaaaatccaatcatacccccagaaaaaac
ggaaatagaaaaattaagagaggaattactactcacccaagaagcgttagcggaattgttcgaaagtaattagggtgatgaaatggettata
tgataccaatttacgtgaatttagtgatgaataatcgaaaaactattgaagaagttcctgcgaatttgcgaggtcaggtaaaagcaaaagtgga
tgagctaaaacaagaacaacaacgaatacagtcagaagaaatagaagccgaataggcttatttatatggttgatgatgaaaatgtatgatg
gactaacaaaagttttgattatgcttagcgaaagaaattttcttcgcggcgctctttgtagcgcttttataatettactaattatcacaaaaga
atttgggatgattcgaaaattgtaagaatagaaatgaaagaagangegaaaagtggaggaagaacgagagaagcgtaataaggaatcg
aaagaagagagagataaatttataagtaegaataacgaacanagcgattgatgtataggcaaaatgacatgatgaaacagcaacaacaa
tcaattgacagettgtctaaatcagtcggaaagttagctcacaaagtagatttgatggaacacaaaataacgaatgaaggatgatagaaatg
gagtttggaaaagatttartagtttacatgacattatattagttgtaacacctgtgttgttcagcgattaagaagaaggagttagtaccgtcta
agtggcttccgactgttagcatacttattggtgctattctgggcgcattagcaacgttttggacggctctggatcgcttgcaacgatgatttggg
caggcgattagcaggagctggtggtactggattatttganaatttactaatcgaagcaaaaaatatggagaggatgataaataa
```

Listeria monorytogenes strain 1/2a 1144 (DuPont)
ORF 2345
>A118 tail fiber gene                                                                SEQ ID NO: 021
MTNQIFK

```
                                   -continued
CCTCCAGTCTGGCCCTGCACGCGCCGTCGCAAATTGTCGCGGCGATTAAATCTCGCG
CCGATCAACTGGGTGCCAGCGTGGTGGTGTCGATGGTAGAACGAAGCGGCGTCGAA
GCCTGTAAAGCGGCGGTGCACAATCTTCTCGCGCAACGCGTCAGTGGGCTGATCATT
AACTATCCGCTGGATGACCAGGATGCCATTGCTGTGGAAGCTGCCTGCACTAATGTT
CCGGCGTTATTTCTTGATGTCTCTGACCAGACACCCATCAACAGTATTATTTTCTCCC
ATGAAGACGGTACGCGACTGGGCGTGGAGCATCTGGTCGCATTGGGTCACCAGCAA
ATCGCGCTGTTAGCGGGCCCATTAAGTTCTGTCTCGGCGCGTCTGCGTCTGGCTGGC
TGGCATAAATATCTCACTCGCAATCAAATTCAGCCGATAGCGGAACGGGAAGGCGA
CTGGAGTGCCATGTCCGGTTTTCAACAAACCATGCAAATGCTGAATGAGGGCATCGT
TCCCACTGCGATGCTGGTGCCAACGATCAGATGGCGCTGGGCGCAATGCGCGCCAT
TACCGAGTCCGGGCTGCGCGTTGGIGCGGATATCTCGGTAGTGGGATACGACGATAC
CGAAGACAGCTCATGTTATATCCCGCCGTTAACCACCATCAAACAGGATTTTCGCCT
GCTGGGGCAAACCAGCGTGGACCGCTTGCTGCAACTCTCTCAGGGCCAGGCGGTGA
AGGGCAATCAGCTGTTGCCCGTCTCACTGGTGAAAAGAAAAACCACCCTGGCGCCC
AATACGCAAACCGCCTCTCCCCGCGCGTTGGCCGATTCATTAATGCAGCTGGCACGA
CAGGTTICCCGACTGGAAAGCGGGCAGTGA Listeria monocytogenes strain 1/2a 35152, Listeria monocytogenes strain 1/2a 1144
(DuPont)
Monocin ORF 140, A118 tail fiber gene
>monocin-A118 phage tail receptor binding protein fusion                SEQ ID NO: 029
MTKIVKMSEKNEHGTLEQFYPETHAEAVKGLVSVSEEEKTNWNTKENTAGSQAKADSA
LNSAKAYTDSKMDSYGAWINVPIASGYSTGDSNTPQYRIVAKQTSIGEKTFAEFRGSV
AGTFISTANSTLATMPAGTRP1VTYYGAATSNNGNGGRIAIPVDGKLEQVSSTDNANPSY
VSLSTILYEVGN Bacteriophage TP901-1
>major tail protein                                                      SEQ ID NO: 030
MAELTAKQGKDIILLYRVLSKASTEAAWKLAFQTEHSNEKTRDYNTTATKDGPVGALA
EVEYSLSATSIAANGDPHLDEMDKAFDDAAIIEVWEIDKAEKATLGLDSGKYKAKYLRA
YLTSFSYEPNSEDALELSLEFGVFGKPQKGYATLTTEQANVVQYVFKDTVRG TP901-1 like phage from Enterococcus avizon
ATCC 14025                                                               SEQ ID NO: 031
MPEVTGFENQLYCDFSQSATKAVAGKNILLAIFNMTGDKLLAIAGQQGLTINRSKDSIEI
TSKDTKGGWKSKIGGMKEWSIDNDGLYVRDDESHKVLGQYFDGDDPVCIKVLDMQSK
TGMFGGLAIVTDYSLEAPYDDAMTYSIKLDGMGALVDLSDSEANQMPEGTASIKLNKT
TASIVVDANESLIATVQPSTDTVSWKTSDVTVATVDNTGRVTGKKVGNAIITATSTSKEV
ATCLVTITAS Listeriophage A118
>major tail protein                                                      SEQ ID NO: 032
MRIKNAKTKYSVAEIVAGAGEPDWKRLSKWITNVSDDGSDNTEEQGDYDGDGNEKTV
VLGYSEAYTFEGTHDREDEAQNLIVAKRRTPENRSIMFKIEIPDTETAIGKATVSEIKGSA
GGGDATEFPAFGCRIAYDETPTVTKP Listerlophage A118
>tape measure                                                            SEQ ID NO: 033
MSDGSVVIEISLDDKKADKQLDAFEKDLAKAGTNAGAALDKAYREAVSDIASQSKRLK
DTFVNAFKSMGNAGSNALKASLNFIRELPSNVQAALSKLASTVKTGFVNAAKASITAVK
NLGTSIKNTAVNIKNGFFSIAKTVQSSIMSAVKISINVIKSIPSAIKSAGSSIKSALVSSLQA
AKMAAISFAQTTVKVIKSIPGAAKTAATAVKNSFVVAYKAVVVAAYMSVKGTISAVKA
IPSATKSAALAVSSAMKTAFSAVVSAAKTTGTTVKTALTNGFSAIKSGAKTAGQVGISA
LKGLGNAAKSTGSLIKNGLVSGFNAARSAAKGAGAGMREALKNSVEKPAEQARFSILR
LAAAFGLIAATKNVVGSAIGRVDTIDTATKSLTVLTGSAKDAQLVMTDLTAAIDGTPIAL
DAVALGAKKMVAAGMQAANVKPVFTAIADAAYGVGNGSESIDQMTDAISALQASGVA
YSDDINRLVDAGVPAWILANSTGKSVGEMKKYVSEGSLESTKAIAMLTKGIEEGTTGM
AGNTAKMAGLAKTAGNTISGSFANMKTAAVKSLANIAENLKGPIIQALDVAKNAFKQF
AAVTASPEFQKKLSDMIQKIKELIPVMVKLAPTILKVVSAMLALQAVSSVYVAFSNIGK
MFVPLKNGLFVIATGFMKLAKTIREEPITAIKNLAFAIKYFIVTSGAVIAIVGAVIAVLYGM
YAAFKENTANIKGFLSGMFDAVKNSFGKIVDVFKQIVSALKPVGSGFKDILKYIGVGVW
VAFGIVLATVVDIIQVLARIVLVAIKGLQGLYYMKAAFQALSGDLKGAKKSLEQSKDAF
VDAGSAIKDAFNKDNYALTGTIESLKEMGGEAEKTGTKAETSNKKISSSLKLVESTAKQ
TEATVTKSNQAIDTMLSGGVDQYGNKLSEKTKSFLNAAKELYGQYQESAKKSQDKYSV
AMEKAQSLEGDKRKKAIADANATLVAEIDKNNGTLLTLQADYAKLLKDNKWVDGTEL
TAQQKKFLQQQTADIQAELAKQNQLYVEGNLLKLANGKTLNEKERATIEVQKSLYGD
RKKAVEIGEKELADLKRKKSDATTETEKANYQIQIDEQTKKNKTLAGNLQKWASEMNA
IIANGGTLNAETFAKGLSEMGNISDEQLGAVWQDFVKVSGSIDNTLAGLAAVMSQRG
EGVQAFVTALQSGDYTTAALKINDDVLNTISGLPNSMFLNGQSGKDQFLLAIKSGDFQG
AGKFLLDGVKMGADPLPGEMEKNGKKSGDQAKGVKSTAEANKSAGKEKNNAKSG
AFDPNLFKMTGSKNSSGFNNGILGGKDGAFSAGTSVGGSAKSGAASVDSSGVGSDFAA
GFANGIRSGAGAVGEAAASIAAKALAAVQKKQDSHSPSKKSKKLGGDFGSGYSLGIASK
TKAVTKAASNLVAGALGTEKQIKKLSSTLKDKVSSAIDAGLHSKNKSRGQLKQAKALN
SIEGYIAQQTNRLAATAKKRDKVVAQLKAANTKMADLTKQSKEYAASITEKMQSYGSI
SNVDAENPQSIQQEMQKRLKEIKAFQANVEKLRKKGVSKDIISDILESGVENGSSYAQAL
AKSDAKTIKAINSTQNQINSASKSMGNTAANAMYSAGINAAKGLINGLNSQKKQLEKTA
KSIASTITNSVKKALKIHSPSRVAIELGKFFTGGLGNGVLAGAKGAVQSTNKMVDKVVN
AASNMTVPTITLPKVSAEKALGLKSSDLNRTITVKAIVENESKNNSNSDLINAIEKSGGRP
IILNVDGKVIADSTNNIALGNSTSLAFYGKGL
```

Listeriophage A 118
>gp17                                                                                           SEQ ID NO: 034
MATSLALVIEGKTYMLNELFDLEVGEVSREPPQIVNNYTEFAGSDGARTTDSNFSMFPISI
LCHFQTKTADLYHIKLDELLELIYQRKEYFLVHSKTPGKKYRVEEPSGVAIYRKAPGYAD
LTLEFDVFRGYSESLSSTLSDSEIDCDKWQFGQGLAMEDYRYTHTKSRFIYNGGSFDIDP
REHQLTITIRGQNEGELVINNITTGDRFIYYPALSATDTLVIDSATPRINGNPCGRSTNHGL
ISLQKGENLIEISNTSHLDTRWDFSFLYK Listeriophage A118
>gp18                                                                                            SEQ ID NO: 035
MNSDIIVADFWKNNEEILTDFDKESFCETWTENEMWNIEFKVTQTNKNANCYSFLDYES
SVFFGGQEFVVKQLSRDAVGKTLSKDIKAPHIYYTCQDGRQDDTITGSFTLEQCLTHIFK
SDSRGFSWEIIDPSNILEKVQQENFGNNNYLTLIDQLLDDYGVVVIPDNREILVFKPRENY
GAKTENFIRYKYNTDEASFDIDTLSLKTKIKGYGKVDSNGNNYFSPVTYTSPEAEKWGIR
WQEPVSDERYTVVGNMQRRLKLELQDYPATTGSVILKNDYECEKGDYVLFIYEPLGIDY
DVQIVAYKKYPFTIKAPEITLSNNKKSIVSIMAQLAKVLKGAK Listeriophage A118
>gp 35 (regulatory)                                                                              SEQ ID NO: 036
MNKTSYELKQEFPELNFVINNNLPTKLFGLIQNKVVIALEEPDLSENELRCTHEEAMEIWKY
TAGDITKFNNVENIKQEKFARRKAHEYLVNIQSLALCYDLGYRTYYEAATFLNVTEKFLI
EAVENYREKYGLMYNNGNYIIHFGSTIQVFQEDNSFYPYDYGC Listeriophage A118
>gp61 (regulatory)                                                                               SEQ ID NO: 037
MSRKELRKKQWEVITMIEKSKTLTDRKNIIKKLETLEARGDKEKGLATPTQLLSITTVTE
YRRLSKKLTDTEIAEDMGISRSALIEFKRKNGLSIRQKVAT Listeriophage A118
>gp66 (regulatory)                                                                               SEQ ID NO: 038
MGQLFNLPQVEDINYIQTVRAVRQFFKDYLTLRLMAGDRKFPNWITTMYKITPPNFSNEF
HSKVEDAAIFINVDNVHAAQEAVKKYDAIMNQLEHIHRKILFEKFIFINLQDRTIMLDIPY
EERQYKREKRKAVIELATTLGIEVLN

---

What is claimed is:

1. An isolated nucleic acid molecule encoding an F-type bacteriocin, wherein the nucleic acid molecule comprises a first polynucleotide sequence that encodes the following structural proteins: a structural protein at least 90% identical to SEQ ID NO: 7; a structural protein at least 90% identical to SEQ ID NO: 8; a structural protein at least 90% identical to SEQ ID NO: 9; a structural protein at least 90% identical to SEQ ID NO: 10; a structural protein at least 90% identical to SEQ ID NO: 11; a structural protein at least 90% identical to SEQ ID NO: 12; a structural protein at least 90% identical to SEQ ID NO: 13; a structural protein at least 90% identical to SEQ ID NO: 14; a structural protein at least 90% identical to SEQ ID NO: 15; and a structural protein at least 90% identical to SEQ ID NO: 16,
    wherein the nucleic acid molecule further comprises a heterologous second polynucleotide sequence encoding a heterologous receptor binding protein (RBP), and wherein the RBP comprises an amino acid sequence at least 90% identical to SEQ ID NO: 29,
    and wherein the F-type bacteriocin has bactericidal activity against at least one strain of *Listeria monocytogenes*.

2. A vector comprising the nucleic acid molecule of claim 1, wherein the nucleic acid molecule is operably linked to an inducible promoter.

3. The vector of claim 2, wherein the promoter is a small molecule inducible promoter.

4. An isolated nucleic acid molecule encoding an F-type bacteriocin of claim 1, wherein the nucleic acid molecule further comprises a heterologous promoter inducible by a small molecule, wherein the first polynucleotide sequence is operably linked to the heterologous promoter.

5. The nucleic acid molecule of claim 4, wherein said nucleic acid molecule further comprises a nucleotide sequence encoding the polypeptide sequence of SEQ ID NO: 5, and wherein the promoter is placed at 11, 14, 17, 20, or 23 nucleotides upstream of the nucleic acid sequence encoding SEQ ID NO: 5.

6. A vector comprising the nucleic acid molecule of claim 5.

7. An isolated F-type bacteriocin producer cell comprising the vector of claim 2.

8. The isolated nucleic acid molecule of claim 1, wherein the RBP comprises the amino acid sequence of SEQ ID NO: 29.

9. An isolated F-type bacteriocin producer cell comprising a first foreign polynucleotide sequence that encodes the following structural proteins: a structural protein at least 90% identical to SEQ ID NO: 7; a structural protein at least 90% identical to SEQ ID NO: 8; a structural protein at least 90% identical to SEQ ID NO: 9; a structural protein at least 90% identical to SEQ ID NO: 10; a structural protein at least 90% identical to SEQ ID NO: 11; a structural protein at least 90% identical to SEQ ID NO: 12; a structural protein at least 90% identical to SEQ ID NO: 13; a structural protein at least 90% identical to SEQ ID NO: 14; a structural protein at least 90% identical to SEQ ID NO: 15; and a structural protein at least 90% identical to SEQ ID NO: 16, and
    wherein said producer cell further comprises a second foreign polynucleotide sequence encoding a heterologous receptor binding protein (RBP), and wherein the RBP comprises an amino acid sequence at least 90% identical to SEQ ID NO: 29,
    and wherein the F-type bacteriocin has bactericidal activity against at least one strain of *Listeria monocytogenes*.

10. The isolated producer cell of claim 9, wherein the first and second foreign polynucleotide sequences are contained within separate nucleic acid molecules.

11. The isolated producer cell of claim 9, wherein the first and second foreign polynucleotides are contained within one nucleic acid molecule.

12. The isolated producer cell of claim 9, wherein said first and second foreign polynucleotide sequences are operably linked to a heterologous promoter inducible by a small molecule.

13. A method of producing an F-type bacteriocin, comprising exposing the F-type bacteriocin producer cell of claim 12 to an inducing agent in a concentration effective to induce expression of the F-type bacteriocin via the inducible promoter, thereby producing the F-type bacteriocin.

14. The isolated producer cell of claim 9, wherein the RBP comprises the amino acid sequence of SEQ ID NO: 29.

15. An F-type bacteriocin, wherein said F-type bacteriocin is encoded by a nucleic acid molecule comprising a first polynucleotide sequence and a second polynucleotide sequence,
- wherein said first polynucleotide sequence encodes the following structural proteins: a structural protein at least 90% identical to SEQ ID NO: 7; a structural protein at least 90% identical to SEQ ID NO: 8; a structural protein at least 90% identical to SEQ ID NO: 9; a structural protein at least 90% identical to SEQ ID NO: 10; a structural protein at least 90% identical to SEQ ID NO: 11; a structural protein at least 90% identical to SEQ ID NO: 12; a structural protein at least 90% identical to SEQ ID NO: 13; a structural protein at least 90% identical to SEQ ID NO: 14; a structural protein at least 90% identical to SEQ ID NO: 15; and a structural protein at least 90% identical to SEQ ID NO: 16, and
- wherein said second polynucleotide sequence encodes a heterologous receptor binding protein (RBP), and wherein the RBP comprises an amino acid sequence at least 90% identical to SEQ ID NO: 29,
- and wherein the F-type bacteriocin has bactericidal specificity against at least one strain of *Listeria monocytogenes*.

16. A method of killing a *Listeria monocytogenes*, comprising contacting the *L. monocytogenes* with an effective amount of the F-type bacteriocin of claim 15, whereby the F-type bacteriocin binds and kills the *L. monocytogenes*.

17. The method of claim 16, wherein the contacting is with a surface contaminated with *L. monocytogenes*.

18. The method of claim 17, wherein the contacting and killing are at 4°-10° C.

19. The F-type bacteriocin of claim 15, wherein the RBP comprises the amino acid sequence of SEQ ID NO: 29.

20. An isolated nucleic acid molecule encoding an F-type bacteriocin, wherein the nucleic acid molecule comprises a polynucleotide sequence that encodes the following proteins:
- a structural protein at least 90% identical to SEQ ID NO: 7; a structural protein at least 90% identical to SEQ ID NO: 8; a structural protein at least 90% identical to SEQ ID NO: 9; a structural protein at least 90% identical to SEQ ID NO: 10; a structural protein at least 90% identical to SEQ ID NO: 11; a structural protein at least 90% identical to SEQ ID NO: 12; a structural protein at least 90% identical to SEQ ID NO: 13; a structural protein at least 90% identical to SEQ ID NO: 14; a structural protein at least 90% identical to SEQ ID NO: 15; a structural protein at least 90% identical to SEQ ID NO: 16; and a protein at least 90% identical to SEQ ID NO: 17,
- wherein said polynucleotide sequence is operably linked to a heterologous inducible promoter.

21. A vector comprising the nucleic acid molecule of claim 20.

22. The nucleic acid molecule of claim 20, wherein the promoter is a small molecule inducible promoter.

23. The nucleic acid molecule of claim 20, wherein said nucleic acid molecule further comprises a nucleotide sequence encoding the polypeptide sequence of SEQ ID NO: 5, and wherein the promoter is placed at 11, 14, 17, 20, or 23 nucleotides upstream of the nucleic acid sequence encoding SEQ ID NO: 5.

24. A vector comprising the nucleic acid molecule of claim 23.

25. An isolated F-type bacteriocin producer cell comprising the nucleic acid molecule of claim 20.

26. An isolated F-type bacteriocin producer cell comprising the nucleic acid molecule of claim 22.

27. A method of producing an F-type bacteriocin, comprising exposing the F-type bacteriocin producer cell of claim 25 to an inducing agent in a concentration effective to induce expression of the F-type bacteriocin via the inducible promoter, thereby producing the F-type bacteriocin.

* * * * *

SEQUENCE LISTING

<160> NUMBER OF SEQ ID NOS: 52

<210> SEQ ID NO 1
<211> LENGTH: 11641
<212> TYPE: DNA
<213> ORGANISM: Listeria monocytogenes strain 1/2a 35152

<400> SEQUENCE: 1
ttatctggtt aataagccgt ttccggtttg aaaactatct acttgatcga gtagattctc     60
gtgcgagcta atggtgatgg gcttttttgga aagcagtagt ccgctttccc gtaattcttc    120
taacacttca gttactctag ctcgactcga acgacaataa tcagctaaga acgtttgcgt    180
gacatagact ggaagctcaa ttgagccttc tgtttgatgc aaatgaagta gctcaataat    240
ttccaccaaa atacgcgtta ctttgactat gggtgcttga ttaatattct tgtaattttt    300
tgatgtaaat aaatatctaa caataacttc atcaagtata agatggaaaa attgtggatt    360
tgcatataaa taattgagaa gaaactcgcg gtcaataaat agaacggtac cgttttctaa    420
tgcgcgaaca cggtattcag taagttcggg cgctgttttt gtttcgagta aactttccat    480
tccaaaaagc gcgtgttgac caatcaacgc atttatcatc cagcggcctt catttgtagg    540
accttctaaa acagcctttc cctctaaaat agcaccaatt tgcggcgcct tttcttcgta    600
atctctatat gaatgaataa tttctccttt tttaaaagaa atttttacttg aataatcact    660 agaaaaaata tctgaaaaat ctatcgtgtg aagcattatc aaaactccta tactaaggta    720
aaattggtat ttaccatatt actgtactgc tatttgtgtc aaaagatac cgaataaaaa     780 tcgtgttcac aatttagaca tgaaaaagtc acttttttagc aacaatttta gtgatttttat   840 caataaaaac ttacttttttc ttccctggag agatatccaa ccaaaaaaag accctccgta    900
gataggagag tctttcaaaa cttcttgtaa acatcaatgg aattgccaaa attaatgaaa    960

```
tatccaccat aatcatacat tggaccatat ttttccgcgt aatgagaaac tgtatggcgc    1020
aaaaattctt ctgttacctc taaaaactcc gctacttcaa atattctcg taagcctaga      1080 taaaaacaag caatgatgtc atcaagcggt attagttcct cataaccttt gcgacgagcg    1140
aaaatttctt gttttttatc catgattgtt tcctgtttgg tgatattacc tacagtgtat    1200
ttgtaatgca tcaattcttc tactaaaaca cagcctttt caatggaaga ttgatcctta    1260
ctaataaaaa tcatcccatt taaataaagt cccggaagtt tgtaaggcat tttctcttct    1320
ctgattgtta cctcatcttg gtatttattt accaattttt cgtacaataa aatcacatcc    1380
cgcgatggag ttttttcttc atctctatat aagctaaaat atcccgcatt tcttcctcgg    1440
ttacgtcatc atcaatatgg gctgcaattg ttaccaagcg ttcatcaaca gggggtaaat    1500
ttctttcagg aaaaaagtca tctaatcgtt tgttgaagat ttttgcaagt tcaaataaaa    1560
catcttgatt tgcttttcga tcaccatttt cataacggct aatagtttgg cgagttgtat    1620
gaagcttttc tgctaatgct tcttgattta agcctcgttc ctcgcgatat tgttttattt    1680
tatttcctac aaatttattt agctccataa taattgtcct ccatatgttt atggcttcag    1740
tatagcactt ttagcaccaa aacggaactt tttcgaacat atttgtcgga taaagtttac    1800
cagtaaccaa aatggtgcta taatatttgt agagctagaa aataaatgcg gctgattttg    1860
caccgatagc accgaatcgg tgacaaaact actatattaa tttatgagat ggaagtggga    1920
atggatggat agaaaacttt taaagaaaaa gcaaatccaa ctaattttc aactagaaca    1980 agaagaaaat cgattattc gaaagcgttt gatagaagag ttggagtttt ttgaagcact    2040
tggggatagg gaaaaaggac ttctaacggc ggagcaaaag ttgcttattt taacacctag    2100
tgagtaccga gaatacaaaa gaaccaaatc agatgtgcaa attagtagga taattggagt    2160
atcgagatcg tcacttgcag aatggaaacg aaaaaaaggt ttaaatagaa aaaagtcgca    2220
accggttcag caggaaatga ttgatgtatt agcttttcat ttagataaaa caaaagaaga    2280
aattggcgct ttacctgctt cggcgattga atgtcagtat gaggcttttg tgattaatga    2340
agccaataat taaggagtga taaaatgcag gttttagttt taccagaaaa taaggatatc    2400
aattatataa aaacggtcca tgaagtaaaa cgatttttg cggatttcga gagatttcgg    2460
atgattacgg ggttatcaaa aaagccacat ttacttagaa atggttttct ggaagagccg    2520
cagtttgagc cggtagcatt ttctgctaga cataataaag aggtcatttt ggaagcgcga    2580
tggttggtag agaaatatac tgaaatgttg aatcagatgg atgatttata tcgaactatt    2640
ttgatggaat gttacgtgga acgaaaacaa gatgtggcgg taatgatgga tttaccgtat    2700
gaaattgccc agtttaaacg gataaaaaaa cgggcagtgc tagaacttgc aacgctaatg    2760
ggaattttag taaggaaatg atgatacttt cgtgatattt tgaaacatca ttttcctatt    2820
aatatagaag taagctaatt gtccagtaag cggatgacaa taaaagctgc atcagaatga    2880
aggtgcaccg attttctgat aatacatgat gttttacaag aaatttgttt ttatgattgg    2940
atttaaatcc gttgagataa acaaatattc tattttggaa agtaaagttc ggaggaataa    3000
attattaaat gtggtcttga ccgaactttg cttctgtttt taaggagtg aacgcttggt    3060 gaagagtttg agcttcatga gagttttgga agcagtgaga acaatgctcc aggaaaaagg    3120
cggactagat gtttctattg taatgcgtaa ccaagtggaa atgcctacaa cgatgatcga    3180
gatgattgat caagaggaag aagaaagcca aactgcctgg aaagaaaaat accgttttgc    3240
tatacatcat tatacaaatg aacaggactt agcgggggtc gagaagattg atacgcttat    3300
```

```
ccaaatgggt tcatttttgc ccgagggata caaattagtc gcagttcgac attgtggaaa    3360
acaaaattta gtcaaagaaa atacgttaat tcacgcaaaa accagttttg aagtaagtat    3420
ttgtcgtgag ttaaaagtaa aaatttaggg ggaaatatta atggcatttg aagagaattt    3480
atattgtgat tatacaccgg gagctgctaa agcggtcgcg gggaaagatg taattttagc    3540 agttttttaac gcagcggggg ataaactatt ggctgttgcg ggccaacaag gtctgactgt    3600
aaaccgttct aaagatagta ttgaaattac atccaaagat acagtgggcg gatgaaaatc    3660
caaaattggc ggtatgaaag aatggtcaat tgaaaatgac gggttatatg tcgctgatgc    3720
agagtctcac aaagaattgg cgaaatattt cgaaagtgat agcccagttt gcgtgaaaat    3780
cattaatcaa gcatctaaaa aaggtctttt cggtggtttg gcaattgtag ctgactatag    3840
ttttgaagcg cctttttgatg aagcgatgac ttactctgta aaactagacg gaatgggcgc    3900
gcttgttgat ttaacgatta ctgagggcgg cgaccaaatg cccggcgaaa cacctgtagc    3960
accagcagaa taaatagaa agccactgaa ataagtggct ttctcttagg aggaaaataa    4020
atgtttgaag tgaatgatac aacttatatt ttacgattta ataaacaaaa agttaaaacg    4080
gtggaattaa catcagggat tagtttagtt gcagctttga ctgcgaataa agggattttg    4140
agctatcaag tgattgaaac gctatttgtt tcaggacttg tggaagaaaa aggcttagta    4200
cctgtaaaac aaaagaagc cttggagatt ttcgataaat tagtagaaga acaaggctta    4260
atttccctta atgtagctgt tattgagaaa ttgcaagagg atatgggttt tttgttccgt    4320
taaaacagat tgaatttgag tattttggtg ctgaggacga agaagtggat agtgaaatga    4380
accatgattt tgatttggaa aaacagttcg cttttttttgt agtcaatttt caaatgtcca    4440
agcatgattt tgaagaactt actgaagtgg agaaaaattt catcatgaaa gaatgggaaa    4500
acaaggtgat ttttgaatct actatgcttc gaaatgcagt tttaaatgcg gaacaaaatc    4560
tcaatcgaaa acgaaattca cgttttatcg acttgcataa aaaacgtcag aagaaagccg    4620
atgttaatta tacagtaaat gcacttcaag caatttccga taatgaagcg aaggaaggta    4680
aagcgtggat tgatcggatt tatggtgcaa atgggttgcg aagacctaaa aataaagaag    4740 aaaggggggaa aatgaatggc ggagtctaaa agtattacat ttgaactgaa cgagagcgtt    4800
ttaacagcgc aagttggcag gctagatgag atggcgatgg ttgtagagcg gcggttttca    4860
gagctcaaaa tgactattga agatgttgga aatgctgatc caggttcgaa aatttccgaa    4920
tctttaggtg ggctgcagtc tgggcttggc acgattagtt cggcgtttgg acagctgggt    4980
tctagtagtg aggcgattac atccggattc ggtactgcgg ttggttctgt tggtggaatc    5040
acggatgcgt ttaaaaatct aggttcaagt gtgcaaaatg gtacgttatt ttcaagcttg    5100
gcgactggaa ttggtggcat gagtacgatg cttggtggag tatctggcgg cgttcaagga    5160
attacaaatc tagctagtgg atttatggaa ttgaagaatc atttaggcgg tttgatgtct    5220
tctattggcg gcgttggtgg aattatgggt aaactgactt ctccaatggg gttagtaatt    5280
atcgggattg ttgcgctagt tgctgctttt acgtacttga tgacgacgaa tgaatcgttc    5340
cgaaataccg tgatgtcagt cgtaacgcag gttgcgcagt tgttcgggca acttgtcgct    5400
agtttaatgc cgattattat gcaaattgtt actgcggtta tgcaaattgg tgccgcgtta    5460
atgccgatgg ttatgcagtt tattagcttt tttgcccagt tgttagctca attaatgcca    5520
tttattaata tgctgatttc tatgcttatg cctgttatta tgcagattgt tcaagttgtt    5580
atgtcgcttg tttcagcgtt attaccaagc attatgacag tgatccaagg cattatgagt    5640
gttattcaat ttttaattcc gataattatg caaatcgcga cggtggttgt acaaattgtt    5700
```

```
gtaacgatta tttcttatat aagtaaaatt atgccgattg ttatgacgat tattggcgtt   5760
attgtttcga ttatcacaac gattattagt tacgtcgtta ttattgcgac gacgattgct   5820
agtgttattg ggaaaattat tagctttatt gcgagtgtta ttacggcggt tatcgggatt   5880
gtgcaaccaa ttattgcctt tattaccaat atctttacga ctatcgtgac aattattggt   5940
gcagctttcc aaatggtatt tactgttgca tccaaaattt ggaattccat tatgtcgact   6000
atttccggaa ttattgacgg aatcaaagca gtcatcacag gtatttctac tacagtttca   6060
tcagtgttta acggagtgaa gcgcattatt acaggtgttt ttgacggaat caaaagtgct   6120
tggggtggtt taactgattt tgtgggaaat attttcgatg gtgtttcaag tgcaattcaa   6180
acagtggtag acaatgtcaa aggttttgta aacgtggtaa ttcgagggat taatggagcc   6240
attggtttaa ttaataagat tccaggagtt gaaatcggca aaataccgca attaatttcc   6300
ggaacaacaa atttccaagg tggctttgct cgaatgaatg aaggcggccg aggtgaaatg   6360
gttgttttac cgtctggttc tcaagtaatt ccgcacgatg caacgatgaa atacgcaaga   6420
gaaagtgcgc gcggaaataa atcaatgctt tacacgagtc aaggcgctga tttggctaga   6480
gttgaaaatc ttctcgagcg cttactacaa aaaaatcctg taatcaaaat ggatgacaaa   6540
gtggtagctg aggtagttag ccgtaatcaa gctaactcat tgatcagta caactataca   6600 atgggaggtg cagcttattc atgagtgact tgtttttaga attaaatgga aaagtgcatt   6660
cgcttagtga gacatttcca ggtctttctg tacaagaagt ttcgagacaa agtccccagt   6720
taagcatgga aactgctgaa atagctggga ctgatgggt tatcccggga atgacccaat   6780
ttaaaccgtt tatcttttca gcaaaatgta atttgcaagc acttgatatt ccagattatc   6840
atttggcagt cagagaaatt tatgaatttt tatttcaacg ggatagttat tatatttgga   6900
gcgatcaaat gccaggaatt cggtatgagg tgcatcctaa accagttgat tttagtcgag   6960
aatcggatcg tgttggttta ctcactatag aatttgatgt atttaaaggc tatgcggagt   7020
cacgtggcac gagccttgac ccaatgactt ttgaagtgga tttatggcag atgggaatga   7080
atttatcgaa ccgtgatgat ttatttatg ttttagaga aaatacattt cgggtctata   7140
atgcggggag cgaccgtgtt aatccactga tgcgacatga attggatatt gctatgacgg   7200
cgaatgggac accaacgatt cataatctta caacgggaga atccttcgag tatcggaaag   7260
agctacaaaa aacagatgtt ttactgttaa acaatatttc tccacttgtt aataaccgcc   7320
gtgttggaaa agataccaat catgggatta tcacccttga aaaaggctgg aacgattttg   7380 aaaatcaaagg tgtaacggat gtaacgattg ctttttaattt tccgttcatt tatccggtagg   7440 tgatagatat ggattatgtg attattcaaa gtatggacaa agaagtggaa gagattctaa   7500
cagacattga ttacggctcc ttttcctacg attatgaaaa aaatacaagt cgtgctattt   7560
cgtttactgt gaacaaaacg aaacagaatg cagcaatttt tgacttggta ggaaatgaag   7620 caatttttaac atatcaaggg cagcaatttg ttattaaaaa atgtacgcca aaatctattg   7680
gaggaacaat ttcaaagcag attacggccc agcatatttg ttatacagtg caagatcatg   7740
tgcagtataa cgtgaaatct ggacgaaaaa aatattcgat tcaaacggta ttggaatttg   7800
cgttacaaga taatgtacta ggattttctt atgaaattca agggagtttt cctttagttg   7860
aattagagga cttaggaaat aaaaatggct tagagctagt gaatttatgt ttggaagaat   7920
tcggagcaat tttatttgca gataataaaa agctttattt ttacgatgaa aaagttggt   7980 atgtaaggac agagaagcaa tttcgttatt tatataatac agaagaagtt tcggtggata   8040
```

```
cgaacacaga caatttgaag acggagataa aatgttacgg caagcaaaaa gagaatgccg    8100
ataagctgac tggagataat aagtacatgg cggttgtcac gtatacttcg ccaaatgagg    8160
ctatttacgg gaaacgaatg gcaaatgcta aaagtgatga caaaatcacg aacaatgatg    8220
acttattaat ttttgcaaag aagcaaattc tagatgttcc ggagacgcg cttactatcg     8280 cttacaaagg aaaagaacct gtttcagagc gggatgtttg gtatttcatt catgaaccga    8340
tggggtttga aacagaagta aaagtaacga aaattaaatc gagtcatcct tggagtaaga    8400
agtttcaaga aattggcttc agtaattcgc gacgggatat ggtccgaatt caaacgcaaa    8460
ttgctaatca agtgaaaaaa gcgagcgtag atacaaataa aattaattcg ttttcgagca    8520
tcgcaatgaa tgcttatgat tcacgaattt taacggaagt agtaggtgtg gtagatggcg    8580
actgaaatta gagtgttaaa aaatgtagat gatacagttt tctatccgaa gacacatgta    8640
acggccgtgg aaggtttaga ctcggctaca actactacat ctggattaat gcccgccagc    8700
gacaaaacga aattaaatgg aatcgaagct aatgcagaaa aaaacaatgt gactgcaatc    8760
gatattgcca attggaataa aaaacaggac gcaattttgg tttctgaaaa tggttctaat    8820
ttcaaaataa ctgtcacaaa tgctggtgaa ctaaaggcaa caaaagtgga ataggaagga    8880
ggttgcgtat gaagttggat ttatggaaat gggaaatgct tcttcaaggt cgagaattta    8940
gaaataaaac aaatgacaac tggcaaaaat tgatggattg gtccgatttt atttcaacag    9000
gtttaagcgc gatttatgtc tatgtaaata agcggatgc taccttaaat aacaaaattg     9060
ataccgtgga taaagcagta aatgcaaggg ttaatgagct gattagcggg acagagcagc    9120
taagtgaagt ggttgatgcg agatcagatg cgtttggtgc acgatatcct gtgctaagag    9180
aacgtttaaa ccaagaacag cttaacttta gcaaaaagag cacgattcaa tttgatgcga    9240
gtactatcat aagtatggaa aaacaagata ttgggctgct aacaagtaaa aaaatctcag    9300
aagcgcaaac cgtatgtttt ttaaatatat caagcctcga tgaagaagca gatattgttc    9360
ttgaaaaaac aggtgagaca agcttctcag acaatttaac gagcctagtc tttgcgaaaa    9420
ttggaacgaa tgaacgctac caaatggagc cagttggtgc ataaaggagg agtgagcgat    9480
gactgaaata aagcgaatgc tacagacaaa agaagataat tcaaaagaac aatttatcc    9540 agagacgcat gttgcgggga ttgtcgggtt gacagaatat gtgtcaggtc agcttccgac    9600
gggtgtggtc agtgtgaatg gtaaggcagg tcgcgtgtta ctggatgctg aagacgttca    9660
cgctgcaaaa aaaagccaca cccatgaagt cgcaacatac actacggatg gctttatgag    9720 ttctttgat aaacaaaaga ttgatcaatt agtttcaccg gaagctggcg tgacaagcat    9780
aaatggtaaa acagggattg ttgatttatt cgcatcggac ttagatgcag cagagataaa    9840
ccacacgcat gcagaagcaa ctactacaga aagcggtttt ttatcaatcg acgacaaaga    9900
aaaattagat gcgatacaag taatcgcgct ggaaactatt aaggaggtta tagaatgact    9960
aaaattgtaa aaatgtcaga gaagaatgaa catggaactc tagaacaatt ctatccagaa   10020
acacatgcag aggctgttaa aggacttgtg tcggtttcag aggaagagaa acaatttgg    10080 gatcaaaagg aaagtacggc gggtgcagag caaaaagcaa acacagcctt aaatagtgct   10140
aaagattatg tggatacgat aggtgaagga acggtgattt taaaggcgc taaccttatg    10200 ggagctggcc aatcatttaa atgggacgct tctaaactga aatttgggat gactttgtta   10260
tttagtcgct atgatgcggc aaataataca ccgcaagatt attattatca ttctgtattc   10320
ttatctaagg cacaattagt tgagcttgca ggaaaaggta ttttagttca aatgccatca   10380
acgacttatg gagatcgaaa atatctgtat gtttcaacaa ctgggttatc tggacatttt   10440
```

```
gataattcga attatgcggc ttgggctctg cgccaagtaa caattatgta actaaaaagg    10500
aggttttcca tggaagtcat actaaaattc gggattttag gttttggcgc gatatttgga    10560
tacttgtttg gggaagtgga tttattggta aaagtgctgg tgtgctttat tgtagctgac    10620
tatatttctg ggctactcgc ttcagggtat cttggggaac ttagcagcaa aatgggtttc    10680
aaaggaatcg cgaaaaaaat cgctatctta attttagtgg ctattgcgca tcaaatagat    10740
ttgattctgg gaacgcataa tacaacgcgg gatgcggtta tcttttttcta tttagcgaat    10800
gagctgattt ctatcttgga aaatttcgtt cgaatgggaa tgaaggtccc ggaagtattg    10860
aaaaattaa ttttgatttt cgatgcaaag tcaggagagg atgaggaaaa acatgacaaa    10920
gatatggatt gacgctggac acggtggtaa ggattcaggt gcgagtggta atggacttgt    10980
tgaaaaaaat tgggtactaa ctgtagcaaa acaacttcaa acagagttag ttaaagccgg    11040
ttttgaagtg ggaatgacaa gaacaaatga tacattctat gaattaagtg atcgtgcgaa    11100
gaaggcgaat agttttaaag ctgatttatt tatttcgctt cattttaatg ctggtggcgg    11160
taaaggatat gaagattata tttacacatc cgtcccggct gcaacggtag aaatacagaa    11220
aataattcat aaaatatta ttactaaagt tactaaacac ggaatgaatg atcgtggaat    11280
gaagaaagct aatttcgctg tattaagaga aacagcaatg gatgctatct tacttgaagc    11340
tggattttgc gatagcactg atgcattaat tcttgagaag aaagcttatc aaactgatta    11400
ttgtttagga attgtatcag cagtacaaga gattttggg gctatggtaa caaaatatag    11460
ggcaggcaaa tatttgacaa gtgacgatgc tatatcaggc acaaatatta aaggatattt    11520
agaagcagga acaaaggttt ttgtttataa agaaacagaa aaaacgctta atttaactac    11580
tacaaagggt gttccaggaa gctgggtttt aaaaacagaa gttaatacag gaaaaagata    11640
a                                                                   11641
```

<210> SEQ ID NO 2
<211> LENGTH: 231
<212> TYPE: PRT
<213> ORGANISM: Listeria monocytogenes strain 1/2a 35152

<400> SEQUENCE: 2

```
Met Leu His Thr Ile Asp Phe Ser Asp Ile Phe Ser Ser Asp Tyr Ser
1               5                  10                  15

Ser Lys Ile Ser Phe Lys Lys Gly Glu Ile Ile His Ser Tyr Arg Asp
            20                  25                  30

Tyr Glu Glu Lys Ala Pro Gln Ile Gly Ala Ile Leu Glu Gly Lys Ala
        35                  40                  45

Val Leu Glu Gly Pro Thr Asn Glu Gly Arg Trp Met Ile Asn Ala Leu
    50                  55                  60

Ile Gly Gln His Ala Leu Phe Gly Met Glu Ser Leu Leu Glu Thr Lys
65                  70                  75                  80

Thr Ala Pro Glu Leu Thr Glu Tyr Arg Val Arg Ala Leu Glu Asn Gly
                85                  90                  95

Thr Val Leu Phe Ile Asp Arg Glu Phe Leu Leu Asn Tyr Leu Tyr Ala
            100                 105                 110

Asn Pro Gln Phe Phe His Leu Ile Leu Asp Glu Val Ile Val Arg Tyr
        115                 120                 125

Leu Phe Thr Ser Lys Asn Tyr Lys Asn Ile Asn Gln Ala Pro Ile Val
    130                 135                 140

Lys Val Thr Arg Ile Leu Val Glu Ile Ile Glu Leu Leu His Leu His
```

```
145                 150                 155                 160
Gln Thr Glu Gly Ser Ile Glu Leu Pro Val Tyr Val Thr Gln Thr Phe
                165                 170                 175

Leu Ala Asp Tyr Cys Arg Ser Arg Ala Arg Val Thr Glu Val Leu
            180                 185                 190

Glu Glu Leu Arg Glu Ser Gly Leu Leu Ser Lys Lys Pro Ile Thr
            195                 200                 205

Ile Ser Ser His Glu Asn Leu Leu Asp Gln Val Asp Ser Phe Gln Thr
    210                 215                 220

Gly Asn Gly Leu Leu Thr Arg
225                 230

<210> SEQ ID NO 3
<211> LENGTH: 150
<212> TYPE: PRT
<213> ORGANISM: Listeria monocytogenes strain 1/2a 35152

<400> SEQUENCE: 3

Leu Tyr Glu Lys Leu Val Asn Lys Tyr Gln Asp Glu Val Thr Ile Arg
1               5                   10                  15

Glu Glu Lys Met Pro Tyr Lys Leu Pro Gly Leu Tyr Leu Asn Gly Met
            20                  25                  30

Ile Phe Ile Ser Lys Asp Gln Ser Ser Ile Glu Lys Gly Cys Val Leu
        35                  40                  45

Val Glu Glu Leu Met His Tyr Lys Tyr Thr Val Gly Asn Ile Thr Lys
    50                  55                  60

Gln Glu Thr Ile Met Asp Lys Lys Gln Glu Ile Phe Ala Arg Arg Lys
65                  70                  75                  80

Gly Tyr Glu Glu Leu Ile Pro Leu Asp Asp Ile Ile Ala Cys Phe Tyr
                85                  90                  95

Leu Gly Leu Arg Glu Tyr Phe Glu Val Ala Glu Phe Leu Glu Val Thr
            100                 105                 110

Glu Glu Phe Leu Arg His Thr Val Ser His Tyr Ala Glu Lys Tyr Gly
        115                 120                 125

Pro Met Tyr Asp Tyr Gly Gly Tyr Phe Ile Asn Phe Gly Asn Ser Ile
    130                 135                 140

Asp Val Tyr Lys Lys Phe
145                 150

<210> SEQ ID NO 4
<211> LENGTH: 111
<212> TYPE: PRT
<213> ORGANISM: Listeria monocytogenes strain 1/2a 35152

<400> SEQUENCE: 4

Met Glu Leu Asn Lys Phe Val Gly Asn Lys Ile Lys Gln Tyr Arg Glu
1               5                   10                  15

Glu Arg Gly Leu Asn Gln Glu Ala Leu Ala Glu Lys Leu His Thr Thr
            20                  25                  30

Arg Gln Thr Ile Ser Arg Tyr Glu Asn Gly Asp Arg Lys Ala Asn Gln
        35                  40                  45

Asp Val Leu Phe Glu Leu Ala Lys Ile Phe Asn Lys Arg Leu Asp Asp
    50                  55                  60

Phe Phe Pro Glu Arg Asn Leu Pro Pro Val Asp Glu Arg Leu Val Thr
65                  70                  75                  80

Ile Ala Ala His Ile Asp Asp Asp Val Thr Glu Glu Glu Met Arg Asp
```

```
                          85                  90                  95

Ile Leu Ala Tyr Ile Glu Met Lys Lys Lys Leu His Arg Gly Met
                100                 105                 110

<210> SEQ ID NO 5
<211> LENGTH: 142
<212> TYPE: PRT
<213> ORGANISM: Listeria monocytogenes strain 1/2a 35152

<400> SEQUENCE: 5

Met Asp Arg Lys Leu Leu Lys Glu Lys Gln Ile Gln Leu Ile Phe Gln
1               5                   10                  15

Leu Glu Gln Glu Glu Asn Arg Phe Ile Arg Lys Arg Leu Ile Glu Glu
                20                  25                  30

Leu Glu Phe Phe Glu Ala Leu Gly Asp Arg Glu Lys Gly Leu Leu Thr
            35                  40                  45

Ala Glu Gln Lys Leu Leu Ile Leu Thr Pro Ser Glu Tyr Arg Glu Tyr
        50                  55                  60

Lys Arg Thr Lys Ser Asp Val Gln Ile Ser Arg Ile Ile Gly Val Ser
65                  70                  75                  80

Arg Ser Ser Leu Ala Glu Trp Lys Arg Lys Lys Gly Leu Asn Arg Lys
                85                  90                  95

Lys Ser Gln Pro Val Gln Gln Glu Met Ile Asp Val Leu Ala Phe His
                100                 105                 110

Leu Asp Lys Thr Lys Glu Glu Ile Gly Ala Leu Pro Ala Ser Ala Ile
            115                 120                 125

Glu Cys Gln Tyr Glu Ala Phe Val Ile Asn Glu Ala Asn Asn
        130                 135                 140

<210> SEQ ID NO 6
<211> LENGTH: 138
<212> TYPE: PRT
<213> ORGANISM: Listeria monocytogenes strain 1/2a 35152

<400> SEQUENCE: 6

Met Gln Val Leu Val Leu Pro Glu Asn Lys Asp Ile Asn Tyr Ile Lys
1               5                   10                  15

Thr Val His Glu Val Lys Arg Phe Phe Ala Asp Phe Glu Arg Phe Arg
                20                  25                  30

Met Ile Thr Gly Leu Ser Lys Lys Pro His Leu Leu Arg Asn Gly Phe
            35                  40                  45

Leu Glu Glu Pro Gln Phe Glu Pro Val Ala Phe Ser Ala Arg His Asn
        50                  55                  60

Lys Glu Val Ile Leu Glu Ala Arg Trp Leu Val Glu Lys Tyr Thr Glu
65                  70                  75                  80

Met Leu Asn Gln Met Asp Asp Leu Tyr Arg Thr Ile Leu Met Glu Cys
                85                  90                  95

Tyr Val Glu Arg Lys Gln Asp Val Ala Val Met Met Asp Leu Pro Tyr
                100                 105                 110

Glu Ile Ala Gln Phe Lys Arg Ile Lys Lys Arg Ala Val Leu Glu Leu
            115                 120                 125

Ala Thr Leu Met Gly Ile Leu Val Arg Lys
        130                 135

<210> SEQ ID NO 7
<211> LENGTH: 126
<212> TYPE: PRT
```

<213> ORGANISM: Listeria monocytogenes strain 1/2a 35152

<400> SEQUENCE: 7

```
Leu Ser Phe Met Arg Val Leu Glu Ala Val Arg Thr Met Leu Gln Glu
1               5                   10                  15

Lys Gly Gly Leu Asp Val Ser Ile Val Met Arg Asn Gln Val Glu Met
            20                  25                  30

Pro Thr Thr Met Ile Glu Met Ile Asp Gln Glu Glu Glu Glu Ser Gln
        35                  40                  45

Thr Ala Trp Lys Glu Lys Tyr Arg Phe Ala Ile His His Tyr Thr Asn
    50                  55                  60

Glu Gln Asp Leu Ala Gly Val Glu Lys Ile Asp Thr Leu Ile Gln Met
65                  70                  75                  80

Gly Phe Ile Leu Pro Glu Gly Tyr Lys Leu Val Ala Val Arg His Cys
                85                  90                  95

Gly Lys Gln Asn Leu Val Lys Glu Asn Thr Leu Ile His Ala Lys Thr
            100                 105                 110

Ser Phe Glu Val Ser Ile Cys Arg Glu Leu Lys Val Lys Ile
        115                 120                 125
```

<210> SEQ ID NO 8
<211> LENGTH: 170
<212> TYPE: PRT
<213> ORGANISM: Listeria monocytogenes strain 1/2a 35152

<400> SEQUENCE: 8

```
Met Ala Phe Glu Glu Asn Leu Tyr Cys Asp Tyr Thr Pro Gly Ala Ala
1               5                   10                  15

Lys Ala Val Ala Gly Lys Asp Val Ile Leu Ala Val Phe Asn Ala Ala
            20                  25                  30

Gly Asp Lys Leu Leu Ala Val Ala Gly Gln Gln Gly Leu Thr Val Asn
        35                  40                  45

Arg Ser Lys Asp Ser Ile Glu Ile Thr Ser Lys Asp Thr Val Gly Gly
    50                  55                  60

Trp Lys Ser Lys Ile Gly Gly Met Lys Glu Trp Ser Ile Glu Asn Asp
65                  70                  75                  80

Gly Leu Tyr Val Ala Asp Ala Glu Ser His Lys Glu Leu Ala Lys Tyr
                85                  90                  95

Phe Glu Ser Asp Ser Pro Val Cys Val Lys Ile Ile Asn Gln Ala Ser
            100                 105                 110

Lys Lys Gly Leu Phe Gly Gly Leu Ala Ile Val Ala Asp Tyr Ser Phe
        115                 120                 125

Glu Ala Pro Phe Asp Glu Ala Met Thr Tyr Ser Val Lys Leu Asp Gly
    130                 135                 140

Met Gly Ala Leu Val Asp Leu Thr Ile Thr Glu Gly Gly Asp Gln Met
145                 150                 155                 160

Pro Gly Glu Thr Pro Val Ala Pro Ala Glu
                165                 170
```

<210> SEQ ID NO 9
<211> LENGTH: 100
<212> TYPE: PRT
<213> ORGANISM: Listeria monocytogenes strain 1/2a 35152

<400> SEQUENCE: 9

```
Met Phe Glu Val Asn Asp Thr Thr Tyr Ile Leu Arg Phe Asn Lys Gln
1               5                   10                  15
```

```
Lys Val Lys Thr Val Glu Leu Thr Ser Gly Ile Ser Leu Val Ala Ala
                20                  25                  30

Leu Thr Ala Asn Lys Gly Ile Leu Ser Tyr Gln Val Ile Glu Thr Leu
            35                  40                  45

Phe Val Ser Gly Leu Val Glu Glu Lys Gly Leu Val Pro Val Lys Gln
50                  55                  60

Lys Glu Ala Leu Glu Ile Phe Asp Lys Leu Val Glu Glu Gln Gly Leu
65                  70                  75                  80

Ile Ser Leu Asn Val Ala Val Ile Glu Lys Leu Gln Glu Asp Met Gly
                85                  90                  95

Phe Leu Phe Arg
            100

<210> SEQ ID NO 10
<211> LENGTH: 130
<212> TYPE: PRT
<213> ORGANISM: Listeria monocytogenes strain 1/2a 35152

<400> SEQUENCE: 10

Met Asn His Asp Phe Asp Leu Glu Lys Gln Phe Ala Phe Val Val
1               5                   10                  15

Asn Phe Gln Met Ser Lys His Asp Phe Glu Glu Leu Thr Glu Val Glu
                20                  25                  30

Lys Asn Phe Ile Met Lys Glu Trp Glu Asn Lys Val Ile Phe Glu Ser
            35                  40                  45

Thr Met Leu Arg Asn Ala Val Leu Asn Ala Gln Asn Leu Asn Arg
50                  55                  60

Lys Arg Asn Ser Arg Phe Ile Asp Leu His Lys Lys Arg Gln Lys Lys
65                  70                  75                  80

Ala Asp Val Asn Tyr Thr Val Asn Ala Leu Gln Ala Ile Ser Asp Asn
                85                  90                  95

Glu Ala Lys Glu Gly Lys Ala Trp Ile Asp Arg Ile Tyr Gly Ala Asn
            100                 105                 110

Gly Leu Arg Arg Pro Lys Asn Lys Glu Glu Arg Gly Lys Met Asn Gly
        115                 120                 125

Gly Val
    130

<210> SEQ ID NO 11
<211> LENGTH: 622
<212> TYPE: PRT
<213> ORGANISM: Listeria monocytogenes strain 1/2a 35152

<400> SEQUENCE: 11

Met Ala Glu Ser Lys Ser Ile Thr Phe Glu Leu Asn Glu Ser Val Leu
1               5                   10                  15

Thr Ala Gln Val Gly Arg Leu Asp Glu Met Ala Met Val Val Glu Arg
                20                  25                  30

Arg Phe Ser Glu Leu Lys Met Thr Ile Glu Asp Val Gly Asn Ala Asp
            35                  40                  45

Pro Gly Ser Lys Ile Ser Glu Ser Leu Gly Gly Leu Gln Ser Gly Leu
        50                  55                  60

Gly Thr Ile Ser Ser Ala Phe Gly Gln Leu Gly Ser Ser Glu Ala
65                  70                  75                  80

Ile Thr Ser Gly Phe Gly Thr Ala Val Gly Ser Val Gly Gly Ile Thr
                85                  90                  95
```

```
Asp Ala Phe Lys Asn Leu Gly Ser Ser Val Gln Asn Gly Thr Leu Phe
            100                 105                 110

Ser Ser Leu Ala Thr Gly Ile Gly Met Ser Thr Met Leu Gly Gly
            115                 120                 125

Val Ser Gly Gly Val Gln Gly Ile Thr Asn Leu Ala Ser Gly Phe Met
130                 135                 140

Glu Leu Lys Asn His Leu Gly Gly Leu Met Ser Ser Ile Gly Gly Val
145                 150                 155                 160

Gly Gly Ile Met Gly Lys Leu Thr Ser Pro Met Gly Leu Val Ile Ile
                165                 170                 175

Gly Ile Val Ala Leu Val Ala Ala Phe Thr Tyr Leu Met Thr Thr Asn
            180                 185                 190

Glu Ser Phe Arg Asn Thr Val Met Ser Val Val Thr Gln Val Ala Gln
            195                 200                 205

Leu Phe Gly Gln Leu Val Ala Ser Leu Met Pro Ile Ile Met Gln Ile
            210                 215                 220

Val Thr Ala Val Met Gln Ile Gly Ala Ala Leu Met Pro Met Val Met
225                 230                 235                 240

Gln Phe Ile Ser Phe Ala Gln Leu Leu Ala Gln Leu Met Pro Phe
            245                 250                 255

Ile Asn Met Leu Ile Ser Met Leu Met Pro Val Ile Met Gln Ile Val
            260                 265                 270

Gln Val Val Met Ser Leu Val Ser Ala Leu Leu Pro Ser Ile Met Thr
            275                 280                 285

Val Ile Gln Gly Ile Met Ser Val Ile Gln Phe Leu Ile Pro Ile Ile
            290                 295                 300

Met Gln Ile Ala Thr Val Val Val Gln Ile Val Thr Ile Ile Ser
305                 310                 315                 320

Tyr Ile Ser Lys Ile Met Pro Ile Val Met Thr Ile Ile Gly Val Ile
            325                 330                 335

Val Ser Ile Ile Thr Thr Ile Ile Ser Tyr Val Val Ile Ile Ala Thr
            340                 345                 350

Thr Ile Ala Ser Val Ile Gly Lys Ile Ile Ser Phe Ile Ala Ser Val
            355                 360                 365

Ile Thr Ala Val Ile Gly Ile Val Gln Pro Ile Ile Ala Phe Ile Thr
            370                 375                 380

Asn Ile Phe Thr Thr Ile Val Thr Ile Ile Gly Ala Ala Phe Gln Met
385                 390                 395                 400

Val Phe Thr Val Ala Ser Lys Ile Trp Asn Ser Ile Met Ser Thr Ile
            405                 410                 415

Ser Gly Ile Ile Asp Gly Ile Lys Ala Val Ile Thr Gly Ile Ser Thr
            420                 425                 430

Thr Val Ser Ser Val Phe Asn Gly Val Lys Arg Ile Ile Thr Gly Val
            435                 440                 445

Phe Asp Gly Ile Lys Ser Ala Trp Gly Gly Leu Thr Asp Phe Val Gly
            450                 455                 460

Asn Ile Phe Asp Gly Val Ser Ser Ala Ile Gln Thr Val Val Asp Asn
465                 470                 475                 480

Val Lys Gly Phe Val Asn Val Val Ile Arg Gly Ile Asn Gly Ala Ile
            485                 490                 495

Gly Leu Ile Asn Lys Ile Pro Gly Val Glu Ile Gly Lys Ile Pro Gln
            500                 505                 510
```

```
Leu Ile Ser Gly Thr Thr Asn Phe Gln Gly Gly Phe Ala Arg Met Asn
        515                 520                 525

Glu Gly Gly Arg Gly Glu Met Val Val Leu Pro Ser Gly Ser Gln Val
    530                 535                 540

Ile Pro His Asp Ala Thr Met Lys Tyr Ala Arg Glu Ser Ala Arg Gly
545                 550                 555                 560

Asn Lys Ser Met Leu Tyr Thr Ser Gln Gly Ala Asp Leu Ala Arg Val
            565                 570                 575

Glu Asn Leu Leu Glu Arg Leu Leu Gln Lys Asn Pro Val Ile Lys Met
        580                 585                 590

Asp Asp Lys Val Val Ala Glu Val Val Ser Arg Asn Gln Ala Asn Ser
    595                 600                 605

Phe Asp Gln Tyr Asn Tyr Thr Met Gly Gly Ala Ala Tyr Ser
    610                 615                 620

<210> SEQ ID NO 12
<211> LENGTH: 272
<212> TYPE: PRT
<213> ORGANISM: Listeria monocytogenes strain 1/2a 35152

<400> SEQUENCE: 12

Met Ser Asp Leu Phe Leu Glu Leu Asn Gly Lys Val His Ser Leu Ser
1               5                   10                  15

Glu Thr Phe Pro Gly Leu Ser Val Gln Glu Val Ser Arg Gln Ser Pro
            20                  25                  30

Gln Leu Ser Met Glu Thr Ala Glu Ile Ala Gly Thr Asp Gly Val Ile
        35                  40                  45

Pro Gly Met Thr Gln Phe Lys Pro Phe Ile Phe Ser Ala Lys Cys Asn
50                  55                  60

Leu Gln Ala Leu Asp Ile Pro Asp Tyr His Leu Ala Val Arg Glu Ile
65                  70                  75                  80

Tyr Glu Phe Leu Phe Gln Arg Asp Ser Tyr Tyr Ile Trp Ser Asp Gln
                85                  90                  95

Met Pro Gly Ile Arg Tyr Glu Val His Pro Lys Pro Val Asp Phe Ser
            100                 105                 110

Arg Glu Ser Asp Arg Val Gly Leu Leu Thr Ile Glu Phe Asp Val Phe
        115                 120                 125

Lys Gly Tyr Ala Glu Ser Arg Gly Thr Ser Leu Asp Pro Met Thr Phe
    130                 135                 140

Glu Val Asp Leu Trp Gln Met Gly Met Asn Leu Ser Asn Arg Asp Asp
145                 150                 155                 160

Leu Phe Tyr Val Phe Arg Glu Asn Thr Phe Arg Val Tyr Asn Ala Gly
                165                 170                 175

Ser Asp Arg Val Asn Pro Leu Met Arg His Glu Leu Asp Ile Ala Met
            180                 185                 190

Thr Ala Asn Gly Thr Pro Thr Ile His Asn Leu Thr Thr Gly Glu Ser
        195                 200                 205

Phe Glu Tyr Arg Lys Glu Leu Gln Lys Thr Asp Val Leu Leu Leu Asn
    210                 215                 220

Asn Ile Tyr Pro Leu Val Asn Asn Arg Arg Val Gly Lys Asp Thr Asn
225                 230                 235                 240

His Gly Ile Ile Thr Leu Glu Lys Gly Trp Asn Asp Phe Glu Ile Lys
                245                 250                 255

Gly Val Thr Asp Val Thr Ile Ala Phe Asn Phe Pro Phe Ile Tyr Arg
            260                 265                 270
```

<210> SEQ ID NO 13
<211> LENGTH: 378
<212> TYPE: PRT
<213> ORGANISM: Listeria monocytogenes strain 1/2a 35152

<400> SEQUENCE: 13

Met Asp Tyr Val Ile Ile Gln Ser Met Asp Lys Glu Val Glu Glu Ile
1               5                   10                  15

Leu Thr Asp Ile Asp Tyr Gly Ser Phe Ser Tyr Asp Tyr Glu Lys Asn
            20                  25                  30

Thr Ser Arg Ala Ile Ser Phe Thr Val Asn Lys Thr Lys Gln Asn Ala
        35                  40                  45

Ala Ile Phe Asp Leu Val Gly Asn Glu Ala Ile Leu Thr Tyr Gln Gly
    50                  55                  60

Gln Gln Phe Val Ile Lys Lys Cys Thr Pro Lys Ser Ile Gly Gly Thr
65                  70                  75                  80

Ile Ser Lys Gln Ile Thr Ala Gln His Ile Cys Tyr Thr Val Gln Asp
                85                  90                  95

His Val Gln Tyr Asn Val Lys Ser Gly Arg Lys Lys Tyr Ser Ile Gln
            100                 105                 110

Thr Val Leu Glu Phe Ala Leu Gln Asp Asn Val Leu Gly Phe Ser Tyr
        115                 120                 125

Glu Ile Gln Gly Ser Phe Pro Leu Val Glu Leu Glu Asp Leu Gly Asn
    130                 135                 140

Lys Asn Gly Leu Glu Leu Val Asn Leu Cys Leu Glu Glu Phe Gly Ala
145                 150                 155                 160

Ile Leu Phe Ala Asp Asn Lys Lys Leu Tyr Phe Tyr Asp Glu Lys Ser
                165                 170                 175

Trp Tyr Val Arg Thr Glu Lys Gln Phe Arg Tyr Leu Tyr Asn Thr Glu
            180                 185                 190

Glu Val Ser Val Asp Thr Asn Thr Asp Asn Leu Lys Thr Glu Ile Lys
        195                 200                 205

Cys Tyr Gly Lys Gln Lys Glu Asn Ala Asp Lys Leu Thr Gly Asp Asn
    210                 215                 220

Lys Tyr Met Ala Val Val Thr Tyr Thr Ser Pro Asn Glu Ala Ile Tyr
225                 230                 235                 240

Gly Lys Arg Met Ala Asn Ala Lys Ser Asp Asp Lys Ile Thr Asn Asn
                245                 250                 255

Asp Asp Leu Leu Ile Phe Ala Lys Lys Gln Ile Leu Asp Val Pro Glu
            260                 265                 270

Thr Ala Leu Thr Ile Ala Tyr Lys Gly Lys Glu Pro Val Ser Glu Arg
        275                 280                 285

Asp Val Trp Tyr Phe Ile His Glu Pro Met Gly Phe Glu Thr Glu Val
    290                 295                 300

Lys Val Thr Lys Ile Lys Ser Ser His Pro Trp Ser Lys Lys Phe Gln
305                 310                 315                 320

Glu Ile Gly Phe Ser Asn Ser Arg Arg Asp Met Val Arg Ile Gln Thr
                325                 330                 335

Gln Ile Ala Asn Gln Val Lys Lys Ala Ser Val Asp Thr Asn Lys Ile
            340                 345                 350

Asn Ser Phe Ser Ser Ile Ala Met Asn Ala Tyr Asp Ser Arg Ile Leu
        355                 360                 365

Thr Glu Val Val Gly Val Val Asp Gly Asp

```
                    370             375
```

<210> SEQ ID NO 14
<211> LENGTH: 99
<212> TYPE: PRT
<213> ORGANISM: Listeria monocytogenes strain 1/2a 35152

<400> SEQUENCE: 14

```
Met Ala Thr Glu Ile Arg Val Leu Lys Asn Val Asp Asp Thr Val Phe
1               5                   10                  15

Tyr Pro Lys Thr His Val Thr Ala Val Glu Gly Leu Asp Ser Ala Thr
            20                  25                  30

Thr Thr Thr Ser Gly Leu Met Pro Ala Ser Asp Lys Thr Lys Leu Asn
        35                  40                  45

Gly Ile Glu Ala Asn Ala Glu Lys Asn Asn Val Thr Ala Ile Asp Ile
    50                  55                  60

Ala Asn Trp Asn Lys Lys Gln Asp Ala Ile Leu Val Ser Glu Asn Gly
65                  70                  75                  80

Ser Asn Phe Lys Ile Thr Val Thr Asn Ala Gly Glu Leu Lys Ala Thr
                85                  90                  95

Lys Val Glu
```

<210> SEQ ID NO 15
<211> LENGTH: 191
<212> TYPE: PRT
<213> ORGANISM: Listeria monocytogenes strain 1/2a 35152

<400> SEQUENCE: 15

```
Met Lys Leu Asp Leu Trp Lys Trp Glu Met Leu Leu Gln Gly Arg Glu
1               5                   10                  15

Phe Arg Asn Lys Thr Asn Asp Asn Trp Gln Lys Leu Met Asp Trp Ser
            20                  25                  30

Asp Phe Ile Ser Thr Gly Leu Ser Ala Ile Tyr Val Tyr Val Asn Lys
        35                  40                  45

Ala Asp Ala Thr Leu Asn Asn Lys Ile Asp Thr Val Asp Lys Ala Val
    50                  55                  60

Asn Ala Arg Val Asn Glu Leu Ile Ser Gly Thr Glu Gln Leu Ser Glu
65                  70                  75                  80

Val Val Asp Ala Arg Ser Asp Ala Phe Gly Ala Arg Tyr Pro Val Leu
                85                  90                  95

Arg Glu Arg Leu Asn Gln Glu Gln Leu Asn Phe Ser Lys Lys Ser Thr
            100                 105                 110

Ile Gln Phe Asp Ala Ser Thr Ile Ile Ser Met Glu Lys Gln Asp Ile
        115                 120                 125

Gly Leu Leu Thr Ser Lys Lys Ile Ser Glu Ala Gln Thr Val Cys Phe
    130                 135                 140

Leu Asn Ile Ser Ser Leu Asp Glu Glu Ala Asp Ile Val Leu Glu Lys
145                 150                 155                 160

Thr Gly Glu Thr Ser Phe Ser Asp Asn Leu Thr Ser Leu Val Phe Ala
                165                 170                 175

Lys Ile Gly Thr Asn Glu Arg Tyr Gln Met Glu Pro Val Gly Ala
            180                 185                 190
```

<210> SEQ ID NO 16
<211> LENGTH: 159
<212> TYPE: PRT
<213> ORGANISM: Listeria monocytogenes strain 1/2a 35152

<400> SEQUENCE: 16

| Met | Thr | Glu | Ile | Lys | Arg | Met | Leu | Gln | Thr | Lys | Glu | Asp | Asn | Ser | Lys |
| 1 | | | | 5 | | | | | 10 | | | | | 15 | |

| Glu | Gln | Phe | Tyr | Pro | Glu | Thr | His | Val | Ala | Gly | Ile | Val | Gly | Leu | Thr |
| | | | 20 | | | | | 25 | | | | | 30 | | |

| Glu | Tyr | Val | Ser | Gly | Gln | Leu | Pro | Thr | Gly | Val | Val | Ser | Val | Asn | Gly |
| | | | 35 | | | | | 40 | | | | | 45 | | |

| Lys | Ala | Gly | Arg | Val | Leu | Leu | Asp | Ala | Glu | Asp | Val | His | Ala | Ala | Lys |
| | 50 | | | | | 55 | | | | | 60 | | | | |

| Lys | Ser | His | Thr | His | Glu | Val | Ala | Thr | Tyr | Thr | Thr | Asp | Gly | Phe | Met |
| 65 | | | | | 70 | | | | | 75 | | | | | 80 |

| Ser | Ser | Phe | Asp | Lys | Gln | Lys | Ile | Asp | Gln | Leu | Val | Ser | Pro | Glu | Ala |
| | | | | 85 | | | | | 90 | | | | | 95 | |

| Gly | Val | Thr | Ser | Ile | Asn | Gly | Lys | Thr | Gly | Ile | Val | Asp | Leu | Phe | Ala |
| | | | 100 | | | | | 105 | | | | | 110 | | |

| Ser | Asp | Leu | Asp | Ala | Ala | Glu | Ile | Asn | His | Thr | His | Ala | Glu | Ala | Thr |
| | | | 115 | | | | | 120 | | | | | 125 | | |

| Thr | Thr | Glu | Ser | Gly | Phe | Leu | Ser | Ile | Asp | Asp | Lys | Glu | Lys | Leu | Asp |
| | 130 | | | | | 135 | | | | | 140 | | | | |

| Ala | Ile | Gln | Val | Ile | Ala | Leu | Glu | Thr | Ile | Lys | Glu | Val | Ile | Glu | |
| 145 | | | | | 150 | | | | | 155 | | | | | |

<210> SEQ ID NO 17
<211> LENGTH: 178
<212> TYPE: PRT
<213> ORGANISM: Listeria monocytogenes strain 1/2a 35152

<400> SEQUENCE: 17

| Met | Thr | Lys | Ile | Val | Lys | Met | Ser | Glu | Lys | Asn | Glu | His | Gly | Thr | Leu |
| 1 | | | | 5 | | | | | 10 | | | | | 15 | |

| Glu | Gln | Phe | Tyr | Pro | Glu | Thr | His | Ala | Glu | Ala | Val | Lys | Gly | Leu | Val |
| | | | 20 | | | | | 25 | | | | | 30 | | |

| Ser | Val | Ser | Glu | Glu | Glu | Lys | Thr | Ile | Trp | Asp | Gln | Lys | Glu | Ser | Thr |
| | | | 35 | | | | | 40 | | | | | 45 | | |

| Ala | Gly | Ala | Glu | Gln | Lys | Ala | Asn | Thr | Ala | Leu | Asn | Ser | Ala | Lys | Asp |
| | 50 | | | | | 55 | | | | | 60 | | | | |

| Tyr | Val | Asp | Thr | Ile | Gly | Glu | Gly | Thr | Val | Ile | Phe | Lys | Gly | Ala | Asn |
| 65 | | | | | 70 | | | | | 75 | | | | | 80 |

| Leu | Met | Gly | Ala | Gly | Gln | Ser | Phe | Lys | Trp | Asp | Ala | Ser | Lys | Leu | Lys |
| | | | | 85 | | | | | 90 | | | | | 95 | |

| Phe | Gly | Met | Thr | Leu | Leu | Phe | Ser | Arg | Tyr | Asp | Ala | Ala | Asn | Asn | Thr |
| | | | 100 | | | | | 105 | | | | | 110 | | |

| Pro | Gln | Asp | Tyr | Tyr | His | Ser | Val | Phe | Leu | Ser | Lys | Ala | Gln | Leu | |
| | | | 115 | | | | | 120 | | | | | 125 | | |

| Val | Glu | Leu | Ala | Gly | Lys | Gly | Ile | Leu | Val | Gln | Met | Pro | Ser | Thr | Thr |
| | 130 | | | | | 135 | | | | | 140 | | | | |

| Tyr | Gly | Asp | Arg | Lys | Tyr | Leu | Tyr | Val | Ser | Thr | Thr | Gly | Leu | Ser | Gly |
| 145 | | | | | 150 | | | | | 155 | | | | | 160 |

| His | Phe | Asp | Asn | Ser | Asn | Tyr | Ala | Ala | Trp | Ala | Leu | Arg | Gln | Val | Thr |
| | | | | 165 | | | | | 170 | | | | | 175 | |

| Ile | Met |
| | |

<210> SEQ ID NO 18
<211> LENGTH: 140

```
<212> TYPE: PRT
<213> ORGANISM: Listeria monocytogenes strain 1/2a 35152

<400> SEQUENCE: 18

Met Glu Val Ile Leu Lys Phe Gly Ile Leu Gly Phe Ala Ile Phe
1               5                   10                  15

Gly Tyr Leu Phe Gly Glu Val Asp Leu Val Lys Val Leu Val Cys
                20                  25                  30

Phe Ile Val Ala Asp Tyr Ile Ser Gly Leu Leu Ala Ser Gly Tyr Leu
                35                  40                  45

Gly Glu Leu Ser Ser Lys Met Gly Phe Lys Gly Ile Ala Lys Lys Ile
            50                  55                  60

Ala Ile Leu Ile Leu Val Ala Ile Ala His Gln Ile Asp Leu Ile Leu
65                  70                  75                  80

Gly Thr His Asn Thr Thr Arg Asp Ala Val Ile Phe Phe Tyr Leu Ala
                85                  90                  95

Asn Glu Leu Ile Ser Ile Leu Glu Asn Phe Val Arg Met Gly Met Lys
                100                 105                 110

Val Pro Glu Val Leu Lys Asn Leu Ile Leu Ile Phe Asp Ala Lys Ser
            115                 120                 125

Gly Glu Asp Glu Glu Lys His Asp Lys Asp Met Asp
        130                 135                 140

<210> SEQ ID NO 19
<211> LENGTH: 246
<212> TYPE: PRT
<213> ORGANISM: Listeria monocytogenes strain 1/2a 35152

<400> SEQUENCE: 19

Met Arg Lys Asn Met Thr Lys Ile Trp Ile Asp Ala Gly His Gly Gly
1               5                   10                  15

Lys Asp Ser Gly Ala Ser Gly Asn Gly Leu Val Glu Lys Asn Trp Val
                20                  25                  30

Leu Thr Val Ala Lys Gln Leu Gln Thr Glu Leu Val Lys Ala Gly Phe
            35                  40                  45

Glu Val Gly Met Thr Arg Thr Asn Asp Thr Phe Tyr Glu Leu Ser Asp
        50                  55                  60

Arg Ala Lys Lys Ala Asn Ser Phe Lys Ala Asp Leu Phe Ile Ser Leu
65                  70                  75                  80

His Phe Asn Ala Gly Gly Gly Lys Gly Tyr Glu Asp Tyr Ile Tyr Thr
                85                  90                  95

Ser Val Pro Ala Ala Thr Val Glu Ile Gln Lys Ile Ile His Lys Asn
            100                 105                 110

Ile Ile Thr Lys Val Thr Lys His Gly Met Asn Asp Arg Gly Met Lys
        115                 120                 125

Lys Ala Asn Phe Ala Val Leu Arg Glu Thr Ala Met Asp Ala Ile Leu
130                 135                 140

Leu Glu Ala Gly Phe Cys Asp Ser Thr Asp Ala Leu Ile Leu Glu Lys
145                 150                 155                 160

Lys Ala Tyr Gln Thr Asp Tyr Cys Leu Gly Ile Val Ser Ala Val Gln
                165                 170                 175

Glu Ile Phe Gly Ala Met Val Thr Lys Tyr Arg Ala Gly Lys Tyr Leu
            180                 185                 190

Thr Ser Asp Asp Ala Ile Ser Gly Thr Asn Ile Lys Gly Tyr Leu Glu
        195                 200                 205
```

```
Ala Gly Thr Lys Val Phe Val Tyr Lys Glu Thr Glu Lys Thr Leu Asn
    210                 215                 220

Leu Thr Thr Thr Lys Gly Val Pro Gly Ser Trp Val Leu Lys Thr Glu
225                 230                 235                 240

Val Asn Thr Gly Lys Arg
                245

<210> SEQ ID NO 20
<211> LENGTH: 2253
<212> TYPE: DNA
<213> ORGANISM: Listeria monocytogenes strain 1/2a 1144 (DuPont)

<400> SEQUENCE: 20
atgacaaatc aaatctttaa atcagctatt cttgattttt ctgttagtgc acagaacgct      60
aaagctaatg ttcctcagat aaaatttagt acgcaagact ctggagggac tgcgcgatta     120
aagtttactg caaaaaaaga tgataacaat ttaccacttt caagcgcggc agaggtaacg     180
cttgctatgg tattgtctgt tggcaaaaaa tacgaaagta gctacattgt taatccagaa     240
ataattaaca gaacagaagg tgttttttgaa tactcattga ctgatgagca ataagtcac     300 gacggacaag ctaatgcaga attgtacgtt aaatatccaa atcaaacaat gcaaatcaat     360
cgttttagtt ttgttattga aaaagcgatg attgatgata atttttttgcc cgttgctacc     420 tattatgttg aaaaatggga tgattacgaa aaaatattta cgaaaaagt ggaaattctt     480 caaaatgaaa ttgatgattt gcaaggacaa gctactgaat taaaaaacac attcgatagt     540
cttaatccag accaatttcc ccaaaaagca gattttgaaa tcatataaa caacacaaac     600 attcatgtga cgatgactga taaaacaaat tggaatacaa agaaaatac tgcgggatca     660 caagcaaaag cggatagtgc attaaactct gctaaagcat atacagatag caagatggat     720
agttacggag cttggataaa tgtacccctc gcctctggtt actcaactgg cgacagtaat     780
acacctcaat atcgactggt agcaaaacaa acttctaccg gtttgaaaac ttttgctgaa     840
ttccgcggat cagttgctgg tacatttatt agtacagcaa atagtactct tgcaacaatg     900
cccgctggca aagaccaat tgtcacttat tacggtgctg ccacttcaaa taacgggaac     960
ggtggtcgta ttgctattcc agttgacgga aagctattac aagtgtcatc tacagataat    1020
gctaatcctt cgtacgtaag cctttcaacg atattatacg aagttggcaa ttaggaggag    1080
taaacatgaa ctataaacag ttttacgcat atgatgaaaa tggcaattat ctcgaaacaa    1140
tacttgtgtt tgaagatgaa aaggtttaa tcaatcaacc gaaaaattct acaaatattg    1200
aaccttccat aatcgaaaac ggcatagcaa gagcaatgta ttatccgcgt tggaatgggg    1260
aagattggga cgaagacaag aaaagatggg aattagaaaa tccaatcata cccgcagaaa    1320
aaacggaaat agaaaaatta agagaggaat tactactcac ccaagaagcg ttagcggcat    1380
tgttcgaaag taatttaggg tgatgaaatg gcttatatga taccaatta cgtgaattta    1440 gtgatgaata atcgaaaaac tattgaagaa gttcctgcga atttgcgagg tcaggtaaaa    1500
gcaaaagtgg atgagctaaa acaagaacaa caacgaatac agtcagaaga aatagaagcc    1560
gaataggctt atttttatg ggggatgatg aaaatgtatg atggactaac aaaagttttt    1620
gattatgctt tagcgaaaga aatgttcttc gcggcgctct ttgtagcgct ttttataatc    1680
ttactaatta tcacaaaaag aatttgggat gattcgaaaa ttgtaagaat agaaatgaaa    1740
gaagaacgcg aaaagtgga ggaagaacga gaagcgta ataaggaatc gaagaagag      1800 agagataaat ttataagtac gatgaacgaa caacagcgat tgatggatag gcaaaatgac    1860
```

-continued

```
atgatgaaac agcaacaaca atcaattgac agcttgtcta atcagtcgg  aaagttagct    1920 cacaaagtag atttgttgga acacaaaata cgaagtgaa  ggatgataga aatggagttt    1980
ggaaaagagt tactagttta catgacattt ttagtagttg taacacctgt gtttgttcag    2040
gcgattaaga agacggagtt agtcccgtct aagtggcttc cgactgttag catacttatt    2100
ggtgctattc tgggcgcatt agcaacgttt ttggacggct ctggatcgct tgcaacgatg    2160
atttgggcag gcgctttagc aggagctggt ggtactggat tatttgaaca atttactaat    2220
cgaagcaaaa aatatgggaga ggatgataaa taa                                2253
```

<210> SEQ ID NO 21
<211> LENGTH: 357
<212> TYPE: PRT
<213> ORGANISM: Listeria monocytogenes strain 1/2a 1144 (DuPont)

<400> SEQUENCE: 21

```
Met Thr Asn Gln Ile Phe Lys Ser Ala Ile Leu Asp Phe Ser Val Ser
  1               5                  10                  15

Ala Gln Asn Ala Lys Ala Asn Val Pro Gln Ile Lys Phe Ser Thr Gln
             20                  25                  30

Asp Ser Gly Gly Thr Ala Arg Leu Lys Phe Thr Ala Lys Lys Asp Asp
         35                  40                  45

Asn Asn Leu Pro Leu Ser Ser Ala Ala Glu Val Thr Leu Ala Met Val
     50                  55                  60

Leu Ser Val Gly Lys Lys Tyr Glu Ser Ser Tyr Ile Val Asn Pro Glu
 65                  70                  75                  80

Ile Ile Asn Arg Thr Glu Gly Val Phe Glu Tyr Ser Leu Thr Asp Glu
                 85                  90                  95

Gln Ile Ser His Asp Gly Gln Ala Asn Ala Glu Leu Tyr Val Lys Tyr
            100                 105                 110

Pro Asn Gln Thr Met Gln Ile Asn Arg Phe Ser Phe Val Ile Glu Lys
        115                 120                 125

Ala Met Ile Asp Asp Asn Phe Leu Pro Val Ala Thr Tyr Tyr Val Glu
    130                 135                 140

Lys Trp Asp Asp Tyr Glu Lys Ile Phe Asn Glu Lys Val Glu Ile Leu
145                 150                 155                 160

Gln Asn Glu Ile Asp Asp Leu Gln Gly Gln Ala Thr Glu Leu Lys Asn
                165                 170                 175

Thr Phe Asp Ser Leu Asn Pro Asp Gln Phe Pro Gln Lys Ala Asp Phe
            180                 185                 190

Glu Asn His Ile Asn Asn Thr Asn Ile His Val Thr Met Thr Asp Lys
        195                 200                 205

Thr Asn Trp Asn Thr Lys Glu Asn Thr Ala Gly Ser Gln Ala Lys Ala
    210                 215                 220

Asp Ser Ala Leu Asn Ser Ala Lys Ala Tyr Thr Asp Ser Lys Met Asp
225                 230                 235                 240

Ser Tyr Gly Ala Trp Ile Asn Val Pro Leu Ala Ser Gly Tyr Ser Thr
                245                 250                 255

Gly Asp Ser Asn Thr Pro Gln Tyr Arg Leu Val Ala Lys Gln Thr Ser
            260                 265                 270

Thr Gly Leu Lys Thr Phe Ala Glu Phe Arg Gly Ser Val Ala Gly Thr
        275                 280                 285

Phe Ile Ser Thr Ala Asn Ser Thr Leu Ala Thr Met Pro Ala Gly Thr
    290                 295                 300
```

```
Arg Pro Ile Val Thr Tyr Tyr Gly Ala Ala Thr Ser Asn Asn Gly Asn
305                 310                 315                 320

Gly Gly Arg Ile Ala Ile Pro Val Asp Gly Lys Leu Leu Gln Val Ser
            325                 330                 335

Ser Thr Asp Asn Ala Asn Pro Ser Tyr Val Ser Leu Ser Thr Ile Leu
            340                 345                 350

Tyr Glu Val Gly Asn
            355

<210> SEQ ID NO 22
<211> LENGTH: 105
<212> TYPE: PRT
<213> ORGANISM: Listeria monocytogenes strain 1/2a 1144 (DuPont)

<400> SEQUENCE: 22

Met Asn Tyr Lys Gln Phe Tyr Ala Tyr Asp Glu Asn Gly Asn Tyr Leu
1               5                   10                  15

Glu Thr Ile Leu Val Phe Glu Asp Glu Lys Gly Leu Ile Asn Gln Pro
            20                  25                  30

Lys Asn Ser Thr Asn Ile Glu Pro Ser Ile Ile Glu Asn Gly Ile Ala
        35                  40                  45

Arg Ala Met Tyr Tyr Pro Arg Trp Asn Gly Glu Asp Trp Asp Glu Asp
    50                  55                  60

Lys Lys Arg Trp Glu Leu Glu Asn Pro Ile Ile Pro Ala Glu Lys Thr
65                  70                  75                  80

Glu Ile Glu Lys Leu Arg Glu Glu Leu Leu Thr Gln Glu Ala Leu
                85                  90                  95

Ala Ala Leu Phe Glu Ser Asn Leu Gly
            100                 105

<210> SEQ ID NO 23
<211> LENGTH: 52
<212> TYPE: PRT
<213> ORGANISM: Listeria monocytogenes strain 1/2a 1144 (DuPont)

<400> SEQUENCE: 23

Met Ala Tyr Met Ile Pro Ile Tyr Val Asn Leu Val Met Asn Asn Arg
1               5                   10                  15

Lys Thr Ile Glu Glu Val Pro Ala Asn Leu Arg Gly Gln Val Lys Ala
            20                  25                  30

Lys Val Asp Glu Leu Lys Gln Glu Gln Gln Arg Ile Gln Ser Glu Glu
        35                  40                  45

Ile Glu Ala Glu
    50

<210> SEQ ID NO 24
<211> LENGTH: 121
<212> TYPE: PRT
<213> ORGANISM: Listeria monocytogenes strain 1/2a 1144 (DuPont)

<400> SEQUENCE: 24

Met Tyr Asp Gly Leu Thr Lys Val Phe Asp Tyr Ala Leu Ala Lys Glu
1               5                   10                  15

Met Phe Phe Ala Ala Leu Phe Val Ala Leu Phe Ile Ile Leu Leu Ile
            20                  25                  30

Ile Thr Lys Arg Ile Trp Asp Asp Ser Lys Ile Val Arg Ile Glu Met
        35                  40                  45

Lys Glu Glu Arg Glu Lys Val Glu Glu Glu Arg Glu Lys Arg Asn Lys
```

```
                50                  55                  60
Glu Ser Lys Glu Glu Arg Asp Lys Phe Ile Ser Thr Met Asn Glu Gln
 65                  70                  75                  80

Gln Arg Leu Met Asp Arg Gln Asn Asp Met Met Lys Gln Gln Gln Gln
                 85                  90                  95

Ser Ile Asp Ser Leu Ser Lys Ser Val Gly Lys Leu Ala His Lys Val
            100                 105                 110

Asp Leu Leu Glu His Lys Ile Thr Lys
        115                 120

<210> SEQ ID NO 25
<211> LENGTH: 93
<212> TYPE: PRT
<213> ORGANISM: Listeria monocytogenes strain 1/2a 1144 (DuPont)

<400> SEQUENCE: 25

Met Glu Phe Gly Lys Glu Leu Leu Val Tyr Met Thr Phe Leu Val Val
 1               5                  10                  15

Val Thr Pro Val Phe Val Gln Ala Ile Lys Lys Thr Glu Leu Val Pro
             20                  25                  30

Ser Lys Trp Leu Pro Thr Val Ser Ile Leu Ile Gly Ala Ile Leu Gly
         35                  40                  45

Ala Leu Ala Thr Phe Leu Asp Gly Ser Gly Ser Leu Ala Thr Met Ile
     50                  55                  60

Trp Ala Gly Ala Leu Ala Gly Ala Gly Gly Thr Gly Leu Phe Glu Gln
 65                  70                  75                  80

Phe Thr Asn Arg Ser Lys Lys Tyr Gly Glu Asp Asp Lys
                 85                  90

<210> SEQ ID NO 26
<211> LENGTH: 178
<212> TYPE: PRT
<213> ORGANISM: Listeria monocytogenes strain 1/2a F6854

<400> SEQUENCE: 26

Met Thr Lys Ile Val Lys Met Ser Glu Lys Asn Glu His Gly Thr Leu
 1               5                  10                  15

Glu Gln Phe Tyr Pro Glu Thr His Ala Glu Ala Val Lys Gly Leu Val
             20                  25                  30

Ser Val Thr Glu Glu Lys Thr Thr Trp Gly Gly Lys Glu Thr Thr
         35                  40                  45

Ala Gly Ala Glu Gln Lys Ala Asn Ala Ala Leu Asn Ser Ala Lys Asp
     50                  55                  60

Tyr Val Asp Thr Ile Gly Ser Gly Ile Val Ile Phe Lys Gly Ala Asn
 65                  70                  75                  80

Leu Met Gly Ala Gly Gln Ala Phe Lys Trp Asp Pro Asp Lys Leu Lys
                 85                  90                  95

Phe Gly Met Thr Leu Leu Phe Ser Arg Tyr Asp Ala Thr Thr Asn Thr
            100                 105                 110

Pro Gln Asp Tyr Tyr His Ser Val Phe Leu Ser Arg Ala Gln Leu
        115                 120                 125

Leu Glu Ile Ala Gly Gly Val Leu Ile Gln Met Pro Ser Leu Thr
        130                 135                 140

Tyr Gly Asp Lys Lys Tyr Phe Tyr Val Ser Thr Thr Gly Ile Ser Gly
145                 150                 155                 160

His Ala Asp Asn Ser Asn Tyr Lys Ala Trp Ala Leu Arg Gln Val Thr
```

Ile Met

<210> SEQ ID NO 27
<211> LENGTH: 178
<212> TYPE: PRT
<213> ORGANISM: Listeria innocua strain 6a 33090

<400> SEQUENCE: 27

```
Met Thr Lys Ile Val Lys Met Ser Glu Lys Asn Glu His Gly Thr Leu
1               5                   10                  15
Glu Gln Phe Tyr Pro Glu Thr His Ala Glu Ala Val Lys Gly Leu Val
            20                  25                  30
Ser Val Thr Glu Glu Lys Thr Thr Trp Asn Glu Lys Glu Thr Thr
        35                  40                  45
Ala Gly Ala Glu Gln Lys Ala Asn Thr Ala Leu Asn Ser Ala Lys Glu
    50                  55                  60
Tyr Val Asp Thr Ile Gly Lys Gly Thr Val Ile Phe Lys Gly Ala Asn
65                  70                  75                  80
Ile Met Gly Ala Gly Gln Lys Tyr Thr Trp Ser Ser Ser Lys Leu Lys
                85                  90                  95
Phe Gly Ile Thr Leu Leu Phe Ser Arg Tyr Asp Ser Ala Asn Asn Thr
            100                 105                 110
Pro Leu Asp Tyr Tyr Tyr His Ser Val Phe Leu Ser Lys Ala Gln Leu
        115                 120                 125
Ala Glu Leu Ala Gly Lys Gly Leu Leu Val Pro Met Pro Ser Ala Ile
    130                 135                 140
Tyr Gly Glu Arg Lys Tyr Leu Tyr Val Ser Glu Thr Glu Val Ala Gly
145                 150                 155                 160
His Asn Asp Asn Thr Asn Asn Ala Ser Trp Ala Leu Arg Gln Leu Thr
                165                 170                 175
Val Met
```

<210> SEQ ID NO 28
<211> LENGTH: 1747
<212> TYPE: DNA
<213> ORGANISM: Artificial Sequence
<220> FEATURE:
<223> OTHER INFORMATION: Synthetic polynucleotide, hyperspank_MCS_lacI
      cassette

<400> SEQUENCE: 28

```
gaattcgact ctctagcttg aggcatcaaa taaaacgaaa ggctcagtcg aaagactggg     60
cctttcgttt tatctgttgt ttgtcggtga acgctctcct gagtaggaca atccgccgc    120
tctagctaag cagaaggcca tcctgacgga tggcctttt gcgtttctac aaactcttg     180
taactctaga gctgcctgcc gcgtttcggt gatgaagatc ttcccgatga ttaattaatt    240
cagaacgctc ggttgccgcc gggcgttttt tatgcagcaa tggcaagaac gttgctcgag    300
ggtaaatgtg agcactcaca attcattttg caaaagttgt tgactttatc tacaaggtgt    360
ggcataatgt gtgtaattgt gagcggataa caattaagct tagtcgacag ctagccgcat    420
gcaagctaat tcggtggaaa cgaggtcatc atttccttcc gaaaaaacgg ttgcatttaa    480
atcttacata tgtaatactt tcaaagacta catttgtaag atttgatgtt tgagtcggct    540
gaaagatcgt acgtaccaat tattgtttcg tgattgttca agccataaca ctgtagggat    600
agtggaaaga gtgcttcatc tggttacgat caatcaaata ttcaaacgga gggagacgat    660
```

```
tttgatgaaa ccagtaacgt tatacgatgt cgcagagtat gccggtgtct cttatcagac    720
cgtttcccgc gtggtgaacc aggccagcca cgtttctgcg aaaacgcggg aaaaagtgga    780
agcggcgatg gcggagctga attacattcc caaccgcgtg gcacaacaac tggcgggcaa    840
acagtcgttg ctgattggcg ttgccacctc cagtctggcc ctgcacgcgc cgtcgcaaat    900
tgtcgcggcg attaaatctc gcgccgatca actgggtgcc agcgtggtgg tgtcgatggt    960
agaacgaagc ggcgtcgaag cctgtaaagc ggcggtgcac aatcttctcg cgcaacgcgt   1020
cagtgggctg atcattaact atccgctgga tgaccaggat gccattgctg tggaagctgc   1080
ctgcactaat gttccggcgt tatttcttga tgtctctgac cagacaccca tcaacagtat   1140
tattttctcc catgaagacg gtacgcgact gggcgtggag catctggtcg cattgggtca   1200
ccagcaaatc gcgctgttag cgggcccatt aagttctgtc tcggcgcgtc tgcgtctggc   1260
tggctggcat aaatatctca ctcgcaatca aattcagccg atagcggaac gggaaggcga   1320
ctggagtgcc atgtccggtt ttcaacaaac catgcaaatg ctgaatgagg gcatcgttcc   1380
cactgcgatg ctggttgcca acgatcagat ggcgctgggc gcaatgcgcg ccattaccga   1440
gtccgggctg cgcgttggtg cggatatctc ggtagtggga tacgacgata ccgaagacag   1500
ctcatgttat atcccgccgt taaccaccat caaacaggat tttcgcctgc tggggcaaac   1560
cagcgtggac cgcttgctgc aactctctca gggccaggcg gtgaagggca atcagctgtt   1620
gcccgtctca ctggtgaaaa gaaaaaccac cctggcgccc aatacgcaaa ccgcctctcc   1680
ccgcgcgttg gccgattcat taatgcagct ggcacgacag gtttcccgac tggaaagcgg   1740
gcagtga                                                            1747

<210> SEQ ID NO 29
<211> LENGTH: 188
<212> TYPE: PRT
<213> ORGANISM: Listeria monocytogenes strain 1/2a 35152

<400> SEQUENCE: 29

Met Thr Lys Ile Val Lys Met Ser Glu Lys Asn Glu His Gly Thr Leu
1               5                   10                  15

Glu Gln Phe Tyr Pro Glu Thr His Ala Glu Ala Val Lys Gly Leu Val
            20                  25                  30

Ser Val Ser Glu Glu Lys Thr Asn Trp Asn Thr Lys Glu Asn Thr
        35                  40                  45

Ala Gly Ser Gln Ala Lys Ala Asp Ser Ala Leu Asn Ser Ala Lys Ala
    50                  55                  60

Tyr Thr Asp Ser Lys Met Asp Ser Tyr Gly Ala Trp Ile Asn Val Pro
65                  70                  75                  80

Leu Ala Ser Gly Tyr Ser Thr Gly Asp Ser Asn Thr Pro Gln Tyr Arg
                85                  90                  95

Leu Val Ala Lys Gln Thr Ser Thr Gly Leu Lys Thr Phe Ala Glu Phe
            100                 105                 110

Arg Gly Ser Val Ala Gly Thr Phe Ile Ser Thr Ala Asn Ser Thr Leu
        115                 120                 125

Ala Thr Met Pro Ala Gly Thr Arg Pro Ile Val Thr Tyr Tyr Gly Ala
    130                 135                 140

Ala Thr Ser Asn Asn Gly Asn Gly Gly Arg Ile Ala Ile Pro Val Asp
145                 150                 155                 160

Gly Lys Leu Leu Gln Val Ser Ser Thr Asp Asn Ala Asn Pro Ser Tyr
                165                 170                 175
```

```
Val Ser Leu Ser Thr Ile Leu Tyr Glu Val Gly Asn
            180                 185

<210> SEQ ID NO 30
<211> LENGTH: 169
<212> TYPE: PRT
<213> ORGANISM: Bacteriophage TP901-1

<400> SEQUENCE: 30

Met Ala Glu Leu Thr Ala Lys Gln Gly Lys Asp Ile Ile Leu Leu Tyr
1               5                   10                  15

Arg Val Leu Ser Lys Ala Ser Thr Glu Ala Ala Trp Lys Leu Ala Phe
            20                  25                  30

Gln Thr Glu His Ser Asn Glu Lys Thr Arg Asp Tyr Asn Thr Thr Ala
        35                  40                  45

Thr Lys Asp Gly Pro Val Gly Ala Leu Ala Glu Val Glu Tyr Ser Leu
    50                  55                  60

Ser Ala Thr Ser Ile Ala Ala Asn Gly Asp Pro His Leu Asp Glu Met
65                  70                  75                  80

Asp Lys Ala Phe Asp Asp Ala Ala Ile Ile Glu Val Trp Glu Ile Asp
                85                  90                  95

Lys Ala Glu Lys Ala Thr Leu Gly Leu Asp Ser Gly Lys Tyr Lys Ala
            100                 105                 110

Lys Tyr Leu Arg Ala Tyr Leu Thr Ser Phe Ser Tyr Glu Pro Asn Ser
        115                 120                 125

Glu Asp Ala Leu Glu Leu Ser Leu Glu Phe Gly Val Phe Gly Lys Pro
    130                 135                 140

Gln Lys Gly Tyr Ala Thr Leu Thr Thr Glu Gln Ala Asn Val Val Gln
145                 150                 155                 160

Tyr Val Phe Lys Asp Thr Val Arg Gly
                165

<210> SEQ ID NO 31
<211> LENGTH: 245
<212> TYPE: PRT
<213> ORGANISM: Artificial Sequence
<220> FEATURE:
<223> OTHER INFORMATION: Synthetic sequence, TP901-1 like phage from
      Enterococcus avium ATCC 14025

<400> SEQUENCE: 31

Met Pro Glu Val Thr Gly Phe Glu Asn Gln Leu Tyr Cys Asp Phe Ser
1               5                   10                  15

Gln Ser Ala Thr Lys Ala Val Ala Gly Lys Asn Ile Leu Leu Ala Ile
            20                  25                  30

Phe Asn Met Thr Gly Asp Lys Leu Leu Ala Ile Ala Gly Gln Gln Gly
        35                  40                  45

Leu Thr Ile Asn Arg Ser Lys Asp Ser Ile Glu Ile Thr Ser Lys Asp
    50                  55                  60

Thr Lys Gly Gly Trp Lys Ser Lys Ile Gly Gly Met Lys Glu Trp Ser
65                  70                  75                  80

Ile Asp Asn Asp Gly Leu Tyr Val Arg Asp Asp Glu Ser His Lys Val
                85                  90                  95

Leu Gly Gln Tyr Phe Asp Gly Asp Pro Val Cys Ile Lys Val Leu
            100                 105                 110

Asp Met Gln Ser Lys Thr Gly Met Phe Gly Gly Leu Ala Ile Val Thr
        115                 120                 125
```

Asp Tyr Ser Leu Glu Ala Pro Tyr Asp Ala Met Thr Tyr Ser Ile
        130                 135                 140

Lys Leu Asp Gly Met Gly Ala Leu Val Asp Leu Ser Asp Ser Glu Ala
145                 150                 155                 160

Asn Gln Met Pro Glu Gly Thr Ala Ser Ile Lys Leu Asn Lys Thr Thr
                165                 170                 175

Ala Ser Ile Val Val Asp Ala Asn Glu Ser Leu Ile Ala Thr Val Gln
            180                 185                 190

Pro Ser Thr Asp Thr Val Ser Trp Lys Thr Ser Asp Val Thr Val Ala
        195                 200                 205

Thr Val Asp Asn Thr Gly Arg Val Thr Gly Lys Val Gly Asn Ala
    210                 215                 220

Ile Ile Thr Ala Thr Ser Thr Lys Glu Val Ala Thr Cys Leu Val
225                 230                 235                 240

Thr Ile Thr Ala Ser
                245

<210> SEQ ID NO 32
<211> LENGTH: 144
<212> TYPE: PRT
<213> ORGANISM: Listeriophage A118

<400> SEQUENCE: 32

Met Arg Ile Lys Asn Ala Lys Thr Lys Tyr Ser Val Ala Glu Ile Val
1               5                   10                  15

Ala Gly Ala Gly Glu Pro Asp Trp Lys Arg Leu Ser Lys Trp Ile Thr
            20                  25                  30

Asn Val Ser Asp Asp Gly Ser Asp Asn Thr Glu Glu Gln Gly Asp Tyr
        35                  40                  45

Asp Gly Asp Gly Asn Glu Lys Thr Val Val Leu Gly Tyr Ser Glu Ala
    50                  55                  60

Tyr Thr Phe Glu Gly Thr His Asp Arg Glu Asp Glu Ala Gln Asn Leu
65                  70                  75                  80

Ile Val Ala Lys Arg Arg Thr Pro Glu Asn Arg Ser Ile Met Phe Lys
                85                  90                  95

Ile Glu Ile Pro Asp Thr Glu Thr Ala Ile Gly Lys Ala Thr Val Ser
            100                 105                 110

Glu Ile Lys Gly Ser Ala Gly Gly Gly Asp Ala Thr Glu Phe Pro Ala
        115                 120                 125

Phe Gly Cys Arg Ile Ala Tyr Asp Glu Thr Pro Thr Val Thr Lys Pro
    130                 135                 140

<210> SEQ ID NO 33
<211> LENGTH: 1794
<212> TYPE: PRT
<213> ORGANISM: Listeriophage A118

<400> SEQUENCE: 33

Met Ser Asp Gly Ser Val Val Ile Glu Ile Ser Leu Asp Asp Lys Lys
1               5                   10                  15

Ala Asp Lys Gln Leu Asp Ala Phe Glu Lys Asp Leu Ala Lys Ala Gly
            20                  25                  30

Thr Asn Ala Gly Ala Ala Leu Asp Lys Ala Tyr Arg Glu Ala Val Ser
        35                  40                  45

Asp Ile Ala Ser Gln Ser Lys Arg Leu Lys Asp Thr Phe Val Asn Ala
    50                  55                  60

```
Phe Lys Ser Met Gly Asn Ala Gly Ser Asn Ala Leu Lys Ala Ser Leu
 65                  70                  75                  80

Asn Phe Ile Arg Glu Leu Pro Ser Asn Val Gln Ala Ala Leu Ser Lys
                 85                  90                  95

Leu Ala Ser Thr Val Lys Thr Gly Phe Val Asn Ala Ala Lys Ala Ser
            100                 105                 110

Ile Thr Ala Val Lys Asn Leu Gly Thr Ser Ile Lys Asn Thr Ala Val
        115                 120                 125

Asn Ile Lys Asn Gly Phe Phe Ser Ile Ala Lys Thr Val Gln Ser Ser
130                 135                 140

Ile Met Ser Ala Val Lys Ile Ser Ile Asn Val Ile Lys Ser Ile Pro
145                 150                 155                 160

Ser Ala Ile Lys Ser Ala Gly Ser Ser Ile Lys Ser Ala Leu Val Ser
                165                 170                 175

Ser Leu Gln Ala Ala Lys Met Ala Ala Ile Ser Phe Ala Gln Thr Thr
            180                 185                 190

Val Lys Val Ile Lys Ser Ile Pro Gly Ala Ala Lys Thr Ala Ala Thr
        195                 200                 205

Ala Val Lys Asn Ser Phe Val Ala Tyr Lys Ala Val Val Val Ala
210                 215                 220

Ala Tyr Met Ser Val Lys Gly Thr Ile Ser Ala Val Lys Ala Ile Pro
225                 230                 235                 240

Ser Ala Thr Lys Ser Ala Ala Leu Ala Val Ser Ser Ala Met Lys Thr
                245                 250                 255

Ala Phe Ser Ala Val Val Ser Ala Ala Lys Thr Thr Gly Thr Thr Val
            260                 265                 270

Lys Thr Ala Leu Thr Asn Gly Phe Ser Ala Ile Lys Ser Gly Ala Lys
        275                 280                 285

Thr Ala Gly Gln Val Gly Ile Ser Ala Leu Lys Gly Leu Gly Asn Ala
290                 295                 300

Ala Lys Ser Thr Gly Ser Leu Ile Lys Asn Gly Leu Val Ser Gly Phe
305                 310                 315                 320

Asn Ala Ala Arg Ser Ala Ala Lys Gly Ala Gly Ala Gly Met Arg Glu
                325                 330                 335

Ala Leu Lys Asn Ser Val Glu Lys Pro Ala Glu Gln Ala Arg Phe Ser
            340                 345                 350

Ile Leu Arg Leu Ala Ala Ala Phe Gly Leu Ile Ala Ala Thr Lys Asn
        355                 360                 365

Val Val Gly Ser Ala Ile Gly Arg Val Asp Thr Ile Asp Thr Ala Thr
370                 375                 380

Lys Ser Leu Thr Val Leu Thr Gly Ser Ala Lys Asp Ala Gln Leu Val
385                 390                 395                 400

Met Thr Asp Leu Thr Ala Ala Ile Asp Gly Thr Pro Ile Ala Leu Asp
                405                 410                 415

Ala Val Ala Leu Gly Ala Lys Lys Met Val Ala Gly Met Gln Ala
            420                 425                 430

Ala Asn Val Lys Pro Val Phe Thr Ala Ile Ala Asp Ala Ala Tyr Gly
        435                 440                 445

Val Gly Asn Gly Ser Glu Ser Ile Asp Gln Met Thr Asp Ala Ile Ser
450                 455                 460

Ala Leu Gln Ala Ser Gly Val Ala Tyr Ser Asp Asp Ile Asn Arg Leu
465                 470                 475                 480
```

```
Val Asp Ala Gly Val Pro Ala Trp Gln Ile Leu Ala Asn Ser Thr Gly
                485                 490                 495

Lys Ser Val Gly Glu Met Lys Lys Tyr Val Ser Glu Gly Ser Leu Glu
            500                 505                 510

Ser Thr Lys Ala Ile Ala Met Leu Thr Lys Gly Ile Glu Glu Gly Thr
        515                 520                 525

Thr Gly Met Ala Gly Asn Thr Ala Lys Met Ala Gly Leu Ala Lys Thr
    530                 535                 540

Ala Gly Asn Thr Ile Ser Gly Ser Phe Ala Asn Met Lys Thr Ala Ala
545                 550                 555                 560

Val Lys Ser Leu Ala Asn Ile Ala Glu Asn Leu Lys Gly Pro Ile Ile
                565                 570                 575

Gln Ala Leu Asp Val Ala Lys Asn Ala Phe Lys Gln Phe Ala Ala Val
            580                 585                 590

Thr Ala Ser Pro Glu Phe Gln Lys Lys Leu Ser Asp Met Ile Gln Lys
        595                 600                 605

Ile Lys Glu Leu Ile Pro Val Met Val Lys Leu Ala Pro Thr Ile Leu
    610                 615                 620

Lys Val Val Ser Ala Met Leu Ala Leu Gln Ala Val Ser Ser Val Tyr
625                 630                 635                 640

Val Ala Phe Ser Asn Ile Gly Lys Met Phe Val Pro Leu Lys Asn Gly
                645                 650                 655

Leu Phe Val Ile Ala Thr Gly Phe Met Lys Leu Ala Lys Thr Ile Arg
            660                 665                 670

His Pro Ile Thr Ala Ile Lys Asn Leu Ala Phe Ala Ile Lys Tyr Phe
        675                 680                 685

Ile Val Thr Ser Gly Ala Val Ile Ala Ile Val Gly Ala Val Ile Ala
    690                 695                 700

Val Leu Tyr Gly Met Tyr Ala Ala Phe Lys Glu Asn Thr Ala Asn Ile
705                 710                 715                 720

Lys Gly Phe Leu Ser Gly Met Phe Asp Ala Val Lys Asn Ser Phe Gly
                725                 730                 735

Lys Ile Val Asp Val Phe Lys Gln Ile Val Ser Ala Leu Lys Pro Val
            740                 745                 750

Gly Ser Gly Phe Lys Asp Ile Leu Lys Tyr Ile Gly Val Gly Val Trp
        755                 760                 765

Val Ala Phe Gly Ile Val Leu Ala Thr Val Val Asp Ile Ile Gln Val
    770                 775                 780

Leu Ala Arg Ile Val Leu Val Ala Ile Lys Gly Leu Gln Gly Leu Tyr
785                 790                 795                 800

Tyr Ala Ile Lys Ala Ala Phe Gln Ala Leu Ser Gly Asp Leu Lys Gly
                805                 810                 815

Ala Lys Lys Ser Leu Glu Gln Ser Lys Asp Ala Phe Val Asp Ala Gly
            820                 825                 830

Ser Ala Ile Lys Asp Ala Phe Asn Lys Asp Asn Tyr Ala Leu Thr Gly
        835                 840                 845

Thr Ile Glu Ser Leu Lys Glu Met Gly Gly Glu Ala Glu Lys Thr Gly
    850                 855                 860

Thr Lys Ala Glu Thr Ser Asn Lys Lys Ile Ser Ser Leu Lys Leu
865                 870                 875                 880

Val Glu Ser Thr Ala Lys Gln Thr Glu Ala Thr Val Thr Lys Ser Asn
                885                 890                 895

Gln Ala Ile Asp Thr Met Leu Ser Gly Gly Val Asp Gln Tyr Gly Asn
```

```
                900             905              910
Lys Leu Ser Glu Lys Thr Lys Ser Phe Leu Asn Ala Ala Lys Glu Leu
            915             920             925

Tyr Gly Gln Tyr Gln Glu Ser Ala Lys Lys Ser Gln Asp Lys Tyr Ser
            930             935             940

Val Ala Met Glu Lys Ala Gln Ser Leu Glu Gly Asp Lys Arg Lys Lys
945             950             955             960

Ala Ile Ala Asp Ala Asn Ala Thr Leu Val Ala Glu Ile Asp Lys Asn
            965             970             975

Asn Gly Thr Leu Leu Thr Leu Gln Ala Asp Tyr Ala Lys Leu Leu Lys
            980             985             990

Asp Asn Lys Trp Val Asp Gly Thr  Glu Leu Thr Ala Gln  Gln Lys Lys
            995             1000            1005

Phe Leu Gln Gln Gln Thr Ala  Asp Ile Gln Ala Glu  Leu Ala Lys
            1010            1015            1020

Gln Asn Gln Leu Tyr Val Glu  Gly Asn Leu Leu Lys  Leu Ala Asn
            1025            1030            1035

Gly Lys Thr Leu Asn Glu Lys  Glu Arg Ala Thr Ser  Ile Glu Val
            1040            1045            1050

Gln Lys Ser Leu Tyr Gly Asp  Arg Lys Lys Ala Val  Glu Ile Gly
            1055            1060            1065

Glu Lys Glu Leu Ala Asp Leu  Lys Arg Lys Lys Ser  Asp Ala Thr
            1070            1075            1080

Thr Glu Thr Glu Lys Ala Asn  Tyr Gln Ile Gln Ile  Asp Glu Gln
            1085            1090            1095

Thr Lys Lys Asn Lys Thr Leu  Ala Gly Asn Leu Gln  Lys Trp Ala
            1100            1105            1110

Ser Glu Met Asn Ala Ile Ile  Ala Asn Gly Gly Thr  Leu Asn Ala
            1115            1120            1125

Glu Thr  Phe Ala Lys Gly Leu  Ser Glu Met Gly Asn  Ile Ser Asp
            1130            1135            1140

Glu Gln Leu Gly Ala Val Trp  Gln Asp Phe Val Lys  Val Ser Gly
            1145            1150            1155

Ser Ile Asp Asn Thr Leu Ala  Gly Leu Ala Ala Val  Met Ser Gln
            1160            1165            1170

Arg Gly Gly Glu Gly Val Gln  Ala Phe Val Thr Ala  Leu Gln Ser
            1175            1180            1185

Gly Asp Tyr Thr Thr Ala Ala  Leu Lys Ile Asn Asp  Asp Val Leu
            1190            1195            1200

Asn Thr  Ile Ser Gly Leu Pro  Asn Ser Met Phe Leu  Asn Gly Gln
            1205            1210            1215

Ser Gly Lys Asp Gln Phe Leu  Leu Ala Ile Lys Ser  Gly Asp Phe
            1220            1225            1230

Gln Gly Ala Gly Lys Phe Leu  Leu Asp Gly Val Lys  Met Gly Ala
            1235            1240            1245

Asp Pro Leu Pro Gly Glu Met  Glu Lys Asn Gly Lys  Lys Ser Gly
            1250            1255            1260

Asp Ala Gln Ala Lys Gly Val  Lys Ser Thr Ala Glu  Ala Asn Lys
            1265            1270            1275

Ser Ala Gly Lys Glu Ile Lys  Asn Asn Ala Lys Ser  Gly Ala Phe
            1280            1285            1290

Asp Pro Asn Leu Phe Lys Met  Thr Gly Ser Lys Asn  Ser Ser Gly
            1295            1300            1305
```

```
Phe Asn Asn Gly Ile Leu Gly Gly Lys Asp Ala Phe Ser Ala
    1310            1315            1320

Gly Thr Ser Val Gly Gly Ser Ala Lys Ser Gly Ala Ala Ser Val
    1325            1330            1335

Asp Ser Ser Gly Val Gly Ser Asp Phe Ala Ala Gly Phe Ala Asn
    1340            1345            1350

Gly Ile Arg Ser Gly Ala Gly Ala Val Gly Glu Ala Ala Ala Ser
    1355            1360            1365

Ile Ala Ala Lys Ala Leu Ala Ala Val Gln Lys Lys Gln Asp Ser
    1370            1375            1380

His Ser Pro Ser Lys Lys Ser Lys Lys Leu Gly Gly Asp Phe Gly
    1385            1390            1395

Ser Gly Tyr Ser Leu Gly Ile Ala Ser Lys Thr Lys Ala Val Thr
    1400            1405            1410

Lys Ala Ala Ser Asn Leu Val Ala Gly Ala Leu Gly Thr Glu Lys
    1415            1420            1425

Gln Ile Lys Lys Leu Ser Ser Thr Leu Lys Asp Lys Val Ser Ser
    1430            1435            1440

Ala Ile Asp Ala Gly Leu His Ser Lys Asn Lys Ser Arg Gly Gln
    1445            1450            1455

Leu Lys Gln Ala Lys Ala Leu Asn Ser Ile Glu Gly Tyr Ile Ala
    1460            1465            1470

Gln Gln Thr Asn Arg Leu Ala Ala Thr Ala Lys Lys Arg Asp Lys
    1475            1480            1485

Val Val Ala Gln Leu Lys Ala Ala Asn Thr Lys Met Ala Asp Leu
    1490            1495            1500

Thr Lys Gln Ser Lys Glu Tyr Ala Ala Ser Ile Thr Glu Lys Met
    1505            1510            1515

Gln Ser Tyr Gly Ser Ile Ser Asn Val Asp Ala Glu Asn Pro Gln
    1520            1525            1530

Ser Ile Gln Gln Glu Met Gln Lys Arg Leu Lys Glu Ile Lys Ala
    1535            1540            1545

Phe Gln Ala Asn Val Glu Lys Leu Arg Lys Lys Gly Val Ser Lys
    1550            1555            1560

Asp Ile Ile Ser Asp Ile Leu Glu Ser Gly Val Glu Asn Gly Ser
    1565            1570            1575

Ser Tyr Ala Gln Ala Leu Ala Lys Ser Asp Ala Lys Thr Ile Lys
    1580            1585            1590

Ala Ile Asn Ser Thr Gln Asn Gln Ile Asn Ser Ala Ser Lys Ser
    1595            1600            1605

Met Gly Asn Thr Ala Ala Asn Ala Met Tyr Ser Ala Gly Ile Asn
    1610            1615            1620

Ala Ala Lys Gly Leu Ile Asn Gly Leu Asn Ser Gln Lys Lys Gln
    1625            1630            1635

Leu Glu Lys Thr Ala Lys Ser Ile Ala Ser Thr Ile Thr Asn Ser
    1640            1645            1650

Val Lys Lys Ala Leu Lys Ile His Ser Pro Ser Arg Val Ala Ile
    1655            1660            1665

Glu Leu Gly Lys Phe Phe Thr Gly Gly Leu Gly Asn Gly Val Leu
    1670            1675            1680

Ala Gly Ala Lys Gly Ala Val Gln Ser Thr Asn Lys Met Val Asp
    1685            1690            1695
```

```
Lys Val Val Asn Ala Ala Ser Asn Met Thr Val Pro Thr Ile Thr
    1700                1705                1710

Leu Pro Lys Val Ser Ala Glu Lys Ala Leu Gly Leu Lys Ser Ser
    1715                1720                1725

Asp Leu Asn Arg Thr Ile Thr Val Lys Ala Ile Val Glu Asn Glu
    1730                1735                1740

Ser Lys Asn Asn Ser Asn Ser Asp Leu Ile Asn Ala Ile Glu Lys
    1745                1750                1755

Ser Gly Gly Arg Pro Ile Ile Leu Asn Val Asp Gly Lys Val Ile
    1760                1765                1770

Ala Asp Ser Thr Asn Asn His Leu Gly Asn Ser Thr Ser Leu Ala
    1775                1780                1785

Phe Tyr Gly Lys Gly Leu
    1790

<210> SEQ ID NO 34
<211> LENGTH: 272
<212> TYPE: PRT
<213> ORGANISM: Listeriophage A118

<400> SEQUENCE: 34

Met Ala Thr Ser Leu Ala Leu Val Ile Glu Gly Lys Thr Tyr Met Leu
1               5                   10                  15

Asn Glu Leu Phe Asp Leu Glu Val Gly Glu Val Ser Arg Glu Pro Pro
                20                  25                  30

Gln Ile Val Asn Asn Tyr Thr Glu Phe Ala Gly Ser Asp Gly Ala Arg
            35                  40                  45

Thr Thr Asp Ser Asn Phe Ser Met Phe Pro Ile Ser Ile Leu Cys His
    50                  55                  60

Phe Gln Thr Lys Thr Ala Asp Leu Tyr His Ile Lys Leu Asp Glu Leu
65                  70                  75                  80

Leu Glu Leu Ile Tyr Gln Arg Lys Glu Tyr Phe Leu Val His Ser Lys
                85                  90                  95

Thr Pro Gly Lys Lys Tyr Arg Val His Pro Ser Gly Val Ala Ile Tyr
            100                 105                 110

Arg Lys Ala Pro Gly Tyr Ala Asp Leu Thr Leu Glu Phe Asp Val Phe
        115                 120                 125

Arg Gly Tyr Ser Glu Ser Leu Ser Ser Thr Leu Ser Asp Ser Glu Ile
    130                 135                 140

Asp Cys Asp Lys Trp Gln Phe Gly Gln Gly Leu Ala Met Glu Asp Tyr
145                 150                 155                 160

Arg Tyr Thr His Thr Lys Ser Arg Phe Ile Ile Tyr Asn Gly Gly Ser
                165                 170                 175

Phe Asp Ile Asp Pro Arg Glu His Gln Leu Thr Ile Thr Ile Arg Gly
            180                 185                 190

Gln Asn Glu Gly Glu Leu Val Ile Asn Asn Ile Thr Thr Gly Asp Arg
        195                 200                 205

Phe Ile Tyr Tyr Pro Ala Leu Ser Ala Thr Asp Thr Leu Val Ile Asp
    210                 215                 220

Ser Ala Thr Pro Arg Ile Asn Gly Asn Pro Cys Gly Arg Ser Thr Asn
225                 230                 235                 240

His Gly Leu Ile Ser Leu Gln Lys Gly Glu Asn Leu Ile Glu Ile Ser
                245                 250                 255

Asn Thr Ser His Leu Asp Thr Arg Trp Asp Phe Ser Phe Leu Tyr Lys
            260                 265                 270
```

```
<210> SEQ ID NO 35
<211> LENGTH: 341
<212> TYPE: PRT
<213> ORGANISM: Listeriophage A118

<400> SEQUENCE: 35

Met Asn Ser Asp Ile Ile Val Ala Asp Phe Trp Lys Asn Glu Glu
1               5                   10                  15

Ile Leu Thr Asp Phe Asp Lys Glu Ser Phe Cys Glu Thr Trp Thr Glu
            20                  25                  30

Asn Glu Met Trp Asn Ile Glu Phe Lys Val Thr Gln Thr Asn Lys Asn
        35                  40                  45

Ala Asn Cys Tyr Ser Phe Leu Asp Tyr Glu Ser Ser Val Phe Phe Gly
    50                  55                  60

Gly Gln Glu Phe Val Val Lys Gln Leu Ser His Asp Ala Val Gly Lys
65                  70                  75                  80

Thr Leu Ser Lys Asp Ile Lys Ala Pro His Ile Tyr Tyr Thr Cys Gln
                85                  90                  95

Asp Gly Arg Gln Asp Asp Thr Ile Thr Gly Ser Phe Thr Leu Glu Gln
            100                 105                 110

Cys Leu Thr His Ile Phe Lys Ser Asp Ser Arg Gly Phe Ser Trp Glu
        115                 120                 125

Ile Ile Asp Pro Ser Asn Ile Leu Glu Lys Val Gln Gln Glu Asn Phe
    130                 135                 140

Gly Asn Asn Asn Tyr Leu Thr Leu Ile Asp Gln Leu Leu Asp Asp Tyr
145                 150                 155                 160

Gly Val Val Ile Pro Asp Asn Arg His Leu Val Phe Lys Pro Arg
                165                 170                 175

Glu Asn Tyr Gly Ala Lys Thr Glu Asn Phe Ile Arg Tyr Lys Tyr Asn
            180                 185                 190

Thr Asp Glu Ala Ser Phe Asp Ile Asp Thr Leu Ser Leu Lys Thr Lys
        195                 200                 205

Ile Lys Gly Tyr Gly Lys Val Asp Ser Asn Gly Asn Asn Tyr Phe Ser
    210                 215                 220

Pro Val Thr Tyr Thr Ser Pro Glu Ala Glu Lys Trp Gly Ile Arg Trp
225                 230                 235                 240

Gln Glu Pro Val Ser Asp Glu Arg Tyr Thr Val Val Gly Asn Met Gln
                245                 250                 255

Arg Arg Leu Lys Leu Glu Leu Gln Asp Tyr Pro Ala Thr Thr Gly Ser
            260                 265                 270

Val Ile Leu Lys Asn Asp Tyr Glu Cys Glu Lys Gly Asp Tyr Val Leu
        275                 280                 285

Phe Ile Tyr Glu Pro Leu Gly Ile Asp Tyr Asp Val Gln Ile Val Ala
    290                 295                 300

Tyr Lys Lys Tyr Pro Phe Thr Ile Lys Ala Pro Glu Ile Thr Leu Ser
305                 310                 315                 320

Asn Asn Lys Lys Ser Ile Val Ser Ile Met Ala Gln Leu Ala Lys Val
                325                 330                 335

Leu Lys Gly Ala Lys
            340

<210> SEQ ID NO 36
<211> LENGTH: 163
<212> TYPE: PRT
```

<213> ORGANISM: Listeriophage A118

<400> SEQUENCE: 36

Met Asn Lys Thr Ser Tyr Glu Leu Lys Gln Glu Phe Pro Glu Leu Asn
1               5                   10                  15

Phe Val Ile Asn Asn Asn Leu Pro Thr Lys Leu Phe Gly Leu Ile Gln
            20                  25                  30

Asn Lys Val Val His Leu His Pro Asp Leu Ser Glu Asn Glu Leu Arg
        35                  40                  45

Cys Thr Ile Ile Glu Glu Ala Met His Trp Lys Tyr Thr Ala Gly Asp
    50                  55                  60

Ile Thr Lys Phe Asn Asn Val Glu Asn Ile Lys Gln Glu Lys Phe Ala
65                  70                  75                  80

Arg Arg Lys Ala His Glu Tyr Leu Val Asn Ile Gln Ser Leu Ala Leu
                85                  90                  95

Cys Tyr Asp Leu Gly Tyr Arg Thr Tyr Tyr Glu Ala Ala Thr Phe Leu
            100                 105                 110

Asn Val Thr Glu Lys Phe Leu Ile Glu Ala Val Glu Asn Tyr Arg Glu
        115                 120                 125

Lys Tyr Gly Leu Met Tyr Asn Asn Gly Asn Tyr Ile Ile His Phe Gly
    130                 135                 140

Ser Thr Ile Gln Val Phe Gln Glu Asp Asn Ser Phe Tyr Pro Tyr Asp
145                 150                 155                 160

Tyr Gly Cys

<210> SEQ ID NO 37
<211> LENGTH: 101
<212> TYPE: PRT
<213> ORGANISM: Listeriophage A118

<400> SEQUENCE: 37

Met Ser Arg Lys Glu Leu Arg Lys Lys Gln Trp Glu Val Ile Thr Met
1               5                   10                  15

Ile Glu Lys Ser Lys Thr Leu Thr Asp Arg Lys Asn Leu Ile Lys Lys
            20                  25                  30

Leu Glu Thr Leu Glu Ala Arg Gly Asp Lys Glu Lys Gly Leu Ala Thr
        35                  40                  45

Pro Thr Gln Leu Leu Ser Ile Phe Thr Val Thr Glu Tyr Arg Arg Leu
    50                  55                  60

Ser Lys Lys Leu Thr Asp Thr Glu Ile Ala Glu Asp Met Gly Ile Ser
65                  70                  75                  80

Arg Ser Ala Leu Ile Glu Phe Lys Lys Asn Gly Leu Ser Ile Arg
                85                  90                  95

Gln Lys Val Ala Thr
            100

<210> SEQ ID NO 38
<211> LENGTH: 144
<212> TYPE: PRT
<213> ORGANISM: Listeriophage A118

<400> SEQUENCE: 38

Met Gly Gln Leu Phe Asn Leu Pro Gln Val Glu Asp Ile Asn Tyr Ile
1               5                   10                  15

Gln Thr Val Arg Ala Val Arg Gln Phe Phe Lys Asp Tyr Leu Thr Leu
            20                  25                  30

```
Arg Leu Met Ala Gly Asp Arg Lys Phe Pro Asn Met Thr Thr Met Tyr
         35                  40                  45

Lys Ile Thr Pro Pro Asn Phe Ser Asn Glu Phe His Ser Lys Val Glu
 50                  55                  60

Asp Ala Ala Ile His Asn Val Asp Asn Val His Ala Ala Gln Glu Ala
 65                  70                  75                  80

Val Lys Lys Tyr Asp Ala Ile Met Asn Gln Leu Glu His Ile His Arg
                 85                  90                  95

Lys Ile Leu Phe Glu Lys Phe Ile His Asn Leu Gln Asp Arg Thr Ile
            100                 105                 110

Met Leu Asp Ile Pro Tyr Glu Glu Arg Gln Tyr Lys Arg Glu Lys Arg
        115                 120                 125

Lys Ala Val Ile Glu Leu Ala Thr Thr Leu Gly Ile Glu Val Leu Asn
130                 135                 140
```

<210> SEQ ID NO 39
<211> LENGTH: 36
<212> TYPE: DNA
<213> ORGANISM: Artificial Sequence
<220> FEATURE:
<223> OTHER INFORMATION: Synthetic oligonucleotide sequence

<400> SEQUENCE: 39
gaggcgcgcc ttatctggtt aataagccgt ttccgg                    36

<210> SEQ ID NO 40
<211> LENGTH: 36
<212> TYPE: DNA
<213> ORGANISM: Artificial Sequence
<220> FEATURE:
<223> OTHER INFORMATION: Synthetic oligonucleotide sequence

<400> SEQUENCE: 40
gagcggccgc ttatcttttt cctgtattaa cttctg                    36

<210> SEQ ID NO 41
<211> LENGTH: 36
<212> TYPE: DNA
<213> ORGANISM: Artificial Sequence
<220> FEATURE:
<223> OTHER INFORMATION: Synthetic oligonucleotide sequence

<400> SEQUENCE: 41
gagcggccgc ttacataatt gttacttggc gaagag                    36

<210> SEQ ID NO 42
<211> LENGTH: 34
<212> TYPE: DNA
<213> ORGANISM: Artificial Sequence
<220> FEATURE:
<223> OTHER INFORMATION: Synthetic oligonucleotide sequence

<400> SEQUENCE: 42
gaggcgcgcc gaattcgact ctctagcttg aggc                      34

<210> SEQ ID NO 43
<211> LENGTH: 31
<212> TYPE: DNA
<213> ORGANISM: Artificial Sequence
<220> FEATURE:
<223> OTHER INFORMATION: Synthetic oligonucleotide sequence

<400> SEQUENCE: 43
gagcggccgc tcactgcccg ctttccagtc g					31

<210> SEQ ID NO 44
<211> LENGTH: 37
<212> TYPE: DNA
<213> ORGANISM: Artificial Sequence
<220> FEATURE:
<223> OTHER INFORMATION: Synthetic oligonucleotide sequence

<400> SEQUENCE: 44
gagcggccgc ttacattaca gttagctggc gtaatgc					37

<210> SEQ ID NO 45
<211> LENGTH: 51
<212> TYPE: DNA
<213> ORGANISM: Artificial Sequence
<220> FEATURE:
<223> OTHER INFORMATION: Synthetic oligonucleotide sequence

<400> SEQUENCE: 45
ctctgacatt ttacaattt tagtcattct ataacctcct taatagtttc c					51

<210> SEQ ID NO 46
<211> LENGTH: 51
<212> TYPE: DNA
<213> ORGANISM: Artificial Sequence
<220> FEATURE:
<223> OTHER INFORMATION: Synthetic oligonucleotide sequence

<400> SEQUENCE: 46
ggaaactatt aaggaggtta tagaatgact aaaattgtaa aatgtcaga g					51

<210> SEQ ID NO 47
<211> LENGTH: 36
<212> TYPE: DNA
<213> ORGANISM: Artificial Sequence
<220> FEATURE:
<223> OTHER INFORMATION: Synthetic oligonucleotide sequence

<400> SEQUENCE: 47
gtgagcggat aacaattagg aagtgggaat ggatgg					36

<210> SEQ ID NO 48
<211> LENGTH: 37
<212> TYPE: DNA
<213> ORGANISM: Artificial Sequence
<220> FEATURE:
<223> OTHER INFORMATION: Synthetic oligonucleotide sequence

<400> SEQUENCE: 48
ggctagctgt cgactattac ataattgtta cttggcg					37

<210> SEQ ID NO 49
<211> LENGTH: 42
<212> TYPE: DNA
<213> ORGANISM: Artificial Sequence
<220> FEATURE:
<223> OTHER INFORMATION: Synthetic oligonucleotide sequence

<400> SEQUENCE: 49
ggctagctgt cgactttaca ttacagttag ctggcgtaat gc					42

<210> SEQ ID NO 50
<211> LENGTH: 50
<212> TYPE: DNA
<213> ORGANISM: Artificial Sequence

```
<220> FEATURE:
<223> OTHER INFORMATION: Synthetic oligonucleotide sequence

<400> SEQUENCE: 50
cgcagtattt tcttttgtat tccaatttgt tttctcttcc tctgaaaccg            50

<210> SEQ ID NO 51
<211> LENGTH: 50
<212> TYPE: DNA
<213> ORGANISM: Artificial Sequence
<220> FEATURE:
<223> OTHER INFORMATION: Synthetic oligonucleotide sequence

<400> SEQUENCE: 51
gtttcagagg aagagaaaac aaattggaat acaaaagaaa atactgcggg            50

<210> SEQ ID NO 52
<211> LENGTH: 45
<212> TYPE: DNA
<213> ORGANISM: Artificial Sequence
<220> FEATURE:
<223> OTHER INFORMATION: Synthetic oligonucleotidfe sequence

<400> SEQUENCE: 52
ggctagctgt cgactattat ttatcatcct ctccatattt tttgc                 45
```